United States Patent
Vankayalapati et al.

(10) Patent No.: US 10,689,376 B2
(45) Date of Patent: Jun. 23, 2020

(54) SUBSTITUTED-3H-IMIDAZO [4,5-C] PYRIDINE AND 1H-PYRROLO[2,3-C]PYRIDINE SERIES OF NOVEL ECTONUCLEOTIDE PYROPHOSPHATASE/PHOSPHODIESTERASE-1 (ENPP1) AND STIMULATOR FOR INTERFERON GENES (STING) MODULATORS AS CANCER IMMUNOTHERAPEUTICS

(71) Applicants: Stingray Therapeutics, Inc., Houston, TX (US); The University of Utah, Salt Lake City, UT (US)

(72) Inventors: Hariprasad Vankayalapati, Draper, UT (US); Xiaohui Liu, Holladay, UT (US); Gurusankar Ramamoorthy, Salt Lake City, UT (US); Sunil Sharma, Phoenix, AZ (US); Mohan Rao Kaadige, Scottdale, AZ (US); Alexis Weston, Phoenix, AZ (US); Trason Thode, Phoenix, AZ (US)

(73) Assignees: Stingray Therapeutics, Inc., Houston, TX (US); The University of Utah, Salt Lake City, UT (US)

( * ) Notice: Subject to any disclaimer, the term of this patent is extended or adjusted under 35 U.S.C. 154(b) by 0 days.

(21) Appl. No.: 16/047,915

(22) Filed: Jul. 27, 2018

(65) Prior Publication Data

US 2019/0031655 A1 Jan. 31, 2019

Related U.S. Application Data

(60) Provisional application No. 62/537,758, filed on Jul. 27, 2017.

(51) Int. Cl.
C07D 471/04 (2006.01)

(52) U.S. Cl.
CPC .................. *C07D 471/04* (2013.01)

(58) Field of Classification Search
CPC .................................................. C07D 471/04

USPC ............................................................ 514/303
See application file for complete search history.

(56) References Cited

U.S. PATENT DOCUMENTS 5,081,253 A  1/1992  Santilli et al.
6,362,208 B1  3/2002  Shibuya et al.

FOREIGN PATENT DOCUMENTS

WO  2014/176258 A1  10/2014
WO  WO-2014176258 A1 * 10/2014  ........... C07D 403/12

OTHER PUBLICATIONS

Lei Chang et al. lnnidazopyridine-Purine-Thioacetannide Derivatives; Potent Inhibitors of Nucleotide Pyrophosphatase/Phosphodiesterase 1 (NPP1). (Year: 2014).*
Abstract 3077: Preclinical studies of SR-8314, a highly selective ENPP1 inhibitor and an activatoreof STING pathway. (Year: 2019).*
International Search Report and Written Opinion for corresponding PCT Application No. PCT/US18/44183 dated Oct. 16, 2018.
Hang et al., Imidazopyridine- and Purine-Thioacetamide Derivatives: Potent Inhibitors of Nucleotide Pyrophosphatase/Phosphodiesterase 1 (NPP1), J. Med. Chem., 2014, vol. 57(23), pp. 10080-10100.
Aerts et al., "The expression of ecto-nucleotide pyrophosphatase/phosphodiesterase 1 (E-NPP1) is correclated with astrocytic tumor grade", Clin Neurol Neurosurg. 2011, vol. 113(3), pp. 224-229.

* cited by examiner

*Primary Examiner* — Rita J Desai
(74) *Attorney, Agent, or Firm* — Wood, Phillips, Katz, Clark & Mortimer

(57) ABSTRACT

Substituted-3H-imidazo[4,5-c]pyridine and 1H-pyrrolo[2,3-c]pyridine series of novel Ectonucleotide Pyrophosphatase/Phosphodiesterase-1 (ENPP1) and related compounds, which are useful as inhibitors of ENPP1; synthetic methods for making the compounds; pharmaceutical compositions comprising the compounds; and methods of using the compounds and compositions to treat disorders associated with dysfunction of the ENPP1.

4 Claims, 4 Drawing Sheets
(4 of 4 Drawing Sheet(s) Filed in Color)

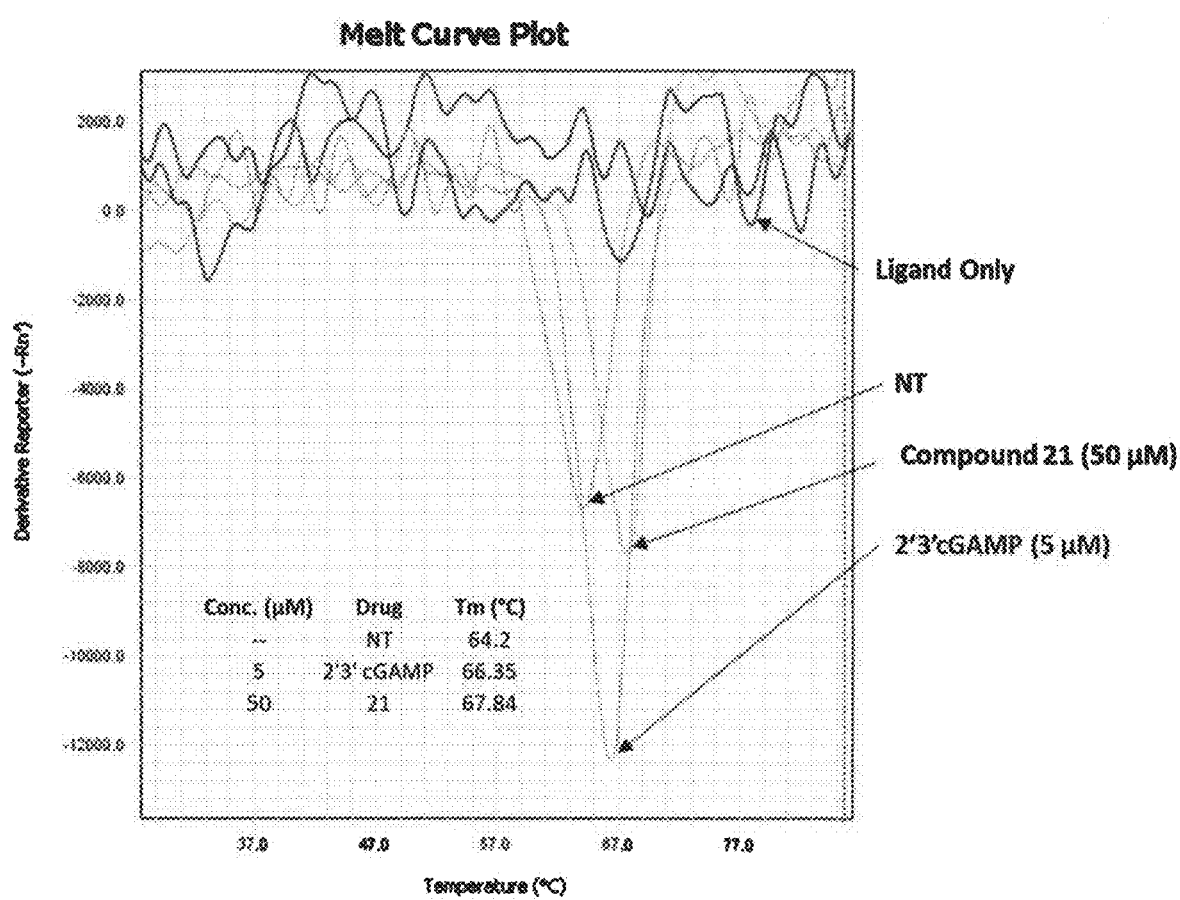

SUBSTITUTED-3H-IMIDAZO [4,5-C] PYRIDINE AND 1H-PYRROLO[2,3-C]PYRIDINE SERIES OF NOVEL ECTONUCLEOTIDE PYROPHOSPHATASE/PHOSPHODIESTERASE-1 (ENPP1) AND STIMULATOR FOR INTERFERON GENES (STING) MODULATORS AS CANCER IMMUNOTHERAPEUTICS

BACKGROUND

Ectonucleotide Pyrophophatase/Phosphodiesterase (ENPP) family members include seven isoforms, ENPP1-7, which are type II transmembrane glycoproteins or ectoenzymes. Mass spectrometry and proteomics analysis from more than 370 protein targets led to the identification of an extracellular protein ENPP1 as one of the top hit which exhibited high hydrolytic activity. ATP is an identified substrate of ENPP1, which is hydrolyzed to AMP and PPi. CD73 converts AMP to adenosine and inorganic phosphate (Pi). The kinetic experimental data indicates that the ENPP1 is capable of hydrolyzing ATP. These ectonucleotide enzymes are involved in the hydrolysis of pyrophosphate (PPi) and phosphodiester bonds in extracellular nucleotides; such as triphosphates, oligonucleotides and that generates nucleoside 5'-monophosphates. One of the key isoforms, ENPP1 (Plasma cell membrane glycoprotein-1, PC-1), is involved in a number of physiological processes, such as development, formation and trafficking, as well as in pathophysiological conditions. Aberrant ENPP1 expression has been detected in breast cancers relative to normal mammary epithelium, an evidence of its potential in the development of bone metastasis (occurs in approximately 80% cases), Hodgkin's lymphoma, hepatocellular carcinoma, follicular lymphoma, glioblastoma and in other malignant tumor tissues.

Recent reports suggest that the cyclic dinucleotides (CDNs), a substrate for ENPP1, stimulate innate immunity via STING-dependent activation of interferon genes. ENPP1 inhibition of STING pathway activation is critical for tumor control, similar to that of checkpoint inhibitors such as anti PD-1 or PD-L1 which are promising immunotherapeutics for various cancers. In addition, mutations in ENPP1 were associated with several disorders including infantile arterial calcification (generalized arterial calcification of infancy or GACI), ossification of the posterior longitudinal ligament of the spine and insulin signaling and resistance. ENPP1 expression is high in bone and cartilage and is implicated in lung and kidney fibrosis. A correlation was also found between expression of ENPP1 and the grade of astrocytic tumor. Another study reported that ENPP1 was required to maintain the undifferentiated and proliferative state of glioblastoma stem-like cells. Therefore, ENPP1 is an attractive druggable target for the development of novel anticancer, cardiovascular, diabetes, obesity and anti-fibrotic therapeutics.

Importance of ENPP1 activity was further investigated from both direct binding assay and in vitro cellular efficacy on MDA-MB231 cells. The siRNA-based knock down of ENPP1 significantly reduced its catalytic activity both in cell specific and in vivo experiments. These experiments demonstrated that the ENPP1 activity was abolished on treatment with siRNA. This further supports the validity of this target in certain diseases. It has been shown recently that the bisphosphothionate analog of endogenous cGAMP is resistant to hydrolysis by ENPP1 phosphodiesterase, and particularly the cyclic dinucleotides (CDNs) are more potent at inducing IFN-β secretion in human THP1 cells by a mechanism of inhibiting the ENPP1 activity and simultaneous STING activation responses.

There is ample evidence that ENPP1 expression is prominent in human primary breast tumors relative to normal mammary epithelium, with highest levels observed in breast-bone metastasis. These data not only support a potential role for ENPP1 in breast-bone metastasis, but also support as a potential prognostic marker for breast cancer. These results from target validation experiments clearly support the pharmacological role of ENPP1 for the development of novel immunotherapeutics for cancers.

Furthermore, ENPP1 activity has also been implicated in diseases caused by bacteria and/or viruses, and therefore modulators of ENPP1 can be used to treat bacterial and/or viral diseases and conditions.

SUMMARY OF THE INVENTION

The invention, in one aspect, relates to compounds of Formula I:

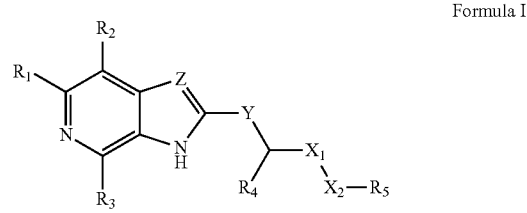

Formula I wherein
Y is S;
Z is —H or —N;
$X_1$ is —C═O or —NH,
$X_2$ is —C═O or —NH, provided that if $X_1$ is —C═O, then $X_2$ is —NH; and if $X_1$ is —NH, then $X_2$ is —C═O;
$R_1$ is selected from the group consisting of —H, halogen, —OCF$_3$, —CF$_3$, —CN, OCH$_3$, and —CH$_3$;
$R_2$ is selected from the group consisting of —H, —NH$_2$, —OH, and —CH$_3$;
$R_3$ is selected from the group consisting of —H, —NH$_2$, —OH, and —CH$_3$;
$R_4$ is selected from the group consisting of —H, —CH$_2$—CH$_3$ and —CH$_3$;
$R_5$ is selected from the group consisting of

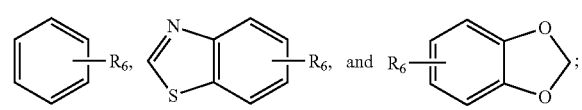

and
$R_6$ is selected from the group consisting of —OCH$_3$, OH, F, Cl, —CH$_3$, O—CH$_2$—CH$_3$, and OCH$_2$—CF$_3$, OCHF$_2$,
or an isomer or a pharmaceutically acceptable salt thereof.
In one preferred embodiment,
Z is —N;
$X_1$ is —C═O;
$X_2$ is —NH;
$R_1$ is selected from the group consisting of halogen and —CN;
$R_2$ is selected from the group consisting of —H and —CH$_3$;

R₃ is —H;
R₄ is —H;
R₅ is
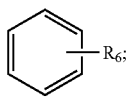
and
R₆ is selected from the group consisting of —OCH₃, and OH.
In a further preferred embodiment, R₁ is selected from the group consisting of —Cl and —CN.
Examples of the provided compounds include:
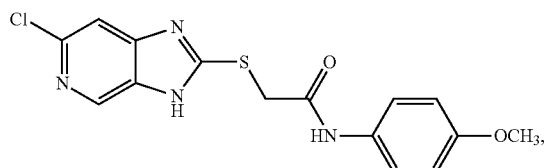
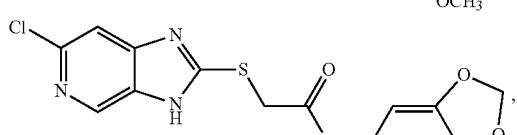
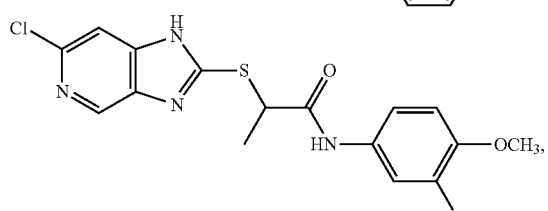
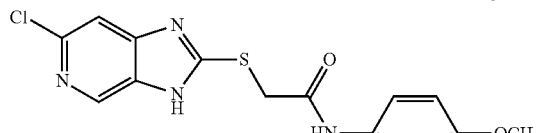
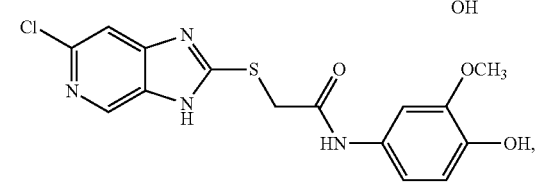
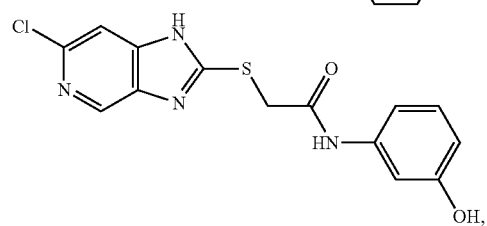
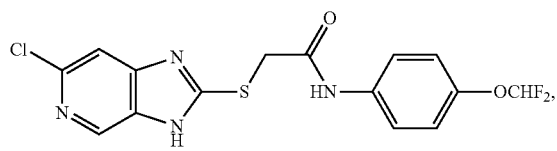
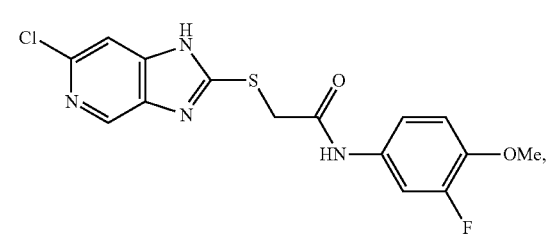
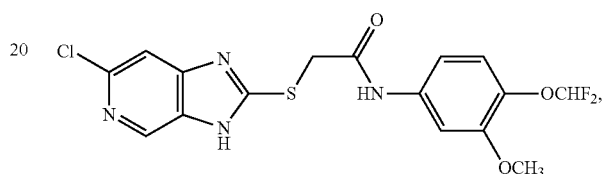
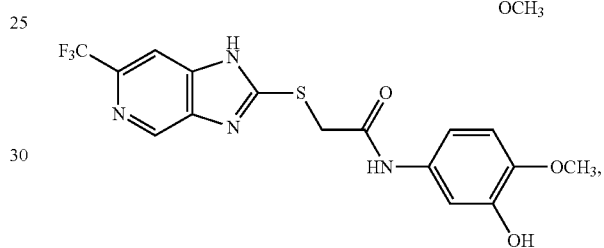
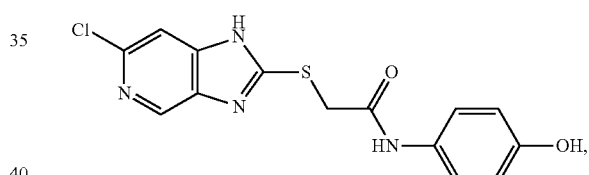
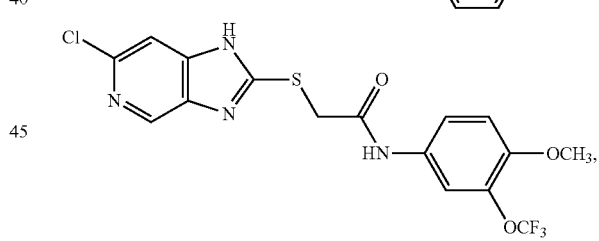
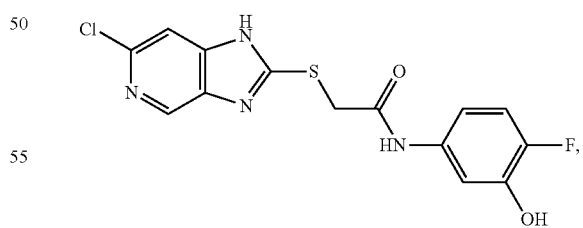
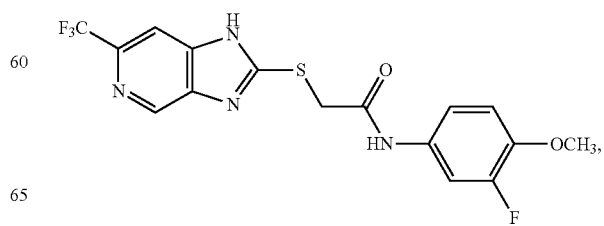

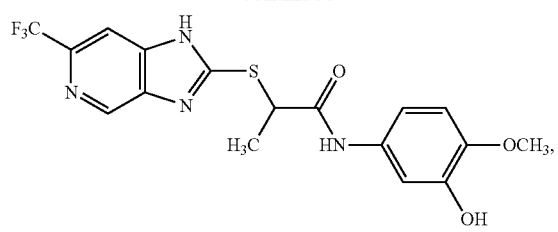
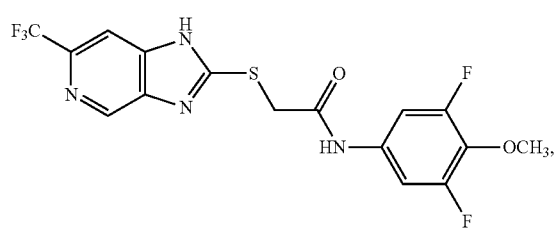
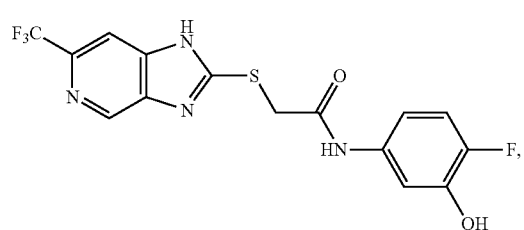
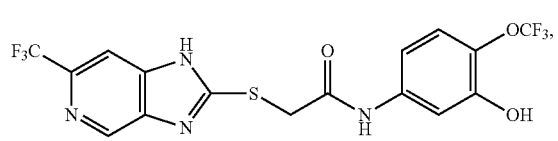
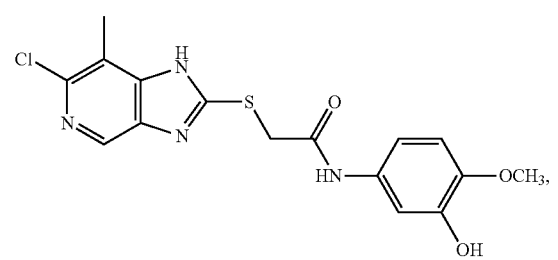
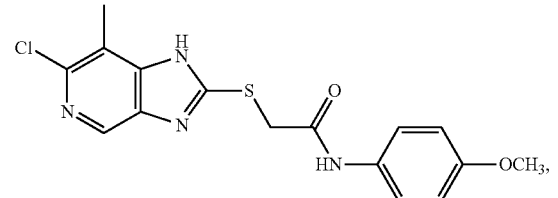
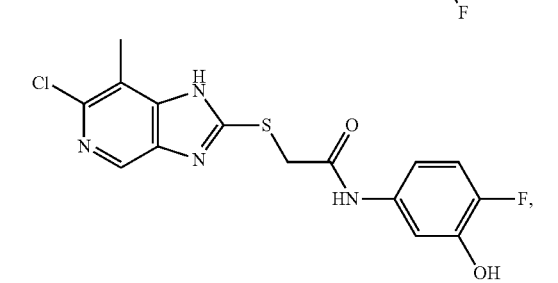
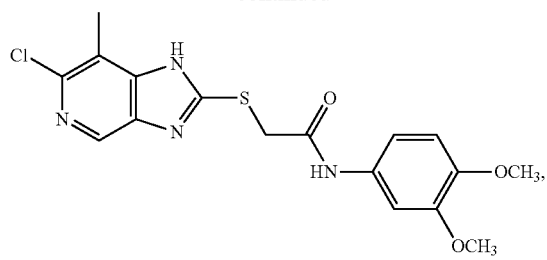
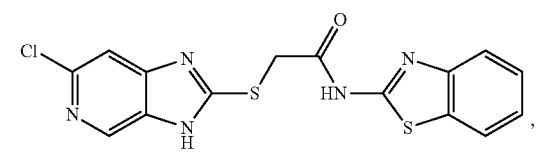
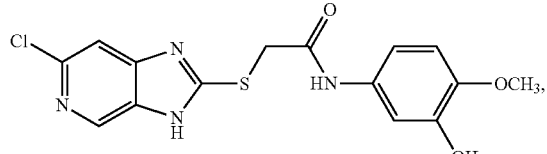
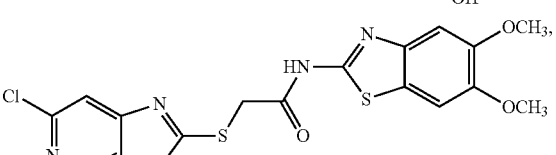
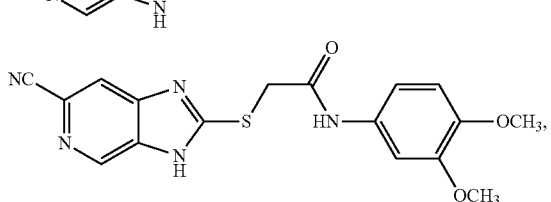
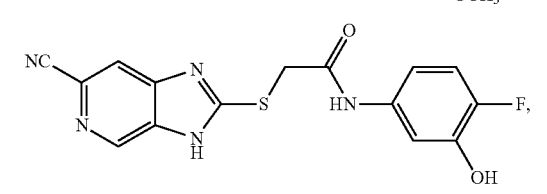
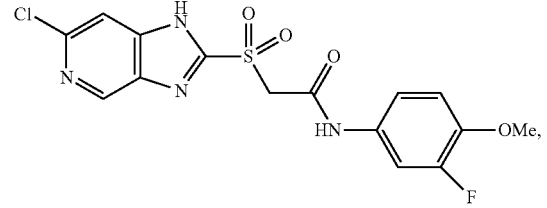
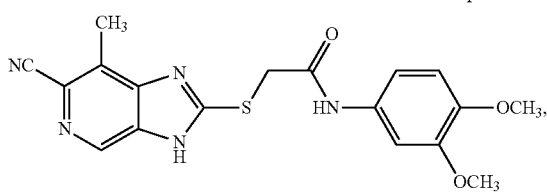
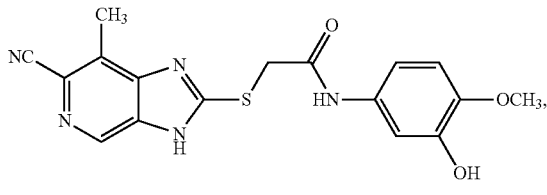

-continued

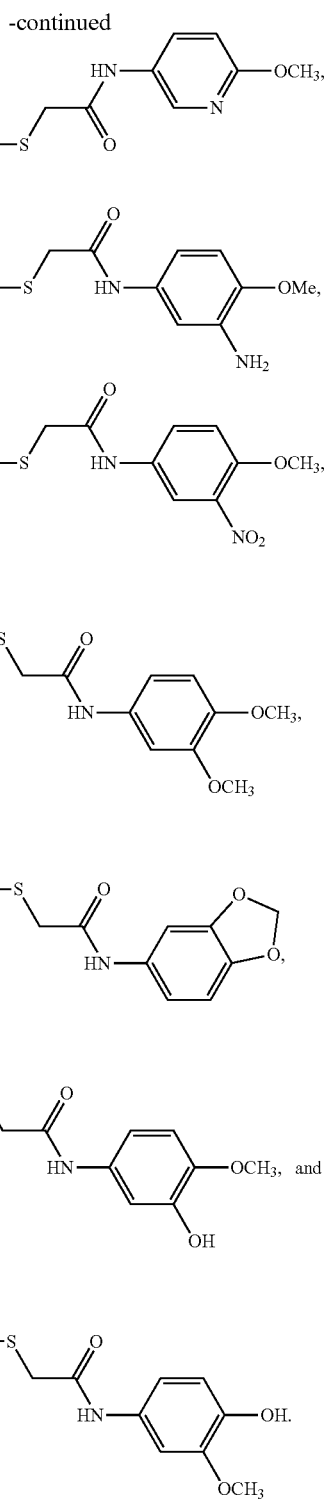

The invention also includes hydrates, solvates, polymorphs, isomers, tautomers of the compounds, pharmaceutically acceptable salts of the compounds and pharmaceutically acceptable salts of the tautomers.

The invention also provides pharmaceutical formulations, medicaments, methods including the compounds, methods of preparing pharmaceuticals formulations, medicaments, compounds, and methods of treating patients with the provided pharmaceutical formulations and compounds.

The compounds of the invention were identified by structure-based, computational docking and binding free energies.

Also disclosed are pharmaceutical compositions comprising a therapeutically effective amount of a disclosed compound and a pharmaceutically acceptable carrier.

Also disclosed are synthetic methods for making the disclosed compounds. In a further aspect, disclosed are the products of the disclosed synthetic methods.

Also disclosed are methods for the treatment of a disorder associated with an ENPP1 activity dysfunction in a mammal comprising the step of administering to the mammal a therapeutically effective amount of a disclosed compound, or a pharmaceutically acceptable salt, tautomer, isomer, hydrate, solvate, or polymorph thereof.

Also disclosed are methods for inhibition of ENPP1 activity in a mammal comprising the step of administering to the mammal a therapeutically effective amount of least one disclosed compound, or a pharmaceutically acceptable salt, tautomer, isomer, hydrate, solvate, or polymorph thereof.

Also disclosed are methods for inhibiting ENPP1 activity in at least one cell, comprising the step of contacting the at least one cell with an effective amount of least one disclosed compound, or a pharmaceutically acceptable salt, tautomer, isomer, hydrate, solvate, or polymorph thereof.

Also disclosed are methods for treating a disorder associated with an ENPP1 activity dysfunction in a mammal through eliciting an immunotherapeutic response in the mammal, comprising administering to the mammal a therapeutically effective amount of a disclosed compound, or a pharmaceutically acceptable salt, tautomer, isomer, hydrate, solvate, or polymorph thereof, wherein this compound causes an immunotherapeutic response beneficial in the treatment of the disorder associated with an ENPP1 activity. Such disorder can be, but is not limited to, any type of cancer or any disease caused by bacteria and/or viruses wherein ENPP1 activity has been implicated.

Also disclosed are pharmaceutical compositions comprising a pharmaceutically acceptable carrier and an effective amount of a disclosed compound, or a pharmaceutically acceptable salt, tautomer, isomer, hydrate, solvate, or polymorph thereof.

Also disclosed are kits comprising at least one disclosed compound, or a pharmaceutically acceptable salt, tautomer, isomer, hydrate, solvate, or polymorph thereof.

Also disclosed are methods for manufacturing a medicament comprising, combining at least one disclosed compound or at least one disclosed product with a pharmaceutically acceptable carrier or diluent. In a further aspect, the invention relates to the use of a disclosed compound in the manufacture of a medicament for the treatment of a a disorder associated with an ENPP1 activity dysfunction. In a further aspect, the invention relates to the uses of disclosed compounds in the manufacture of a medicament for the treatment of a a disorder of uncontrolled cellular proliferation.

Also disclosed are uses of a disclosed compound or a disclosed product in the manufacture of a medicament for the treatment of a disorder associated with an ENPP1 dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a chart of ENPP1 Thermal Shift Assay for a compound of the invention.

DETAILED DESCRIPTION OF THE INVENTION

A. Definitions

Figure 1:
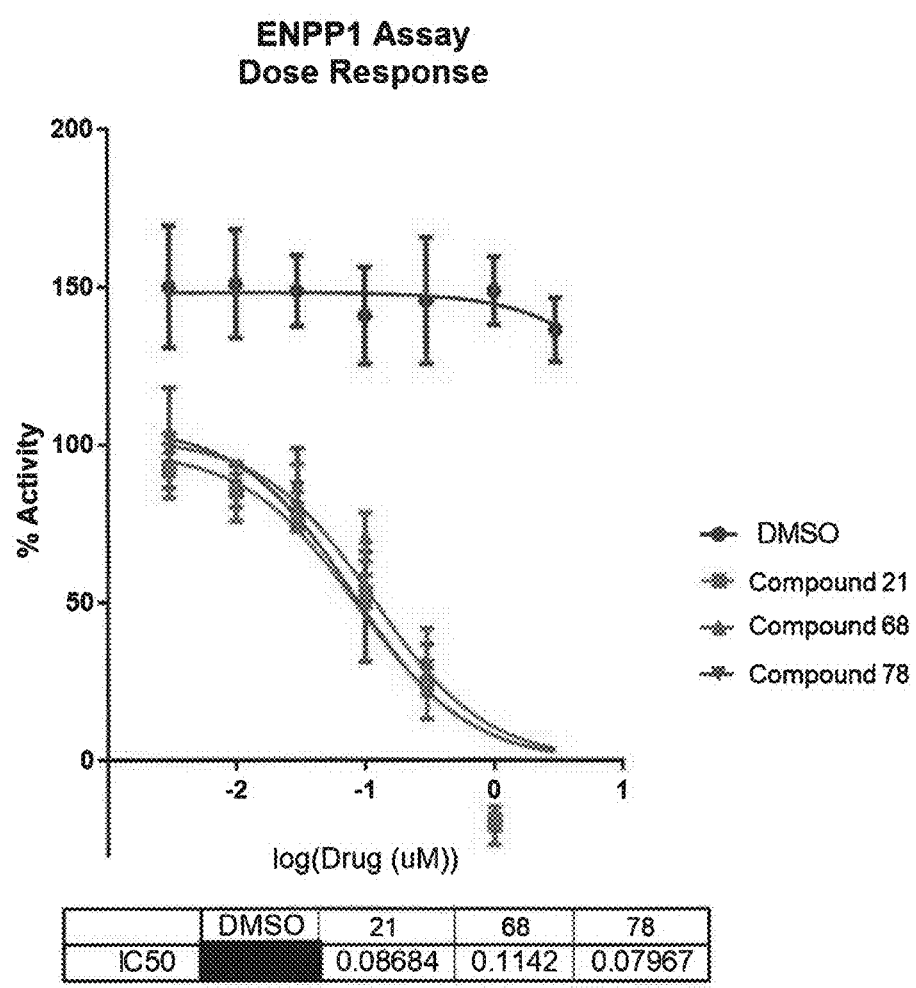
FIG. 1 is a chart of ENPP1 Inhibition Assay for TMP for some of the compounds of the invention.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the term "ENPP1" refers to Ectonucleotide Pyrophophatase/Phosphodiesterase.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with an ENPP1 dysfunction prior to the administering step. In some aspects of the disclosed method, the subject has been diagnosed with a need for inhibition of ENPP1 prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, zebra fish etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder of uncontrolled cellular proliferation" means having been subjected to a physical examination by a person of skill, for example, a physician, and found to have a condition that can be diagnosed or treated by a compound or composition that can inhibit ENPP1. As a further example, "diagnosed with a need for inhibition of ENPP1" refers to having been subjected to a physical examination by a person of skill, for example, a physician, and found to have a condition characterized by an ENPP1 dysfunction. Such a diagnosis can be in reference to a disorder, such as a disorder of uncontrolled cellular proliferation, cancer and the like, as discussed herein. For example, "diagnosed with a need for treatment of one or more disorders of uncontrolled cellular proliferation associated with an ENPP1 dysfunction" means having been subjected to a physical examination by a person of skill, for example, a physician, and found to have one or more disorders of uncontrolled cellular proliferation associated with an ENPP1 dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a dysfunction of ENPP1) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, intraurethral administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ can refer to the concentration of a substance that is required for 50% inhibition in vivo or the inhibition is measured in vitro, as further defined elsewhere herein. Alternatively, $IC_{50}$ refers to the half maximal (50%) inhibitory concentration (IC) of a substance. The inhibition can be measured in a cell-line such as AN3 CA, BT-20, BT-549, HCT 116, HER218, MCF7, MDA-MB-231, MDA-MB-235, MDA-MB-435S, MDA-MB-468, PANG-1, PC-3, SK-N-MC, T-47D, and U-87 MG.

The term "pharmaceutically acceptable" describes a material that is not biologically or otherwise undesirable, i.e., without causing an unacceptable level of undesirable biological effects or interacting in a deleterious manner.

The term "stable," as used herein, refers to compounds that are not substantially altered when subjected to conditions to allow for their production, detection, and, in certain aspects, their recovery, purification, and use for one or more of the purposes disclosed herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

For example, a "C1-C3 alkyl" group can be selected from methyl, ethyl, n-propyl, propyl, and cyclopropyl, or from a subset thereof. In certain aspects, the "C1-C3 alkyl" group can be optionally further substituted. As a further example, a "C1-C4 alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "C1-C4 alkyl" group can be optionally further substituted. As a further example, a "C1-C6 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "C1-C6 alkyl" group can be optionally further substituted. As a further example, a "C1-C8 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group can be optionally further substituted.

As a further example, a "C1-C12 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, t-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, nitrile, sulfonamide, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "halogen," "halide," and "halo," as used herein, refer to the halogens fluorine, chlorine, bromine, and iodine. It is also contemplated that, in various aspects, halogen can be selected from fluoro, chloro, bromo, and iodo. For example, halogen can be selected from fluoro, chloro, and bromo. As a further example, halogen can be selected from fluoro and chloro. As a further example, halogen can be selected from chloro and bromo. As a further example, halogen can be selected from bromo and iodo. As a further example, halogen can be selected from chloro, bromo, and iodo. In one aspect, halogen can be fluoro. In a further aspect, halogen can be chloro. In a still further aspect, halogen is bromo. In a yet further aspect, halogen is iodo.

It is also contemplated that, in certain aspects, pseudohalogens (e.g. triflate, mesylate, tosylate, brosylate, etc.) can be used in place of halogens. For example, in certain aspects, halogen can be replaced by pseudohalogen. As a further example, pseudohalogen can be selected from triflate, mesylate, tosylate, and brosylate. In one aspect, pseudohalogen is triflate. In a further aspect, pseudohalogen is mesylate. In a further aspect, pseudohalogen is tosylate. In a further aspect, pseudohalogen is brosylate.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydropyran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture.

Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

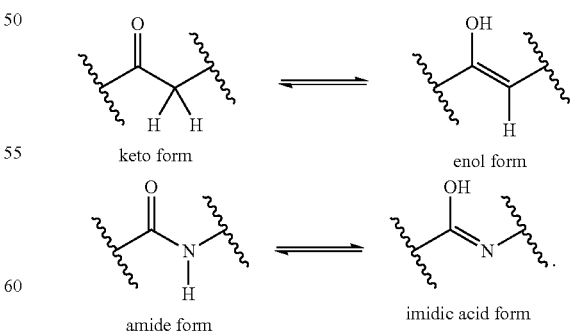

keto form    enol form amide form    imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

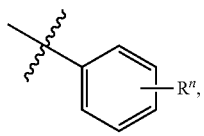

which is understood to be equivalent to a formula:

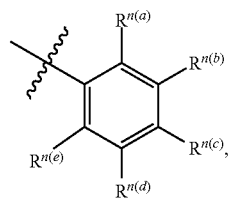

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Sigma-Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991); March's *Advanced Organic Chemistry*, (John Wiley and Sons, 4th Edition); and Larock's *Comprehensive Organic Transformations* (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of ENPP1. Moreover, in one aspect, the compounds of the invention are useful in the treatment of disorders of uncontrolled cellular proliferations. In a further aspect, the disorder of uncontrolled cellular proliferation is a cancer or a tumor. In a still further aspect, the disorder of uncontrolled cellular proliferation is associated with an ENPP1 dysfunction, as further described herein.

In another aspect, the compounds of the invention are useful in the treatment of diseases of bacterial or viral origin. Accordingly, in one aspect, the invention provides a method of treating a disease caused by bacteria or viruses, comprising administering to a subject a therapeutically effective amount of a compound of the invention.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound of Formula I:

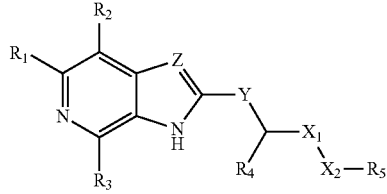

Formula I wherein

Y is S;

Z is —H or —N;

$X_1$ is —C═O or —NH, $X_2$ is —C═O or —NH, provided that if $X_1$ is —C═O, then $X_2$ is —NH; and if $X_1$ is —NH, then $X_2$ is —C═O;

$R_1$ is selected from the group consisting of —H, halogen, —OCF$_3$, —CF$_3$, —CN, OCH$_3$, and —CH$_3$;

$R_2$ is selected from the group consisting of —H, —NH$_2$, —OH, and —CH$_3$;

$R_3$ is selected from the group consisting of —H, —NH$_2$, —OH, and —CH$_3$;

$R_4$ is selected from the group consisting of —H, —CH$_2$—CH$_3$ and —CH$_3$;

$R_5$ is selected from the group consisting of

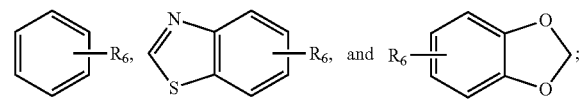

and $R_6$ is selected from the group consisting of —OCH$_3$, OH, F, Cl, —CH$_3$, O—CH$_2$—CH$_3$, and OCH$_2$—CF$_3$, OCHF$_2$, or an isomer or a pharmaceutically acceptable salt thereof.

In one preferred embodiment,

Z is —N;

$X_1$ is —C═O;

$X_2$ is —NH;

$R_1$ is selected from the group consisting of halogen and —CN;

$R_2$ is selected from the group consisting of —H and —CH$_3$;

$R_3$ is —H;

$R_4$ is —H;

$R_5$ is

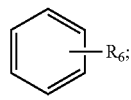

and $R_6$ is selected from the group consisting of —OCH$_3$, and OH.

In a further preferred embodiment, $R_1$ is selected from the group consisting of —Cl and —CN.

Examples of the provided compounds include:

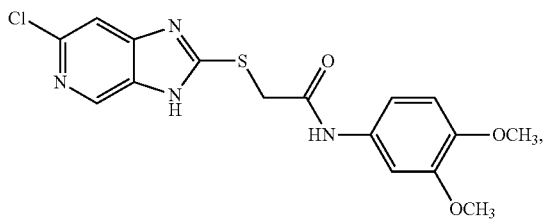

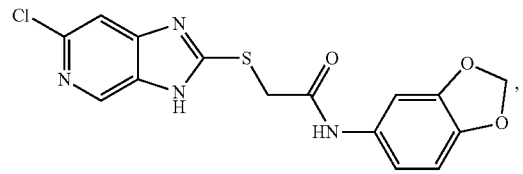

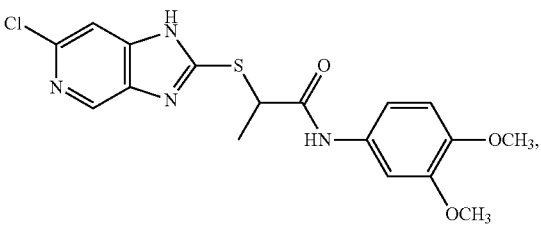

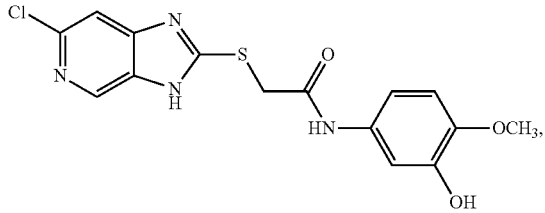

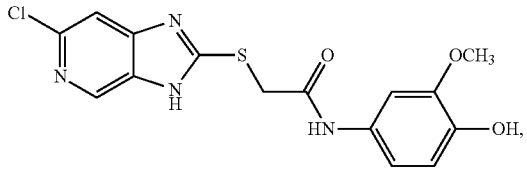

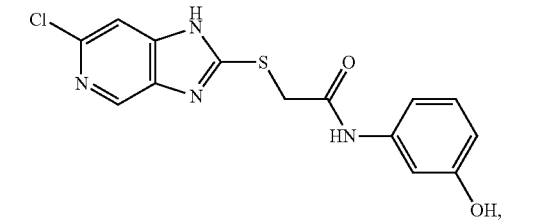

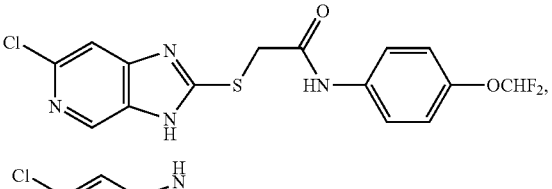

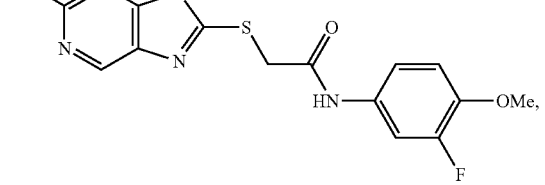

-continued

The invention also provides a pharmaceutical composition comprising a therapeutically effective amount of any of a compound of the invention and a pharmaceutically acceptable carrier.

The invention also provides a method for the treatment of a disorder of uncontrolled cellular proliferation in a mammal, the method comprising the step of administering to the mammal an effective amount of any of the compounds of the invention.

The invention also provides a method for decreasing ENPP1 activity in a mammal, the method comprising the step of administering to the mammal an effective amount of any of the compounds of the invention.

The invention also provides a method for inhibiting ENPP1 activity in a mammal, the method comprising the step of administering to the mammal an effective amount of any of the compounds of the invention.

C. Methods of Making the Compounds

In one aspect, the invention relates to methods of making compounds useful as inhibitors of ENPP1. In a further aspect, the products of disclosed methods of making are modulators of ENPP1 activity.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

Where reaction conditions and amounts of ingredients are not stated, it is believed that it is within a skill in the art to determine them. It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

D. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In a further aspect, the invention relates to pharmaceutical compositions comprising a pharmaceutically acceptable carrier and an effective amount of the product of a disclosed synthetic method. In a further aspect, the effective amount is a therapeutically effective amount. In a further aspect, the effective amount is a prophylactically effective amount. In a further aspect, the compound is a disclosed compound.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof; can also be prepared in powder or liquid concentrate form.

In the treatment conditions which require inhibition or negative modulation of ENPP1 protein activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibiting or negatively modulating ENPP1 protein activity (e.g., treatment of a disorder of uncontrolled cellular proliferation, or one or more neurodegenerative disorders associated with ENPP1 dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Methods of Using the Compounds and Compositions

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders wherein the patient or subject would benefit from inhibition or negative modulation of ENPP1. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which ENPP1 inhibition is predicted to be beneficial, in a subject comprising the step of administering to the subject at least one disclosed compound; at least one disclosed pharmaceutical composition; and/or at least one disclosed product in a dosage and amount effective to treat the disorder in the subject.

In one aspect, provided is a method for treating a disorder of uncontrolled cellular proliferation, comprising: administering to a subject at least one disclosed compound; at least one disclosed pharmaceutical composition; and/or at least one disclosed product in a dosage and amount effective to treat the disorder in the subject. In a further aspect, provided is a method for treating or preventing a neurodegenerative disorder, comprising: administering to a subject at least one disclosed compound; at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

The invention is directed at the use of described chemical compositions to treat diseases or disorders in patients (preferably human) wherein wherein ENPP1 inhibition would be predicted to have a therapeutic effect, such as disorders of uncontrolled cellular proliferation (e.g. cancers) and neurodegenerative disorders such as Alzheimer's disease, Huntington's disease, and Parkinson's disease, diseases caused by bacteria and/or viruses, by administering one or more disclosed compounds or products.

The compounds of the invention can also be used for immunotherapy. In one embodiment, the compounds of the invention treat disorders of uncontrolled cellular proliferation, and/or diseases caused by bacteria and/or viruses through immunotherapy, meaning that the compounds elicit immunotherapeutic response which results in the treatment of these diseases.

The compounds disclosed herein are useful for treating, preventing, ameliorating, controlling or reducing the risk of a variety of disorders of uncontrolled cellular proliferation.

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

Examples of disorders treatable with the provided compounds include a disorder of uncontrolled cellular proliferation. In a yet further aspect, the disorder of uncontrolled cellular proliferation is cancer. In a yet further aspect, the cancer is a leukemia. In an even further aspect, the cancer is a sarcoma. In a still further aspect, the cancer is a solid tumor. In a yet further aspect, the cancer is a lymphoma.

It is understood that cancer refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck;

gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In various aspects, disorders associated with an ENPP1 dysfunction include neurodegenerative disorders. In a further aspect, the neurodegenerative disease is selected from Alzheimer's disease, Parkinson's disease, and Huntington's disease.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of an ENPP1 inhibitor for improving treatment outcomes in the context of disorders of uncontrolled cellular proliferation, including cancer. That is, in one aspect, the invention relates to a cotherapeutic method comprising the step of administering to a mammal an effective amount and dosage of at least one compound of the invention in connection with cancer therapy.

In a further aspect, administration improves treatment outcomes in the context of cancer therapy. Administration in connection with cancer therapy can be continuous or intermittent. Administration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-cancer therapeutic agents or other known therapeutic agents.

In the treatment of conditions which require inhibition or negative modulation of ENPP1, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for inhibiting or negatively modulating ENPP1 in at least one cell, comprising the step of contacting the at least one cell with at least one compound of the invention, in an amount effective to modulate or activate ENPP1 activity response, e.g. in the at least one cell. In a further aspect, the cell is mammalian, for example human. In a further aspect, the cell has been isolated from a subject prior to the contacting step. In a further aspect, contacting is via administration to a subject.

a. Treatment of a Disorder of Uncontrolled Cellular Proliferation

In one aspect, the invention relates to a method for the treatment of a disorder of uncontrolled cellular proliferation in a mammal, the method comprising the step of administering to the mammal an effective amount of least one disclosed compound or a product of a disclosed method of making a compound, or a pharmaceutically acceptable salt, hydrate, solvate, or polymorph thereof, thereby treating the disorder of uncontrolled cellular proliferation.

In a still further aspect, the effective amount is a therapeutically effective amount. In a yet still further aspect, the effective amount is a prophylactically effective amount.

In a further aspect, the mammal is a human. In a yet further aspect, the method further comprises the step of identifying a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the disorder of uncontrolled cellular proliferation is a cancer. In a yet further aspect, the cancer is a leukemia. In an even further aspect, the cancer is a sarcoma. In a still further aspect, the cancer is a solid tumor. In a yet further aspect, the cancer is a lymphoma. In an even further aspect, the cancer is selected from chronic lymphocytic leukemia, small lymphocytic lymphoma, B-cell non-Hodgkin lymphoma, and large B-cell lymphoma. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

EXAMPLES

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

Some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

Experimental Chemistry

Synthesis Schemes, Methods and Procedures

6-Chloro-3H-imidazo[4,5-c]pyridine-2-thiol (Compound 2)

The reaction mixture of 6-chloropyridine-3,4-diamine (100 mg, 0.697 mmol), di(1H-imidazol-1-yl)methanethione (124 mg, 0.697 mmol) in tetrahydrofuran (4 mL, 0.697 mmol) was stirred at RT overnight. The precipitate was filtrated and 6-chloro-3H-imidazo[4,5-c]pyridine-2-thiol (100 mg, 0.539 mmol, 77% yield) was obtained. $^1$HNMR (400 MHz, CD$_3$OD) δ 7.76 (s, 1H), 7.07 (s, 1H), ESI-MS: m/z 185.82 (M+H)$^{30}$

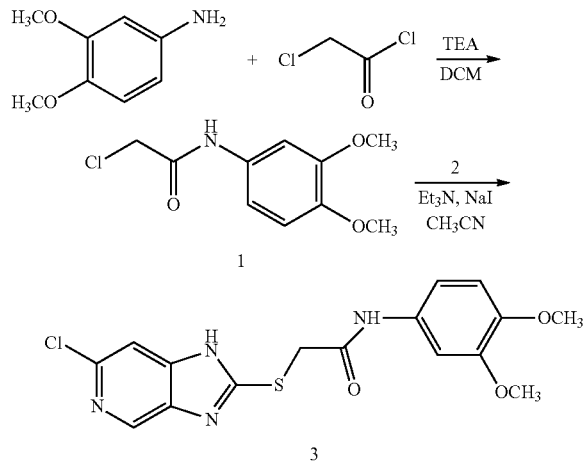

2-Chloro-N-(3,4-dimethoxyphenyl)acetamide (Compound 1)

To the solution of 3,4-dimethoxyaniline (200 mg, 1.306 mmol), TEA (0.546 mL, 3.92 mmol) in DCM (5 mL) was added 2-chloroacetyl chloride (0.125 mL, 1.567 mmol) at room temperature. After 1 hr, concentration and purification on combiflash (4 g, EtOAc/Hexane) gave 2-chloro-N-(3,4-dimethoxyphenyl)acetamide (232 mg, 1.010 mmol, 77% yield). 1HNMR (400 MHz, CDCl3) δ 7.28 (J=2 Hz, 1H), 6.95 (d, J=6 Hz, 1H), 6.85 (d, J=8.8 Hz, 1H), 4.19 (s, 2H) 3.90 (s, 3H), 3.87 (s, 3H).

2-((6-Chloro-3H-imidazo[4,5-c]pyridin-2-yl)thio)-N-(3,4-dimethoxyphenyl)acetamide (Compound 3)

The reaction mixture of 6-chloro-3H-imidazo[4,5-c]pyridine-2-thiol (13 mg, 0.070 mmol), 2-chloro-N-(3,4-dimethoxyphenyl)acetamide (16.08 mg, 0.070 mmol), sodium iodide (1 mg, 6.67 µmol), triethylamine (0.029 mL, 0.210 mmol) in acetonitrile (1 mL) was heated at 65° C. for 1.5 hr. Concentration and purification on combiflash (4 g, MeOH/DCM) gave 2-((6-chloro-3H-imidazo[4,5-c]pyridin-2-yl)thio)-N-(3,4-dimethoxyphenyl)acetamide (13 mg, 0.034 mmol, 49.0% yield). 1HNMR (400 MHz, CDCl$_3$) δ 9.81 (s, 1H), 8.70 (m, 1H), 7.31 (s, 1H), 6.86 (m, 1H), 6.77 (m, 2H), 3.99 (s, 2H), 3.84 (m, 6H). ESI-MS: m/z 379.02 (M+H)+

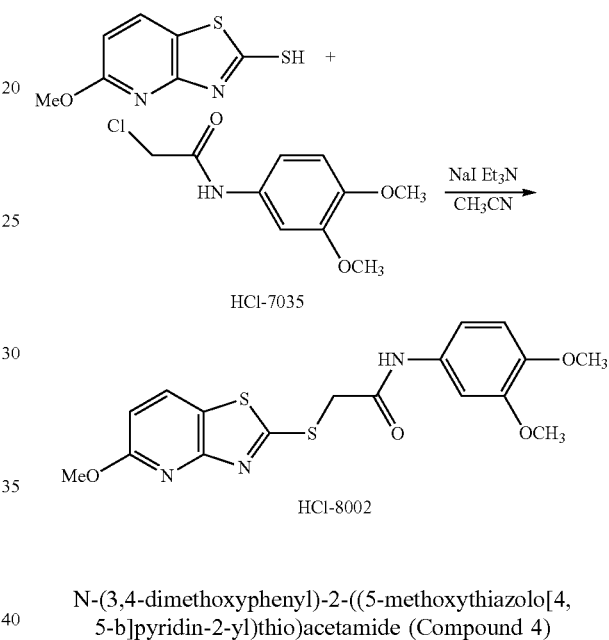

N-(3,4-dimethoxyphenyl)-2-((5-methoxythiazolo[4,5-b]pyridin-2-yl)thio)acetamide (Compound 4)

The reaction mixture of 5-methoxythiazolo[4,5-b]pyridine-2-thiol (17.27 mg, 0.087 mmol), 2-chloro-N-(3,4-dimethoxyphenyl)acetamide (20 mg, 0.087 mmol), sodium iodide (1 mg, 6.67 µmol), triethylamine (0.036 mL, 0.261 mmol) in acetonitrile (1 mL) was heated at 65° C. for 2 hr. Concentration and purification on combiflash (4 g, MeOH/DCM) gave N-(3,4-dimethoxyphenyl)-2-((5-methoxythiazolo[4,5-b]pyridin-2-yl)thio)acetamide (13.5 mg, 0.034 mmol, 39.6% yield) $^1$HNMR (400 MHz, CD$_3$OD), δ 8.01 (d, J=8.8 Hz, 1H), 7.82 (s, 1H), 7.31 (d, J=2 Hz, 1H), 7.02 (d, J=8.8 Hz, 1H), 6.86 (m, 2H), 3.95 (s, 2H), 3.80 (s, 3H), 3.30 (m, 6H). ESI-MS: m/z 392.04 (M+H)$^+$

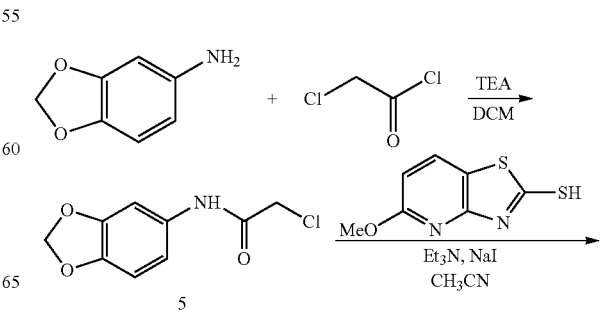

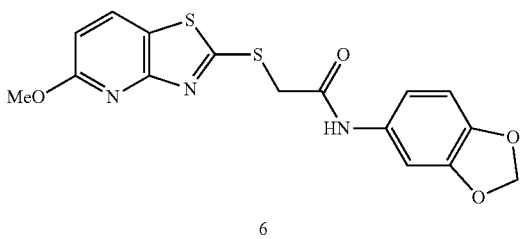

6

N-(benzo[d][1,3]dioxol-5-yl)-2-chloroacetamide (Compound 5)

To the solution of benzo[d][1,3]dioxol-5-amine (200 mg, 1.458 mmol), TEA (0.610 mL, 4.38 mmol) in DCM (5 mL) was added 2-chloroacetyl chloride (0.139 mL, 1.75 mmol) at room temperature. After 1 hr, concentration and purification on combiflash (4 g, EtOAc/Hexane) gave N-(benzo[d][1,3]dioxol-5-yl)-2-chloroacetamide (239 mg, 1.119 mmol, 77% yield).

$^1$HNMR (400 MHz, CDCl$_3$) δ 8.12 (br-s, 1H), 7.23 (s, 1H), 6.85 (d, J=8 Hz, 1H), 6.78 (d, J=8 Hz, 1H), 5.97 (s, 2H), 4.18 (s, 2H) ESI-MS: m/z 213.96 (M+H)$^+$

N-(benzo[d][1,3]dioxol-5-yl)-2-((5-methoxythiazolo[4,5-b]pyridin-2-yl)thio)acetamide (Compound 6)

The reaction mixture of 5-methoxythiazolo[4,5-b]pyridine-2-thiol (18.56 mg, 0.094 mmol), N-(benzo[d][1,3]dioxol-5-yl)-2-chloroacetamide (20 mg, 0.094 mmol), sodium iodide (1 mg, 6.67 µmol), triethylamine (0.039 mL, 0.281 mmol) in Acetonitrile (1 mL) was heated at 65° C. for 1.5 hr. Concentration and purification on combiflash (4 g, MeOH/DCM) gave N-(benzo[d][1,3] dioxol-5-yl)-2-((5-methoxythiazolo[4,5-b]pyridin-2-yl)thio)acetamide (17.8 mg, 0.047 mmol, 50.6% yield) $^1$HNMR (400 MHz, CDCl$_3$) δ 9.63 (s, 1H), 8.01 (d, J=8.8 Hz, 2H), 7.22 (s, 1H), 6.86 (d, J=8.8 Hz, 1H), 6.72 (m, 3H), 5.93 (s, 2H), 4.02 (s, 2H), 3.99 (s, 3H), ESI-MS: m/z 376.0 (M+H)$^+$

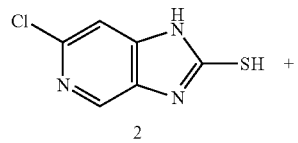

2

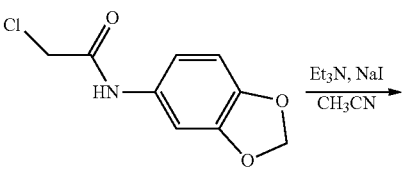

5

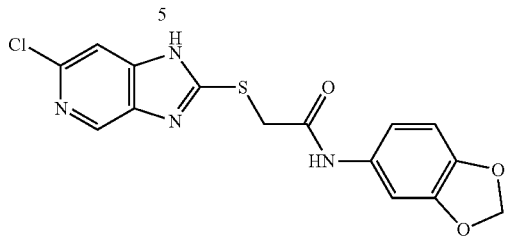

7

N-(benzo[d][1,3]dioxol-5-yl)-2-((6-chloro-1H-imidazo[4,5-c]pyridin-2-yl)thio)acetamide (Compound 7)

The reaction mixture of 6-chloro-1H-imidazo[4,5-c]pyridine-2-thiol (17.38 mg, 0.094 mmol), N-(benzo[d][1,3]dioxol-5-yl)-2-chloroacetamide (20 mg, 0.094 mmol), sodium iodide (1 mg, 6.67 µmol), triethylamine (0.039 mL, 0.281 mmol) in acetonitrile (1 mL) was heated at 65° C. for 1.5 hr. Concentration and purification on combiflash (4 g, MeOH/DCM) gave N-(benzo[d][1,3]dioxol-5-yl)-2-((6-chloro-1H-imidazo[4,5-c]pyridin-2-yl)thio)acetamide (11.8 mg, 0.033 mmol, 34.7% yield). $^1$HNMR (400 MHz, CDCl$_3$) δ 8.44 (s, 1H), 7.34 (s, 1H), 7.13 (s, 1H), 6.75 (d, J=8.4 Hz, 1H), 6.64 (d, J=8.0 Hz 1H), 5.84 (s, 2H), 3.94 (s, 2H), ESI-MS: m/z 362.98 (M+H)$^+$

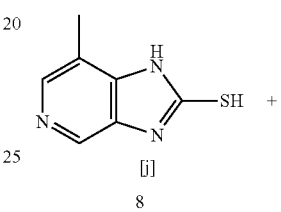

8

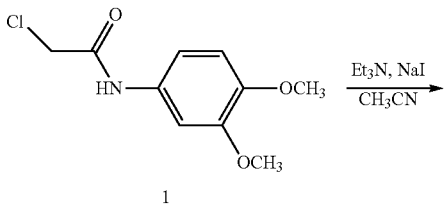

1

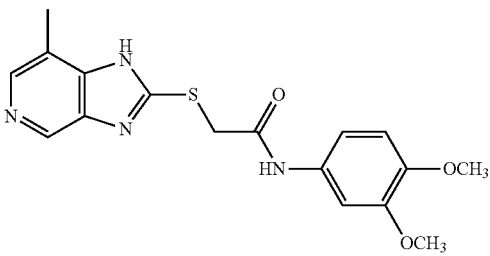

9

N-(3,4-dimethoxyphenyl)-2-((7-methyl-1H-imidazo[4,5-c]pyridin-2-yl)thio)acetamide (Compound 9)

The reaction mixture of 7-methyl-1H-imidazo[4,5-c]pyridine-2-thiol (14.39 mg, 0.087 mmol), 2-chloro-N-(3,4-dimethoxyphenyl)acetamide (20 mg, 0.087 mmol), sodium iodide (1 mg, 6.67 µmol), triethylamine (0.036 mL, 0.261 mmol) in acetonitrile (1 mL) was heated at 65° C. for 2 hr. Concentration and purification on combiflash (4 g, DCM/MeOH) gave N-(3,4-dimethoxyphenyl)-2-((7-methyl-1H-imidazo[4,5-c]pyridin-2-yl)thio)acetamide (33 mg, 0.092 mmol, 100% yield) $^1$HNMR (400 MHz, CDCl$_3$), δ 10.8 (s, 1H), 8.66 (s, 1H), 7.99 (s, 1H), 7.35 (s, 1H), 7.18 (s, 2H), 4.11 (s, 2H), 3.80 (s, 6H), 2.59 (s, 3H). ESI-MS: m/z 359.05 (M+H)$^+$

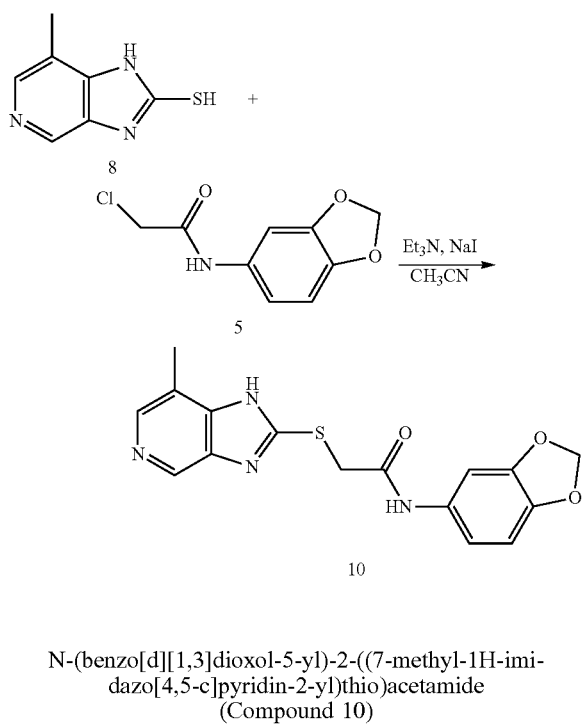

N-(benzo[d][1,3]dioxol-5-yl)-2-((7-methyl-1H-imidazo[4,5-c]pyridin-2-yl)thio)acetamide (Compound 10)

The reaction mixture of 7-methyl-1H-imidazo[4,5-c]pyridine-2-thiol (15.47 mg, 0.094 mmol), N-(benzo[d][1,3]dioxol-5-yl)-2-chloroacetamide (20 mg, 0.094 mmol), sodium iodide (1 mg, 6.67 μmol), triethylamine (0.039 mL, 0.281 mmol) in acetonitrile (1 mL) was heated to 65° C. for 2 hr. Concentration and purification on combiflash (4 g, DCM/MeOH) gave N-(benzo[d][1,3] dioxol-5-yl)-2-((7-methyl-1H-imidazo[4,5-c]pyridin-2-yl)thio)acetamide (33.7 mg, 0.098 mmol, 100% yield) $^1$HNMR (400 MHz, CDCl$_3$) δ 8.01 (m, 2H), 7.09 (m, 3H), 6.69 (m, 1H), 5.88 (s, 2H), 3.94 (s, 2H). 2.52 (s, 3H). ESI-MS: m/z 342.98 (M+H)$^+$

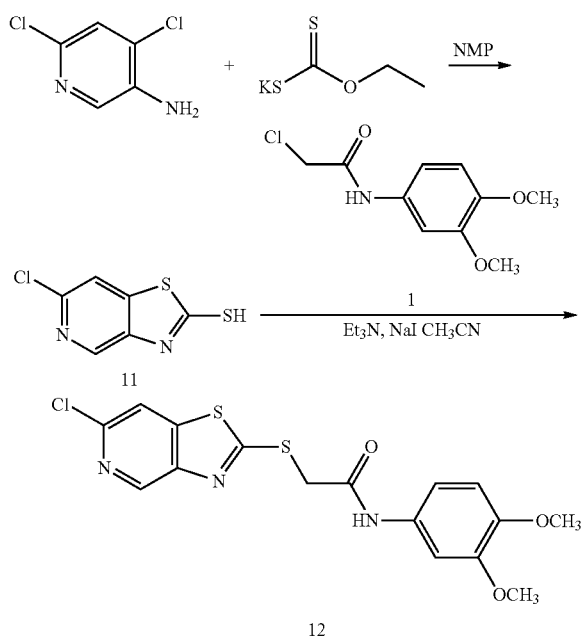

6-Chlorothiazolo[4,5-c]pyridine-2-thiol (Compound 11)

The reaction mixture of 4,6-dichloropyridin-3-amine (50 mg, 0.307 mmol), potassium O-ethyl carbonodithioate (73.8 mg, 0.460 mmol) in NMP (2 mL) was heated to 150° C. overnight. Acetice acid (60 uL) and water were added. Precipitate was filtered and dried to gave 6-chlorothiazolo[4,5-c]pyridine-2-thiol (52 mg, 0.257 mmol, 84% yield) $^1$HNMR (400 MHz, CD$_3$OD) δ 8.35 (s, 1H), 7.44 (s, 1H). ESI-MS: m/z 202.78 (M+H)$^+$

2-((6-Chlorothiazolo[4,5-c]pyridin-2-yl)thio)-N-(3,4-dimethoxyphenyl)acetamide (Compound 12)

The reaction mixture of 6-chlorothiazolo[4,5-c]pyridine-2-thiol (17.65 mg, 0.087 mmol), 2-chloro-N-(3,4-dimethoxyphenyl)acetamide (20 mg, 0.087 mmol), sodium iodide (1 mg, 6.67 μmol), triethylamine (0.036 mL, 0.261 mmol) in acetonitrile (1 mL) was heated at 65° C. for 1.5 hr. Concentration and purification by Prep-TLC (MeOH/DCM) gave 2-((6-chlorothiazolo[4,5-c]pyridin-2-yl)thio)-N-(3,4-dimethoxyphenyl)acetamide (5.7 mg, 0.014 mmol, 16.53% yield)
$^1$HNMR (400 MHz, CDCl$_3$) δ 8.97 (s, 1H), 7.78 (s, 1H), 7.34 (s, 1H), 6.79 (m, 2H), 4.11 (s, 2H), 3.86 (s, 3H), 3.84 (s, 3H). ESI-MS: m/z 395.97 (M+H)$^+$

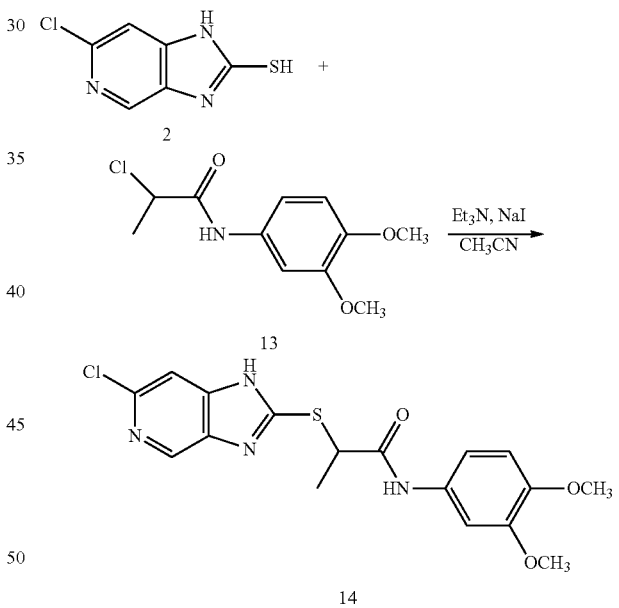

2-((6-Chloro-1H-imidazo[4,5-c]pyridin-2-yl)thio)-N-(3,4-dimethoxyphenyl)propanamide (Compound 14)

The reaction mixture of 6-chloro-1H-imidazo[4,5-c]pyridine-2-thiol (15.24 mg, 0.082 mmol), 2-chloro-N-(3,4-dimethoxyphenyl)propanamide (20 mg, 0.082 mmol), sodium iodide (1 mg, 6.67 μmol), triethylamine (0.034 mL, 0.246 mmol) in acetonitrile (1 mL) was heated at 65° C. overnight. The solid was filtered and dried to give 2-((6-chloro-1H-imidazo[4,5-c]pyridin-2-yl)thio)-N-(3,4-dimethoxyphenyl)propanamide (17 mg, 0.043 mmol, 52.7% yield). ESI-MS: m/z 393.06 (M+H)$^+$

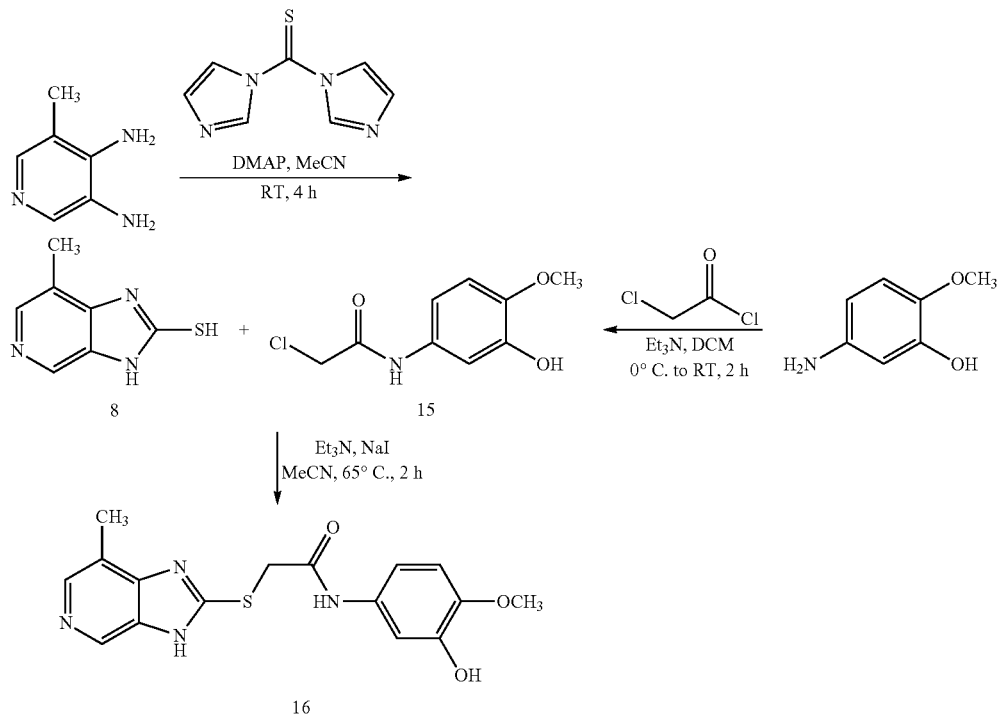

7-Methyl-1,3-dihydro-2H-imidazo[4,5-c]pyridine-2-thione (Compound 8)

To a solution of 5-methylpyridine-3,4-diamine (100 mg, 0.812 mmol) and N,N-dimethylpyridin-4-amine (109 mg, 0.893 mmol) in MeCN was added di(1H-imidazol-1-yl)methanethione (217 mg, 1.218 mmol) portionwise. The mixture was stirred at room temperature for 4 h. The precipitate formed was filtered, washed with water, Et$_2$O, DCM and dried to give 7-methyl-1H-imidazo[4,5-c]pyridine-2 (3H)-thione (100 mg, 75% yield) as a pale red solid. $^1$H-NMR (400 MHz, DMSO-d$_6$) δ ppm 12.73 (brs, 2H), 8.20 (s, 1H), 8.06 (s, 1H), 2.33 (s, 3H); ESI-MS: m/z 165.84 (M+H)$^+$.

2-Chloro-N-(3-hydroxy-4-methoxyphenyl)acetamide (Compound 15)

A solution of 5-amino-2-methoxyphenol (100 mg, 0.719 mmol) and triethylamine (0.150 ml, 1.078 mmol) in DCM was cooled to 0° C. and 2-chloroacetyl chloride (0.060 ml, 0.755 mmol) was added dropwise. The reaction mixture was stirred at room temperature for 2 h. Solvent was removed and the crude was purified by combiflash SiO$_2$ chromatography (0-5% MeOH-DCM) to give 2-chloro-N-(3-hydroxy-4-methoxyphenyl)acetamide (58 mg, 37%) as a brown solid. $^1$H-NMR (400 MHz, CDCl$_3$) δ ppm 8.11 (brs, 1H), 7.14 (d, 1H, J=4 Hz), 7.04 (dd, 1H, J=4 Hz and J=8 Hz), 6.81 (d, 1H, J=12 Hz), 4.18 (s, 2H), 3.88 (s, 3H); ESI-MS: m/z 215.90 (M+H)$^+$.

N-(3-hydroxy-4-methoxyphenyl)-2-((7-methyl-1H-imidazo[4,5-c]pyridin-2-yl)thio)acetamide (Compound 16)

A mixture of 2-chloro-N-(3-hydroxy-4-methoxyphenyl) acetamide (15 mg, 0.070 mmol), 7-methyl-1H-imidazo[4,5-c]pyridine-2 (3H)-thione (12.64 mg, 0.077 mmol), sodium iodide (10.43 mg, 0.070 mmol) and triethylamine (0.015 ml, 0.104 mmol) in MeCN was heated to 65° C. for 2 h. Solvent was removed and the crude was purified by combiflash SiO$_2$ chromatography (0-10% MeOH-DCM) to obtain N-(3-hydroxy-4-methoxyphenyl)-2-((7-methyl-1H-imidazo[4,5-c]pyridin-2-yl)thio)acetamide (11 mg, 46%) as an off-white solid. $^1$H-NMR (400 MHz, CD$_3$OD/CDCl$_3$) δ ppm 8.52 (s, 1H), 7.93 (s, 1H), 7.08 (d, 1H, J=4 Hz), 6.92 (dd, 1H, J=4 Hz, J=8 Hz), 6.77 (d, 1H, J=8 Hz), 4.07 (s, 2H), 3.80 (s, 3H), 2.54 (s, 3H); ESI-MS: m/z 345.03 (M+H)$^+$.

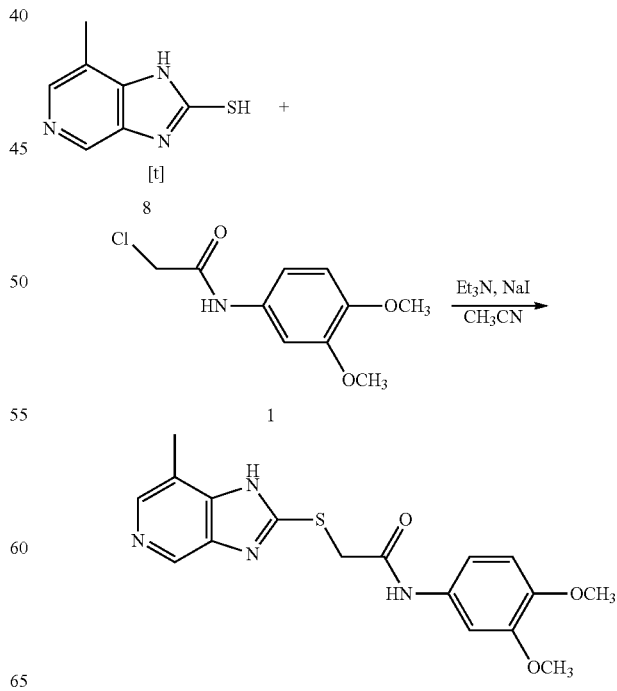

The reaction mixture of 7-methyl-1H-imidazo[4,5-c]pyridine-2-thiol (14.39 mg, 0.087 mmol), 2-chloro-N-(3,4-dimethoxyphenyl)acetamide (20 mg, 0.087 mmol), sodium iodide (1 mg, 6.67 µmol), triethylamine (0.036 mL, 0.261 mmol) in acetonitrile (1 mL) was heated at 65° C. for 2 hr. Concentration and purification on combiflash (4 g, DCM/MeOH) gave N-(3,4-dimethoxyphenyl)-2-((7-methyl-1H-imidazo[4,5-c]pyridin-2-yl)thio)acetamide (33 mg, 0.092 mmol, 100% yield) $^1$HNMR (400 MHz, CDCl$_3$), 10.8 (s, 1H), 8.66 (s, 1H), 7.99 (s, 1H), 7.35 (s, 1H), 7.18 (s, 2H), 4.11 (s, 2H), 3.80 (s, 6H), 2.59 (s, 3H). ESI-MS: m/z 359.05 (M+H)+

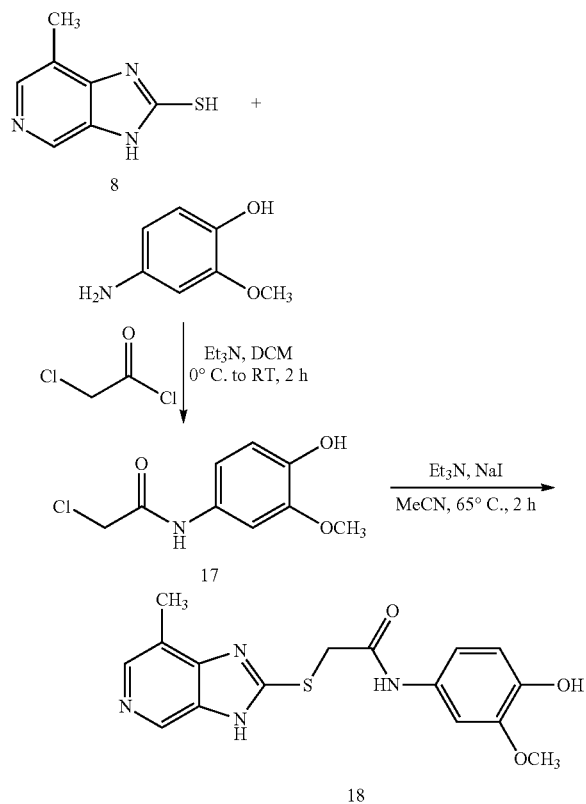

2-Chloro-N-(4-hydroxy-3-methoxyphenyl)acetamide (Compound 17)

A solution of 4-amino-2-methoxyphenol (100 mg, 0.719 mmol) and triethylamine (0.150 ml, 1.078 mmol) in DCM was cooled to 0° C. and 2-chloroacetyl chloride (0.060 ml, 0.755 mmol) was added dropwise. The reaction mixture was stirred at room temperature for 2 h. Solvent was removed and the crude was purified by combiflash SiO$_2$ chromatography (0-5% MeOH-DCM) to give 2-chloro-N-(4-hydroxy-3-methoxyphenyl)acetamide (55 mg, 36% yield) as a brown solid. $^1$H-NMR (400 MHz, CDCl$_3$) δ ppm 8.14 (brs, 1H), 7.38 (d, 1H, J=2.4 Hz), 6.87 (d, 1H, J=8 Hz), 6.80 (dd, 1H, J=4 Hz and J=8 Hz), 4.18 (s, 2H), 3.90 (s, 3H); ESI-MS: m/z 215.90 (M+H)$^+$.

N-(4-hydroxy-3-methoxyphenyl)-2-((7-methyl-3H-imidazo[4,5-c]pyridin-2-yl)thio)acetamide (Compound 18)

A mixture of 7-methyl-1H-imidazo[4,5-c]pyridine-2(3H)-thione (13.79 mg, 0.083 mmol), 2-chloro-N-(4-hydroxy-3-methoxyphenyl)acetamide (15 mg, 0.070 mmol), Sodium iodide (10.43 mg, 0.070 mmol) in MeCN was added triethylamine (0.012 ml, 0.083 mmol) and heated to 65° C. for 1 h. Solvent was removed and the crude was purified by combiflash (0-10% DCM-MeOH) to obtain N-(4-hydroxy-3-methoxyphenyl)-2-((7-methyl-1H-imidazo[4,5-c]pyridin-2-yl)thio)acetamide (14 mg, 58%) as a white solid. $^1$H-NMR (400 MHz, CD$_3$OD/CDCl$_3$) δ ppm 8.51 (s, 1H), 7.91 (s, 1H), 7.27 (d, 1H, J=4 Hz), 6.77 (dd, 1H, J=4 Hz, J=8 Hz), 6.71 (d, 1H, J=8 Hz), 4.06 (s, 2H), 3.80 (s, 3H), 2.53 (s, 3H); ESI-MS: m/z 345.04 (M+H)$^+$.

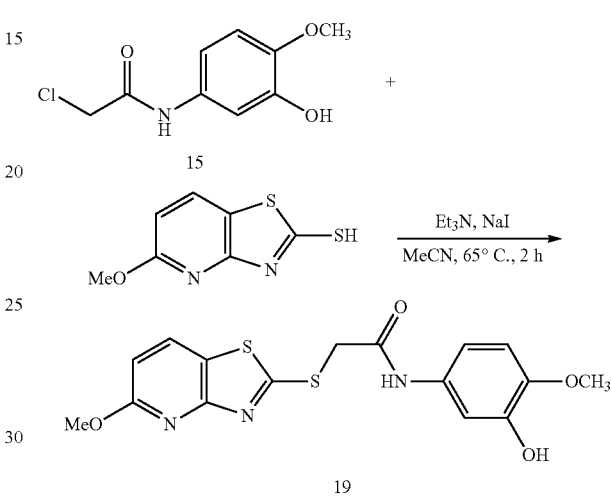

N-(3-hydroxy-4-methoxyphenyl)-2-((5-methoxythiazolo[4,5-b]pyridin-2-yl)thio)acetamide (Compound 19)

To a mixture of 5-methoxythiazolo[4,5-b]pyridine-2-thiol (20 mg, 0.101 mmol), 2-chloro-N-(3-hydroxy-4-methoxyphenyl)acetamide (23.93 mg, 0.111 mmol) and sodium iodide (15.02 mg, 0.101 mmol) in MeCN (1 ml) was added triethylamine (0.021 ml, 0.151 mmol) and stirred at 65° C. for 2 h. Solvent was removed and the crude was combiflash chromatographed using 0-10% MeOH-DCM to obtain N-(3-hydroxy-4-methoxyphenyl)-2-((5-methoxythiazolo[4,5-b]pyridin-2-yl)thio)acetamide (23 mg, 60%) as a pale orange solid. $^1$H-NMR (400 MHz, CD$_3$OD/CDCl$_3$) δ ppm 9.56 (brs, 1H), 7.98 (d, 1H, J=12 Hz), 7.05 (dd, 1H, J=1.2 Hz, J=4 Hz), 6.92 (dd, 1H, J=4 Hz, J=8 Hz), 6.83 (d, 1H, J=8 Hz), 6.74 (d, 1H, J=12 Hz), 4.00 (s, 2H), 3.96 (s, 3H), 3.81 (s, 3H); ESI-MS: m/z 378.02 (M+H)$^+$.

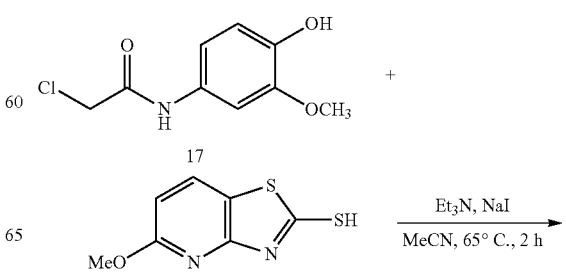

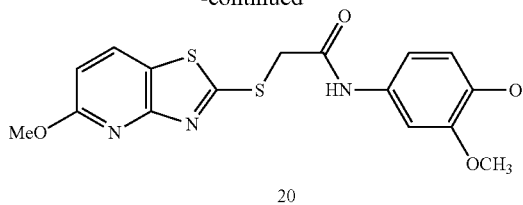

N-(4-hydroxy-3-methoxyphenyl)-2-((5-methoxythiazolo[4,5-b]pyridin-2-yl)thio)acetamide (Compound 20)

To a mixture of 2-chloro-N-(4-hydroxy-3-methoxyphenyl)acetamide (20 mg, 0.093 mmol), 5-methoxythiazolo[4,5-b]pyridine-2-thiol (20.23 mg, 0.102 mmol) and sodium iodide (13.81 mg, 0.093 mmol) in MeCN was added triethylamine (0.019 ml, 0.139 mmol) and stirred at 65° C. for 2 h. Solvent was removed and the crude was chromatographed using 0-10% MeOH-DCM to afford N-(4-hydroxy-3-methoxyphenyl)-2-((5-methoxythiazolo[4,5-b]pyridin-2-yl)thio)acetamide (22 mg, 63%) as a pale orange solid. $^1$H-NMR (400 MHz, CD$_3$OD/CDCl$_3$) δ ppm 7.88 (d, 1H, J=12 Hz), 7.22 (d, 1H, J=2 Hz), 6.73 (d, 1H, J=12 Hz), 6.65 (d, 1H, J=8 Hz), 6.61 (dd, 1H, J=4 Hz, J=8 Hz), 3.97 (s, 2H), 3.85 (s, 3H), 3.72 (s, 3H); ESI-MS: m/z 378.04 (M+H)$^+$.

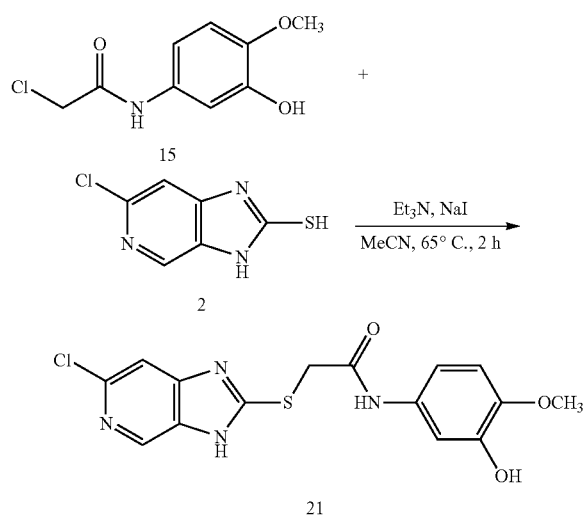

2-((6-chloro-3H-imidazo[4,5-c]pyridin-2-yl)thio)-N-(3-hydroxy-4-methoxyphenyl)acetamide (Compound 21)

A mixture of 2-chloro-N-(3-hydroxy-4-methoxyphenyl)acetamide (15 mg, 0.070 mmol), 6-chloro-3H-imidazo[4,5-c]pyridine-2-thiol (15.50 mg, 0.083 mmol), sodium iodide (10.43 mg, 0.070 mmol) and triethylamine (0.015 ml, 0.104 mmol) in MeCN was heated to 65° C. for 2 h. The crude was subjected to combiflash silica gel chromatography (0-10% MeOH-DCM) to obtain 2-((6-chloro-3H-imidazo[4,5-c]pyridin-2-yl)thio)-N-(3-hydroxy-4-methoxyphenyl)acetamide (15 mg, 59%) as a white solid. 1H-NMR (400 MHz, CD$_3$OD/CDCl$_3$) δ ppm 8.49 (s, 1H), 7.48 (s, 1H), 7.11 (d, 1H, J=2.4 Hz), 6.94 (dd, 1H, J=4 Hz, J=8 Hz), 6.83 (d, 1H, J=8 Hz), 4.18 (s, 2H), 3.81 (s, 3H); ESI-MS: m/z 365.02 (M+H)$^+$.

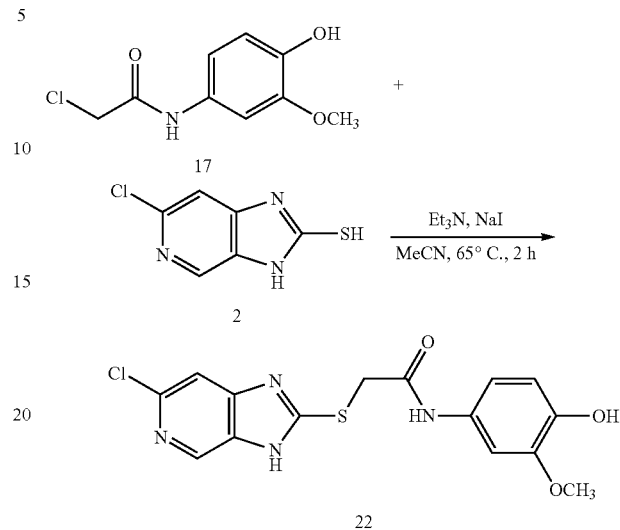

2-((6-chloro-3H-imidazo[4,5-c]pyridin-2-yl)thio)-N-(4-hydroxy-3-methoxyphenyl)acetamide (Compound 20)

A mixture of 2-chloro-N-(4-hydroxy-3-methoxyphenyl)acetamide (17.42 mg, 0.081 mmol), 6-chloro-3H-imidazo[4,5-c]pyridine-2-thiol (15 mg, 0.081 mmol), sodium iodide (12.11 mg, 0.081 mmol) and triethylamine (0.011 ml, 0.081 mmol) in MeCN was heated to 65° C. for 2 h. The crude was purified by combiflash silica gel chromatography (0-10% MeOH-DCM) to afford 2-((6-chloro-3H-imidazo[4,5-c]pyridin-2-yl)thio)-N-(4-hydroxy-3-methoxyphenyl)acetamide (17 mg, 58%) as a white solid. $^1$H-NMR (400 MHz, CD$_3$OD/CDCl$_3$) δ ppm 8.49 (s, 1H), 7.45 (s, 1H), 7.28 (d, 1H, J=2.4 Hz), 6.84 (dd, 1H, J=4 Hz, J=8 Hz), 6.73 (d, 1H, J=8 Hz), 4.15 (s, 2H), 3.81 (s, 3H); ESI-MS: m/z 365.01 (M+H)$^+$.

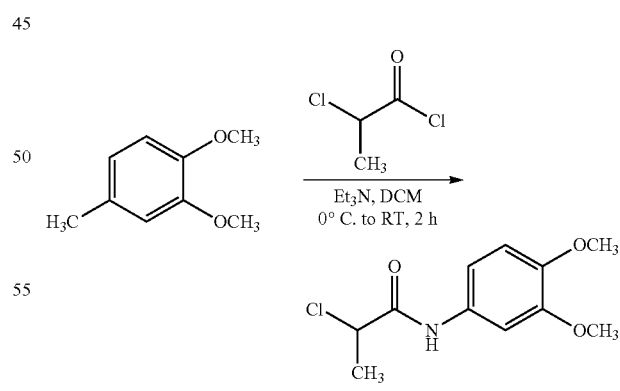

2-chloro-N-(3,4-dimethoxyphenyl)propanamide (Compound 23)

To a cooled solution of 3,4-dimethoxyaniline (100 mg, 0.653 mmol) and triethylamine (0.136 ml, 0.979 mmol) in DCM was added 2-chloropropanoyl chloride (0.076 ml, 0.783 mmol) and stirred at RT for 12 h. Solvent was removed and the crude was purified by combiflash chromatography (0-50% EtOAc-Hexanes) to give 2-chloro-N-(3,4-dimethoxyphenyl)propanamide (140 mg, 88%) as a fluffy white solid. ¹H-NMR (400 MHz, CDCl₃) δ ppm 8.19 (brs, 1H), 7.33 (d, 1H, J=4 Hz), 6.93 (dd, 1H, J=4 Hz, J=8 Hz), 6.83 (d, 1H, J=8 Hz), 4.55 (q, 1H, J=8 Hz), 3.90 (s, 3H), 3.87 (s, 3H), 1.83 (d, 3H, J=8 Hz); ESI-MS: m/z 243.90 (M+H)⁺.

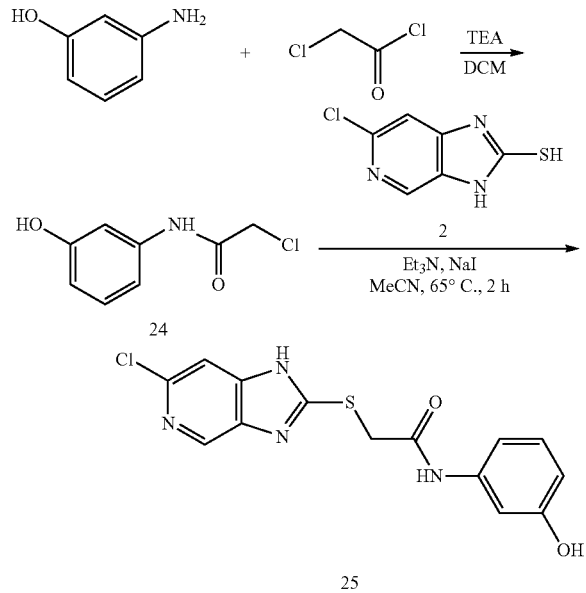

2-((6-Chloro-1H-imidazo[4,5-c]pyridin-2-yl)thio)-N-(3-hydroxyphenyl)acetamide (Compound 25)

The reaction mixture of 6-chloro-1H-imidazo[4,5-c]pyridine-2-thiol (15.00 mg, 0.081 mmol), 2-chloro-N-(3-hydroxyphenyl)acetamide (15 mg, 0.081 mmol), sodium iodide (1 mg, 6.67 μmol), triethylamine (0.034 mL, 0.242 mmol) in acetonitrile (1 mL) was heated at 65° C. for 2 hr. Concentration and purification on combiflash (4 g, MeOH/DCM) gave 2-((6-chloro-1H-imidazo[4,5-c]pyridin-2-yl)thio)-N-(3-hydroxyphenyl)acetamide (5 mg, 0.015 mmol, 18.48% yield)

¹HNMR (400 MHz, CD₃OD) δ 8.49 (s, 1H), 7.47 (s, 1H), 7.13 (m, 2H), 6.96 (s, J=8 Hz, 1H), 6.53 (d, J=8 Hz, 1H), 4.19 (s, 1H), ESI-MS: m/z 334.96 (M+H)⁺

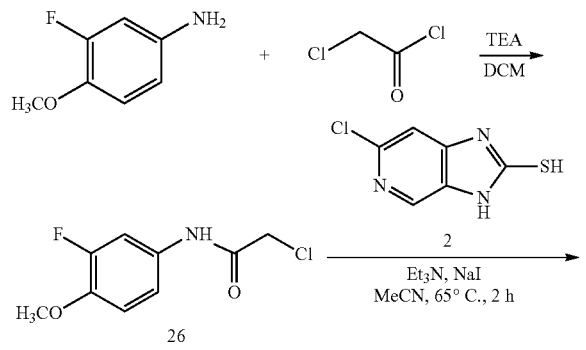

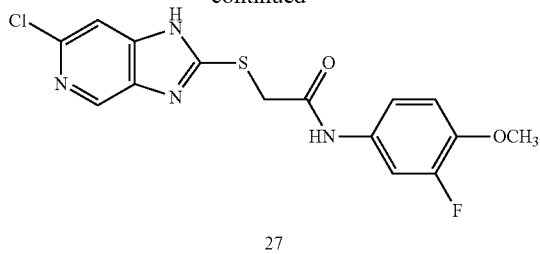

2-Chloro-N-(3-fluoro-4-methoxyphenyl)acetamide (Compound 26)

To the solution of 3-fluoro-4-methoxyaniline (200 mg, 1.417 mmol) and TEA (0.593 mL, 4.25 mmol) in DCM (5 mL) was added 2-chloroacetyl chloride (0.135 mL, 1.700 mmol). After 1 hr, the reaction mixture was concentrated and purified on combiflash (12 g, DCM/MeOH) to give 2-chloro-N-(3-fluoro-4-methoxyphenyl)acetamide (208 mg, 0.956 mmol, 67.5% yield)

¹HNMR (400 MHz, CDCl₃) δ 8.14 (s, 1H), 7.46 (d, J=12.4 Hz, 1H), 7.16 (d, J=8.4 Hz, 1H), 6.93 (m, 1H), 4.18 (s, 2H), 3.88 (s, 3H), ESI-MS: m/z 217.88 (M+H)⁺

2-((6-Chloro-1H-imidazo[4,5-c]pyridin-2-yl)thio)-N-(3-fluoro-4-methoxyphenyl)acetamide (Compound 27)

The reaction mixture of 6-chloro-1H-imidazo[4,5-c]pyridine-2-thiol (17.06 mg, 0.092 mmol), 2-chloro-N-(3-fluoro-4-methoxyphenyl)acetamide (20 mg, 0.092 mmol), sodium iodide (1 mg, 6.67 μmol), triethylamine (0.038 mL, 0.276 mmol) in CH₃CN was heated at 65° C. for 2 hr. Concentration and purification on combiflash (4 g, MeOH/DCM) gave 2-((6-chloro-1H-imidazo[4,5-c]pyridin-2-yl)thio)-N-(3-fluoro-4-methoxyphenyl)acetamide (16 mg, 0.044 mmol, 47.5% yield) ¹HNMR (400 MHz, CD₃OD) δ 8.50 (s, 1H), 7.48 (m, 2H), 7.18 (d, J=8 Hz, 1H), 7.03 (t, J=8.8 Hz, 1H), 4.22 (s, 2H), 3.84 (s, 3H), ESI-MS: m/z 366.97 (M+H)⁺

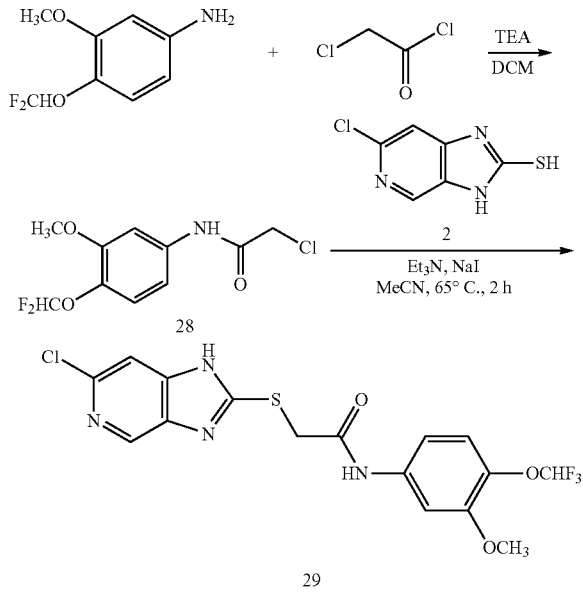

2-Chloro-N-(4-(difluoromethoxy)-3-methoxyphenyl) acetamide (Compound 28)

To the the reaction mixture of 4-(difluoromethoxy)-3-methoxyaniline (150 mg, 0.793 mmol), TEA (0.334 mL, 2.379 mmol) in DCM (4 mL) was added 2-chloroacetyl chloride (0.076 mL, 0.952 mmol) dropwise. After 1 hr at rt, the mixture was concentrated and purified on combiflash (12 g, DCM/MeOH) gave 2-chloro-N-(4-(difluoromethoxy)-3-methoxyphenyl)acetamide (134 mg, 0.504 mmol, 63.6% yield) $^1$HNMR (400 MHz, CDCl$_3$) δ 8.23 (s, 1H), 7.51 (s, 1H), 7.13 (d, J=8.4 Hz, 1H), 6.92 (m, 1H), 6.7, 6.51 (d, J=75 Hz, 1H), 4.2 (s, 2H), 3.89 (s, 3H). ESI-MS: m/z, 265.92 (M+H)$^+$

2-((6-Chloro-1H-imidazo[4,5-c]pyridin-2-yl)thio)-N-(4-(difluoromethoxy)-3-methoxyphenyl)acetamide (Compound 29)

The reaction mixture of 6-chloro-1H-imidazo[4,5-c]pyridine-2-thiol (13.98 mg, 0.075 mmol), 2-chloro-N-(4-(difluoromethoxy)-3-methoxyphenyl)acetamide (20 mg, 0.075 mmol), sodium iodide (11.29 mg, 0.075 mmol), triethylamine (0.031 mL, 0.226 mmol) in acetonitrile (1 mL) was heated to 65° C. for 2 hr. Concentration and purification by combiflash (4 g, DCM/MeOH) gave 2-((6-chloro-1H-imidazo[4,5-c]pyridin-2-yl)thio)-N-(4-(difluoromethoxy)-3-methoxyphenyl)acetamide (24 mg, 0.058 mmol, 77% yield) $^1$HNMR (400 MHz, CDCl$_3$) δ 8.50 (s, 1H), 7.56 (s, 1H), 7.38 (s, 1H), 7.02 (d, J=8.4 Hz, 1H), 6.81 (d, J=8.4 Hz, 1H), 6.43 (t, J=76 Hz, 1H), 3.99 (s, 1H), 3.80 (s, 1H) ESI-MS: m/z 414.97 (M+H)$^+$

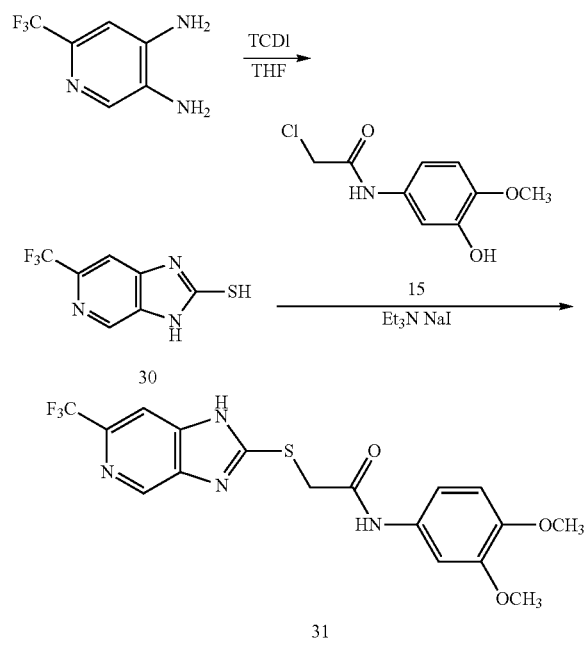

6-(Trifluoromethyl)-3H-imidazo[4,5-c]pyridine-2-thiol (Compound 30)

The reaction mixture of 6-(trifluoromethyl)pyridine-3,4-diamine (100 mg, 0.565 mmol), di(1H-imidazol-1-yl)methanethione (101 mg, 0.565 mmol) in tetrahydrofuran (4 mL, 0.565 mmol). Overnight, precipitate was filtered and 6-(trifluoromethyl)-3H-imidazo[4,5-c]pyridine-2-thiol (70 mg, 0.319 mmol, 56.6% yield) was obtained. $^1$HNMR (400 MHz, CDCl$_3$—CD$_3$OD) δ 8.36 (s, 1H), 7.42 (s, 1H), ESI: m/z 219.8 (M+H)$^+$

N-(3-hydroxy-4-methoxyphenyl)-2-((6-(trifluoromethyl)-1H-imidazo[4,5-c]pyridin-2-yl)thio)acetamide (Compound 31)

The reaction mixture of 6-(trifluoromethyl)-1H-imidazo[4,5-c]pyridine-2-thiol (15.25 mg, 0.070 mmol), 2-chloro-N-(3-hydroxy-4-methoxyphenyl)acetamide (15 mg, 0.070 mmol), sodium iodide (10.43 mg, 0.070 mmol), triethylamine (0.029 mL, 0.209 mmol) in acetonitrile (1 mL) was heated to 65° C. for 2 hr. Concentration and purification by combiflash (4 g, DCM/MeOH) gave N-(3-hydroxy-4-methoxyphenyl)-2-((6-(trifluoromethyl)-1H-imidazo[4,5-c]pyridin-2-yl)thio)acetamide (24 mg, 0.060 mmol, 87% yield) $^1$HNMR (400 MHz, CDCl$_3$) δ 9.03 (s, 1H), 8.00 (s, 1H), 7.50 (d, J=8.4 Hz, 1H), 7.29 (s, 1H), 7.14 (s, 1H), 6.96 (s, 1H), 4.22 (s, 2H), 4.03 (m, 3H). ESI-MS: m/z 399.06 (M+H)$^+$

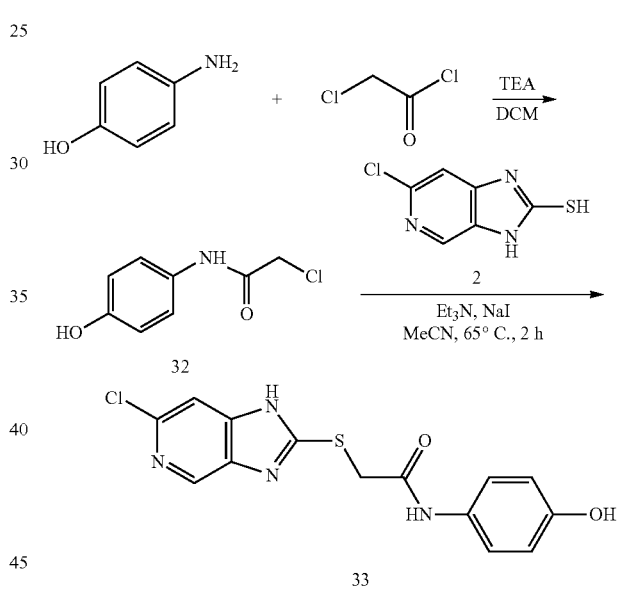

2-chloro-N-(4-hydroxyphenyl)acetamide (Compound 32)

To the the reaction mixture of 4-aminophenol (200 mg, 1.833 mmol), TEA (0.772 mL, 5.50 mmol) in DCM (4 mL) was added 2-chloroacetyl chloride (0.146 mL, 1.833 mmol) dropwise. After 1 hr at rt, the mixture was concentrated and purified on combiflash (12 g, DCM/MeOH) gave 2-chloro-N-(4-hydroxyphenyl)acetamide (134 mg, 0.722 mmol, 39.4% yield) $^1$HNMR (400 MHz, CDCl$_3$) δ 7.32 (d, J=8.8 Hz, 2H), 7.79 (d, J=8.4 Hz, 2H), 4.15 (s, 2H) ESI-MS: m/z 185.84 (M+H)+

2-((6-chloro-1H-imidazo[4,5-c]pyridin-2-yl)thio)-N-(4-hydroxyphenyl)acetamide (Compound 33)

The reaction mixture of 6-chloro-1H-imidazo[4,5-c]pyridine-2-thiol (15.00 mg, 0.081 mmol), 2-chloro-N-(4-hydroxyphenyl)acetamide (15 mg, 0.081 mmol), sodium iodide (12.11 mg, 0.081 mmol), triethylamine (0.034 mL, 0.242 mmol) in Acetonitrile (1 mL) was heated to 65° C. for 2 hr. Concentration and purification by combiflash (4 g, DCM/MeOH) gave 2-((6-chloro-1H-imidazo[4,5-c]pyridin-2-yl)thio)-N-(4-hydroxyphenyl)acetamide (24 mg, 0.072 mmol, 89% yield) $^1$HNMR (400 MHz, CD$_3$OD) δ 8.48 (s, 1H), 7.38 (s, 1H), 7.30 (d, J=8.8 Hz, 2H) 7.19 (s, 1H), 6.71 (d, J=8.8 Hz, 2H), 3.98 (s, 2H), ESI-MS: m/z 334.99 (M+H)$^+$

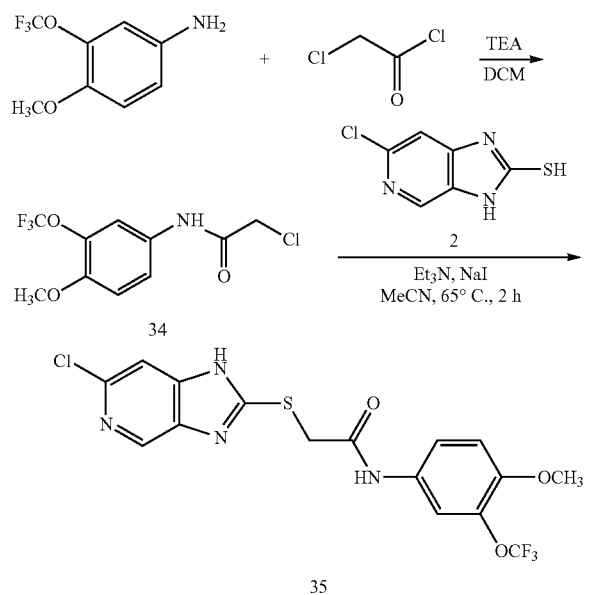

2-chloro-N-(4-methoxy-3-(trifluoromethoxy)phenyl)acetamide (Compound 34)

To the the reaction mixture of 4-methoxy-3-(trifluoromethoxy)aniline (200 mg, 0.965 mmol), TEA (0.407 mL, 2.90 mmol) in DCM (4 mL) was added 2-chloroacetyl chloride (0.092 mL, 1.159 mmol) dropwise. After 1 hr at rt, the mixture was concentrated and purified on combiflash (12 g, DCM/MeOH) gave 2-chloro-N-(4-methoxy-3-(trifluoromethoxy)phenyl)acetamide (212 mg, 0.747 mmol, 77% yield) $^1$HNMR (400 MHz, CDCl$_3$) δ 8.16 (s, 1H), 7.51 (s, 1H), 7.43 (d, J=6.4 Hz, 1H), 6.97 (d, J=8.8 Hz, 1H) 4.19 (s, 2H), 3.88 (s, 3H). ESI-MS: m/z 283.87 (M+H)$^+$

2-((6-chloro-1H-imidazo[4,5-c]pyridin-2-yl)thio)-N-(4-methoxy-3-(trifluoromethoxy)phenyl)acetamide (Compound 35)

The reaction mixture of 6-chloro-1H-imidazo[4,5-c]pyridine-2-thiol (9.82 mg, 0.053 mmol), 2-chloro-N-(4-methoxy-3-(trifluoromethoxy)phenyl)acetamide (15 mg, 0.053 mmol), sodium iodide (7.93 mg, 0.053 mmol), triethylamine (0.022 mL, 0.159 mmol) in acetonitrile (1 mL) was heated to 65° C. for 2 hr. Concentration and purification by combiflash (4 g, DCM/MeOH) gave 2-((6-chloro-1H-imidazo[4,5-c]pyridin-2-yl)thio)-N-(4-methoxy-3-(trifluoromethoxy)phenyl)acetamide (25 mg, 0.058 mmol, 100% yield) $^1$HNMR (400 MHz, CD$_3$OD) δ 8.50 (s, 1H), 7.65 (s, 1H), 7.49 (s, 1H), 7.43 (d, J=6.8 Hz, 1H), 7.10 (d, J=8.8 Hz, 1H), 4.23 (s, 2H), 3.85 (s, ESI-MS: m/z 432.97 (M+H)$^+$

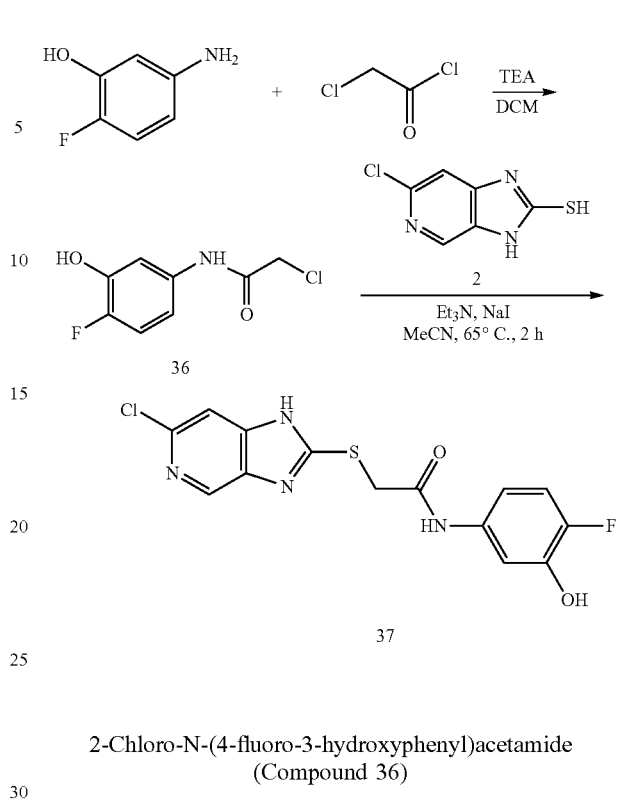

2-Chloro-N-(4-fluoro-3-hydroxyphenyl)acetamide (Compound 36)

To the the reaction mixture of 5-amino-2-fluorophenol (200 mg, 1.573 mmol), TEA (0.663 mL, 4.72 mmol) in DCM (4 mL) was added 2-chloroacetyl chloride (0.125 mL, 1.573 mmol) dropwise. After 1 hr at rt, the mixture was concentrated and purified on combiflash (12 g, DCM/MeOH) gave 2-chloro-N-(4-fluoro-3-hydroxyphenyl)acetamide (169 mg, 0.830 mmol, 52.8% yield) $^1$HNMR (400 MHz, CD$_3$OD) δ 7.22 (m, 1H), 6.93 (m, 1H), 6.83 (m, 1H), 4.07 (s, 2H) ESI-MS: m/z 203.79 (M+H)$^+$

2-((6-chloro-1H-imidazo[4,5-c]pyridin-2-yl)thio)-N-(4-fluoro-3-hydroxyphenyl)acetamide (Compound 37)

The reaction mixture of 6-chloro-1H-imidazo[4,5-c]pyridine-2-thiol (13.68 mg, 0.074 mmol), 2-chloro-N-(4-fluoro-3-hydroxyphenyl)acetamide (15 mg, 0.074 mmol), sodium iodide (11.04 mg, 0.074 mmol), triethylamine (0.031 mL, 0.221 mmol) in acetonitrile (1 mL) was heated to 65° C. for 2 hr. Concentration and purification by combiflash (4 g, DCM/MeOH) gave 2-((6-chloro-1H-imidazo[4,5-c]pyridin-2-yl)thio)-N-(4-fluoro-3-hydroxyphenyl)acetamide (24 mg, 0.068 mmol, 92% yield) $^1$HNMR (400 MHz, CD$_3$OD) δ 8.50 (s, 1H), 7.5 (s, 1H), 7.28 (m, 1H) 6.95 (m, 2H), 4.21 (s, 2H). ESI-MS: m/z 352.93 (M+H)$^+$

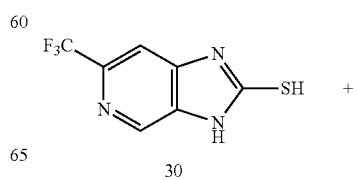

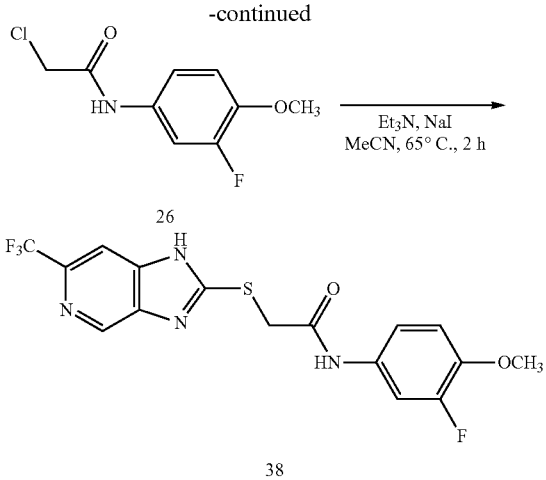

N-(3-fluoro-4-methoxyphenyl)-2-((6-(trifluoromethyl)-1H-imidazo[4,5-c]pyridin-2-yl)thio)acetamide (Compound 38)

The reaction mixture of 6-(trifluoromethyl)-1H-imidazo[4,5-c]pyridine-2-thiol (15.11 mg, 0.069 mmol), 2-chloro-N-(3-fluoro-4-methoxyphenyl)acetamide (15 mg, 0.069 mmol), sodium iodide (1 mg, 6.67 μmol), triethylamine (0.029 mL, 0.207 mmol) in acetonitrile (1 mL) was heated to 65° C. for 2 hr. Concentration and purification by combiflash (4 g, DCM/MeOH) gave N-(3-fluoro-4-methoxyphenyl)-2-((6-(trifluoromethyl)-1H-imidazo[4,5-c]pyridin-2-yl)thio)acetamide (23 mg, 0.057 mmol, 83% yield) 1HNMR (400 MHz, CD$_3$OD) δ 8.81 (s, 1H), 7.89 (s, 1H), 7.51 (m, 1H), 7.20 (m, 1H), 7.02 (t, J=8.8 Hz, 1H), 4.26 (s, 2H), 3.33 (s, 3H). ESI-MS: m/z 400.99 (M+H)$^+$

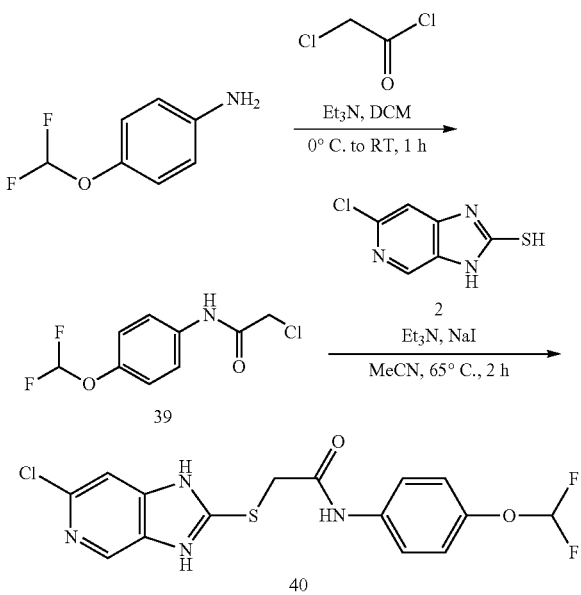

2-Chloro-N-(4-(difluoromethoxy)phenyl)acetamide (Compound 39)

To a solution of 4-(difluoromethoxy)aniline (0.078 ml, 0.628 mmol) and Triethylamine (0.131 ml, 0.943 mmol) in DCM at 0° C., was added 2-chloroacetyl chloride (0.060 ml, 0.754 mmol). The mixture was stirred at RT for 2 h. Solvent was removed and the crude was purified by combiflash chromatography (0-30% EtOAc-Hexanes) to afford 2-chloro-N-(4-(difluoromethoxy)phenyl)acetamide (110 mg, 0.467 mmol, 74.3% yield) as a pale orange solid. $^1$H-NMR (400 MHz, CDCl$_3$) δ ppm 8.24 (brs, 1H), 7.55 (dd, 2H, J=2 Hz, J=4 Hz), 7.13 (d, 2H, J=8 Hz), 6.48 (t, 1H, J=71.5 Hz), 4.20 (s, 2H); ESI-MS: m/z 235.86 (M+H)$^+$.

2-((6-Chloro-3H-imidazo[4,5-c]pyridin-2-yl)thio)-N-(4-(difluoromethoxy)phenyl)acetamide (Compound 40)

To a mixture of 2-chloro-N-(4-(difluoromethoxy)phenyl)acetamide (15 mg, 0.064 mmol), 6-chloro-3H-imidazo[4,5-c]pyridine-2-thiol (13.00 mg, 0.070 mmol) and sodium iodide (9.55 mg, 0.064 mmol) in MeCN was added triethylamine (0.013 ml, 0.095 mmol) and the mixture was stirred at 65° C. for 2 h. Solvents removed and the crude was purified by combiflash SiO$_2$ chromatography (0-100% EtOAc-hexanes) to give 2-((6-chloro-3H-imidazo[4,5-c]pyridin-2-yl)thio)-N-(4-(difluoromethoxy)phenyl)acetamide (21 mg, 0.055 mmol, 86% yield) as a white solid. $^1$H-NMR (400 MHz, CD$_3$OD-CDCl$_3$) δ ppm 8.48 (s, 1H), 7.52 (d, 2H, J=8 Hz), 7.42 (s, 1H), 7.05 (d, 1H, J=8 Hz), 6.53 (t, 1H, J=76 Hz), 4.12 (s, 2H); ESI-MS: m/z 384.97 (M+H)$^+$.

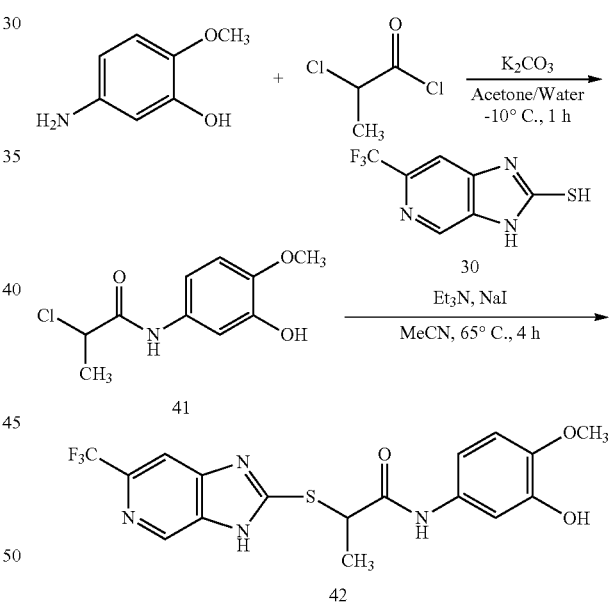

2-Chloro-N-(3-hydroxy-4-methoxyphenyl)propanamide (Compound 41)

A solution of 5-amino-2-methoxyphenol (100 mg, 0.719 mmol) and potassium carbonate (109 mg, 0.791 mmol) in acetone/water was cooled and added 2-chloropropanoyl chloride (0.084 ml, 0.862 mmol). The mixture was stirred at −10° C. for 1 h. The reaction was diluted with EtOAc, washed with 0.5 M HCl, water, brine and dried over anhydrous Na$_2$SO$_4$. Solvent was removed and the crude brown solid, 2-chloro-N-(3-hydroxy-4-methoxyphenyl)propanamide (130 mg, 0.566 mmol, 79% yield), was used in next without purification. 1H-NMR (400 MHz, CDCl$_3$) δ ppm 7.09 (d, 1H, J=2.4 Hz), 6.96 (dd, 1H, J=2.4 Hz and J=8.8 Hz), 6.77 (d, 1H, J=8.8 Hz), 4.47 (q, 1H, J=6.8 Hz), 3.81 (s, 3H), 1.68 (d, 3H, J=6.8 Hz); ESI-MS: m/z 229.89 (M+H)+.

N-(3-Hydroxy-4-methoxyphenyl)-2-((6-(trifluoromethyl)-3H-imidazo[4,5-c]pyridin-2-yl)thio)propanamide (Compound 42)

A mixture of 2-chloro-N-(3-hydroxy-4-methoxyphenyl)propanamide (12 mg, 0.052 mmol), 6-(trifluoromethyl)-3H-imidazo[4,5-c]pyridine-2-thiol (13.74 mg, 0.063 mmol), sodium iodide (3.92 mg, 0.026 mmol) and triethylamine (10.92 µl, 0.078 mmol) in acetonitrile (1 ml) was stirred at 65° C. for 4 h. Solvent was removed and the crude was purified by combiflash chromatography (0-5% MeOH-DCM) to obtain N-(3-hydroxy-4-methoxyphenyl)-2-((6-(trifluoromethyl)-3H-imidazo[4,5-c]pyridin-2-yl)thio)propanamide (10 mg, 0.024 mmol, 46.4% yield) as an orange solid. (400 MHz, CD3OD) δ ppm 8.84 (s, 1H), 7.91 (s, 1H), 7.12 (d, 1H, J=2.4 Hz), 6.94 (dd, 1H, J=2.4 Hz, J=8.8 Hz), 6.84 (d, 1H, J=8.4 Hz), 4.78 (q, 1H, J=7.2), 3.81 (s, 3H), 1.72 (d, 3H, J=7.2 Hz); ESI-MS: m/z 413.02 (M+H)+.

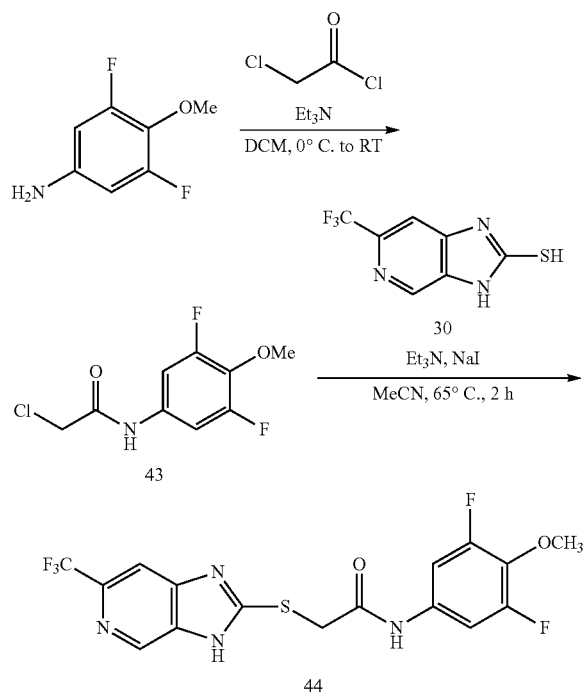

2-Chloro-N-(3,5-difluoro-4-methoxyphenyl)acetamide (Compound 43)

A solution of 3,5-difluoro-4-methoxyaniline (100 mg, 0.628 mmol) and triethylamine (131 µl, 0.943 mmol) in DCM was coiled and added 2-chloroacetyl chloride (60.0 µl, 0.754 mmol). The reaction mixture was stirred at room temperature for 2 h. Reaction was diluted with DCM, washed with 0.5 M HCl, water, brine, dried over Na2SO4 and evaporated. The crude brown solid, 2-chloro-N-(3,5-difluoro-4-methoxyphenyl)acetamide (120 mg, 0.509 mmol, 81% yield) was used for the next step without purification. 1H-NMR (400 MHz, CDCl3) δ ppm 8.15 (s, 1H), 7.21 (d, 1H, J=8 Hz), 4.18 (s, 1H), 3.97 (s, 3H); ESI-MS: m/z 235.82 (M+H)+.

N-(3,5-Difluoro-4-methoxyphenyl)-2-((6-(trifluoromethyl)-3H-imidazo[4,5-c]pyridin-2-yl)thio)acetamide (Compound 44)

A mixture of 2-chloro-N-(3,5-difluoro-4-methoxyphenyl)acetamide (14.19 mg, 0.060 mmol), 6-(trifluoromethyl)-3H-imidazo[4,5-c]pyridine-2-thiol (12 mg, 0.055 mmol), sodium iodide (4.10 mg, 0.027 mmol) and triethylamine (0.011 ml, 0.082 mmol) in MeCN was stirred at 65° C. for 1 h. The crude was purified by combiflash chromatography (0-100% EtOAc-hexanes) to give N-(3,5-difluoro-4-methoxyphenyl)-2-((6-(trifluoromethyl)-3H-imidazo[4,5-c]pyridin-2-yl)thio)acetamide (20 mg, 0.048 mmol, 87% yield) as a white solid. 1H-NMR (400 MHz, CD3OD) δ ppm 8.81 (s, 1H), 7.89 (s, 1H), 7.27 (d, 2H, J=8 Hz), 4.27 (s, 2H), 3.89 (s, 3H); ESI-MS: m/z 419.00 (M+H)+.

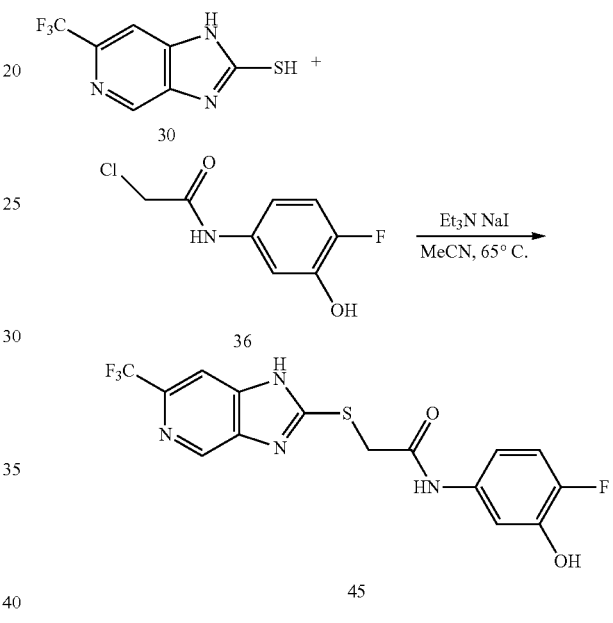

N-(4-fluoro-3-hydroxyphenyl)-2-((6-(trifluoromethyl)-1H-imidazo[4,5-c]pyridin-2-yl)thio)acetamide (Compound 45)

The reaction mixture of 6-(trifluoromethyl)-1H-imidazo[4,5-c]pyridine-2-thiol (12 mg, 0.055 mmol), 2-chloro-N-(4-fluoro-3-hydroxyphenyl)acetamide (12.26 mg, 0.060 mmol), sodium iodide (8.21 mg, 0.055 mmol), triethylamine (0.023 mL, 0.164 mmol) in acetonitrile (1 mL) was heated to 65° C. for 2 hr. Concentration and purification by combiflash (4 g, DCM/MeOH) gave N-(4-fluoro-3-hydroxyphenyl)-2-((6-(trifluoromethyl)-1H-imidazo[4,5-c]pyridin-2-yl)thio)acetamide (15 mg, 0.039 mmol, 70.9% yield). 1HNMR (400 MHz, CD3OD) δ 8.82 (s, 1H), 7.90 (s, 1H), 7.28 (dd, J1=2.4 Hz, J2=8 Hz, 1H), 6.94 (m, 2H), 4.25 (s, 2H), ESI-MS: m/z 387.03 (M+H)+

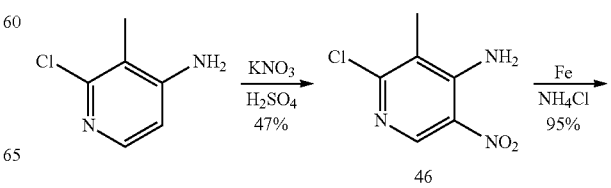

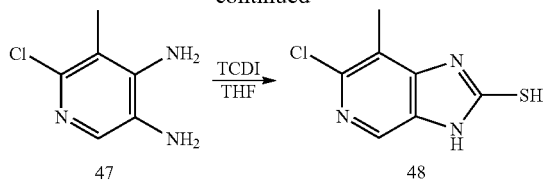

2-Chloro-3-methyl-5-nitropyridin-4-amine (Compound 46)

To the solution of 2-chloro-3-methylpyridin-4-amine (250 mg, 1.753 mmol) in sulfuric acid (2.63 mL, 49.3 mmol) was added potassium nitroperoxous acid (355 mg, 3.51 mmol) at 0° C. The mixture was warmed to room temperature and keep stirred overnight. the mixture was poured into ice water and extracted with EtOAc. The organic layer was dried against MgSO$_4$ and concentrated. Purification on combiflash (12 g, hexane/EtOAc) gave 2-chloro-3-methyl-5-nitropyridin-4-amine (157 mg, 0.837 mmol, 47.7% yield) $^1$HNMR (400 MHz, CDCl$_3$), δ 8.96 (s, 1H), 2.32 (s, 3H) ESI-MS: m/z 187.84 (M+H)$^+$

6-Chloro-5-methylpyridine-3,4-diamine (Compound 47)

The reaction mixture of 2-chloro-3-methyl-5-nitropyridin-4-amine (10 mg, 0.053 mmol), iron (14.89 mg, 0.267 mmol), NH$_4$Cl (14.26 mg, 0.267 mmol) in water (0.5 mL) and ethanol (0.5 mL) was heated to 70° C. for 1.5 hr. Purification by prep-TLC (hexane/EtOAc) gave 6-chloro-5-methylpyridine-3,4-diamine (8 mg, 0.051 mmol, 95% yield). $^1$HNMR (400 MHz, CDCl$_3$) δ 7.644 (s, 1H), 2.22 (s, 3H) ESI-MS: m/z 157.83 (M+H)$^+$

6-Chloro-7-methyl-3H-imidazo[4,5-c]pyridine-2-thiol (Compound 48)

The reaction mixture of 6-chloro-5-methylpyridine-3,4-diamine (8 mg, 0.051 mmol), di(1H-imidazol-1-yl)methanethione (9.05 mg, 0.051 mmol) in tetrahydrofuran (0.5 mL, 0.051 mmol). Overnight. prep-TLC gave 6-chloro-7-methyl-3H-imidazo[4,5-c]pyridine-2-thiol (6 mg, 0.030 mmol, 59.2% yield) $^1$HNMR (400 MHz, CD$_3$OD) δ 7.996 (s, 1H). 2.44 (s, 3H) ESI-MS: m/z 199.79 (M+H)$^+$

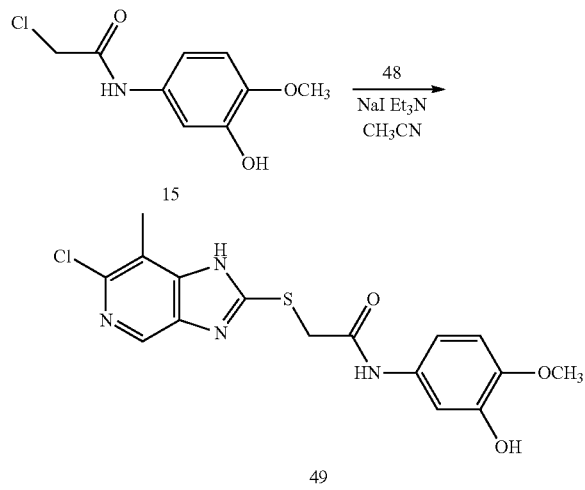

2-((6-Chloro-7-methyl-1H-imidazo[4,5-c]pyridin-2-yl)thio)-N-(3-hydroxy-4-methoxyphenyl)acetamide (Compound 49)

The reaction mixture of 6-chloro-7-methyl-1H-imidazo[4,5-c]pyridine-2-thiol (6 mg, 0.030 mmol), 2-chloro-N-(3-hydroxy-4-methoxyphenyl)acetamide (6.48 mg, 0.030 mmol), sodium iodide (1 mg, 6.67 μmol), triethylamine (0.013 mL, 0.090 mmol) in Acetonitrile (1 mL) was heated to 65° C. for 2 hr. Concentration and purification by prep-TLC (10%, DCM/MeOH) gave 2-((6-chloro-7-methyl-1H-imidazo[4,5-c]pyridin-2-yl)thio)-N-(3-hydroxy-4-methoxyphenyl)acetamide (7 mg, 0.018 mmol, 61.5% yield) $^1$HNMR (400 MHz, CD$_3$OD) δ 8.36 (s, 1H), 7.11 (d, J=2 Hz, 1H), 6.95 (dd, J$_1$=2 Hz, J$_2$=8.8 Hz, 1H), 6.84 (8.8 Hz, 1H), 4.19 (s, 2H), 3.011 (s, 3H), 2.54 (s, 3H). ESI-MS: m/z 379.00 (M+H)$^+$

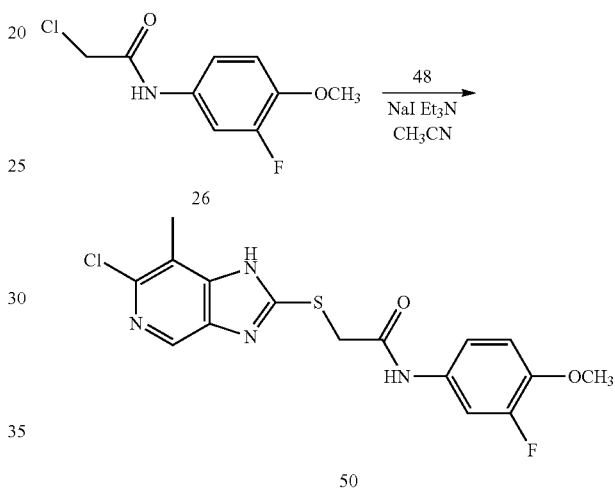

2-((6-Chloro-7-methyl-1H-imidazo[4,5-c]pyridin-2-yl)thio)-N-(3-fluoro-4-methoxyphenyl)acetamide (Compound 50)

The reaction mixture of 6-chloro-7-methyl-1H-imidazo[4,5-c]pyridine-2-thiol (10 mg, 0.050 mmol), 2-chloro-N-(3-fluoro-4-methoxyphenyl)acetamide (10.90 mg, 0.050 mmol), sodium iodide (1 mg, 6.67 μmol), triethylamine (0.021 mL, 0.150 mmol) in acetonitrile (1 mL) was heated at 65° C. for 2 hr. Concentration and purification on prep-TLC (15%, MeOH/DCM) gave 2-((6-chloro-7-methyl-1H-imidazo[4,5-c]pyridin-2-yl)thio)-N-(3-fluoro-4-methoxyphenyl)acetamide (3.1 mg, 8.14 μmol, 16.25% yield) $^1$HNMR (400 MHz, CD$_3$OD) δ 8.36 (s, 1H), 7.50 (d, J=13.4 Hz, 1H), 7.18 (d, J=8.4 Hz, 1H), 7.03 (t, J=9.2 Hz, 1H), 4.21 (s, 2H), 3.84 (s, 3H) 2.53 (s, 3H), ESI-MS: m/z 381.05 (M+H)$^+$

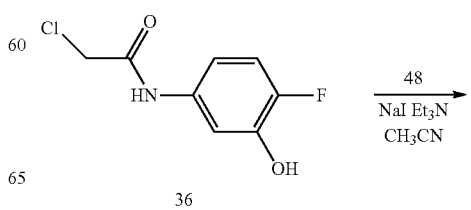

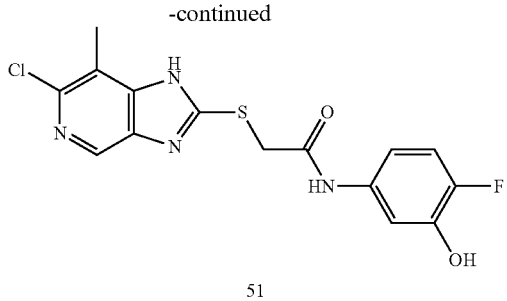

2-((6-Chloro-7-methyl-1H-imidazo[4,5-c]pyridin-2-yl)thio)-N-(4-fluoro-3-hydroxyphenyl)acetamide (Compound 51)

The reaction mixture of 6-chloro-7-methyl-1H-imidazo[4,5-c]pyridine-2-thiol (10 mg, 0.050 mmol), 2-chloro-N-(4-fluoro-3-hydroxyphenyl)acetamide (10.20 mg, 0.050 mmol), sodium iodide (1 mg, 6.67 mmol), triethylamine (0.021 mL, 0.150 mmol) in Acetonitrile (1 mL) was heated at 65° C. for 2 hr. Concentration and purification by prep-TLC (15% MeOH/DCM) gave 2-((6-chloro-7-methyl-1H-imidazo[4,5-c]pyridin-2-yl)thio)-N-(4-fluoro-3-hydroxyphenyl)acetamide (14.5 mg, 0.040 mmol, 79% yield) $^1$HNMR (400 MHz, CD$_3$OD), 8.36 (s, 1H), 7.28 (m, 1H), 6.97 (m, 2H), 4.20 (s, 2H), 2.54 (s, 3H), ESI-MS: m/z 367.00 (M+H)$^+$

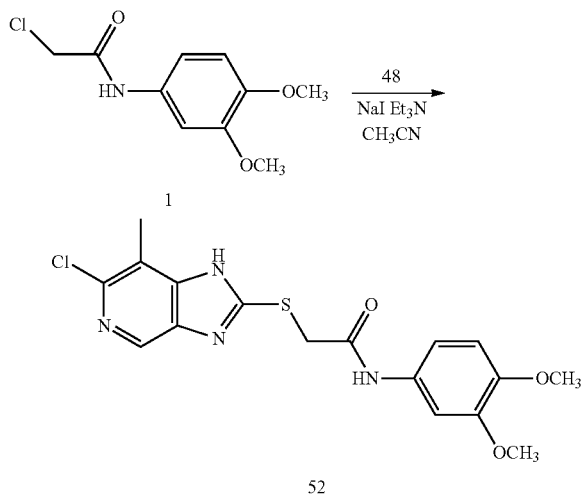

2-((6-Chloro-7-methyl-1H-imidazo[4,5-c]pyridin-2-yl)thio)-N-(3,4-dimethoxyphenyl)acetamide (Compound 52)

The reaction mixture of 6-chloro-7-methyl-1H-imidazo[4,5-c]pyridine-2-thiol (10 mg, 0.050 mmol), 2-chloro-N-(3,4-dimethoxyphenyl)acetamide (11.50 mg, 0.050 mmol), sodium iodide (1 mg, 6.67 μmol), triethylamine (0.021 mL, 0.150 mmol) in acetonitrile (1 mL) was heated at 65° C. for 2 hr. Filtration gave 2-((6-chloro-7-methyl-1H-imidazo[4,5-c]pyridin-2-yl)thio)-N-(3,4-dimethoxyphenyl)acetamide (7.4 mg, 0.019 mmol, 37.6% yield) $^1$HNMR (400 MHz, CD$_3$OD) δ 8.37 (s, 1H), 7.30 (d, J=2.4 Hz, 1H), 7.01 (m, 6.88 (d, J=8.8 Hz, 1H), 4.22 (s, 2H), 3.79 (s, 6H), 2.54 (s, 3H) ESI-MS: m/z 393.05 (M+H)$^+$

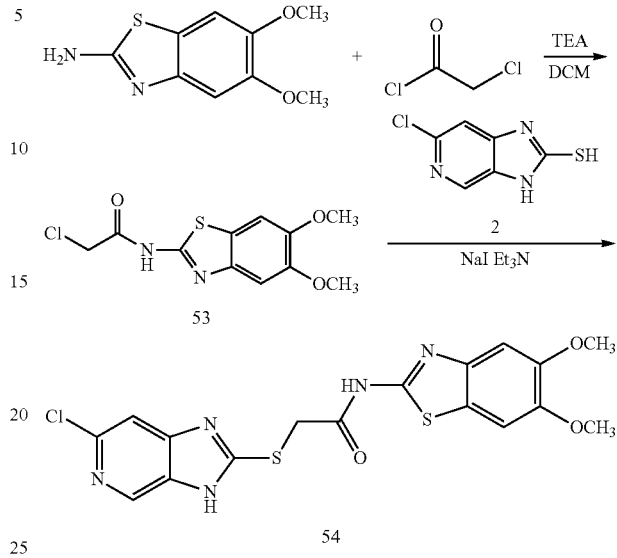

2-Chloro-N-(5,6-dimethoxybenzo[d]thiazol-2-yl)acetamide (Compound 53)

To the reaction mixture of 5,6-dimethoxybenzo[d]thiazol-2-amine (50 mg, 0.238 mmol), TEA (0.100 mL, 0.713 mmol) in DCM (1 mL) was added 2-chloroacetyl chloride (0.023 mL, 0.285 mmol) at room temperature. Overnight, concentration and purification on combiflash (4 g, MeOH/DCM) gave 2-chloro-N-(5,6-dimethoxybenzo[d]thiazol-2-yl)acetamide (15 mg, 0.052 mmol, 22.00% yield). 1HNMR (400 MHz, CDCl$_3$), 9.73 (s, 1H), 7.26 (s, 1H), 7.25 (s, 1H), 4.30 (s, 2H), 3.969s, 6H) ESI-MS: m/z 286.94 (M+H)$^+$

2-((6-Chloro-3H-imidazo[4,5-c]pyridin-2-yl)thio)-N-(5,6-dimethoxybenzo[d]thiazol-2-yl)acetamide (Compound 54)

The reaction mixture of 6-chloro-3H-imidazo[4,5-c]pyridine-2-thiol (6.47 mg, 0.035 mmol), 2-chloro-N-(5,6-dimethoxybenzo[d]thiazol-2-yl)acetamide (10 mg, 0.035 mmol), sodium iodide (1 mg, 6.67 μmol), triethylamine (0.015 mL, 0.105 mmol) in CH$_3$CN (1 mL) was heated at 65° C. for 2 hr. Concentration and combiflash (4 g, DCM/MeOH) gave 2-((6-chloro-3H-imidazo[4,5-c]pyridin-2-yl)thio)-N-(5,6-dimethoxybenzo[d]thiazol-2-yl)acetamide (8 mg, 0.018 mmol, 52.6% yield) $^1$HNMR (400 MHz, CD$_3$OD) δ 8.12 (s, H), 7.41 (s, 1H), 7.33 (s, 2H), 4.38 (s, 2H), 3.89 (s, 3H), 3.88 (s, 3H), ESI-MS: m/z 436.00 (M+H)$^+$

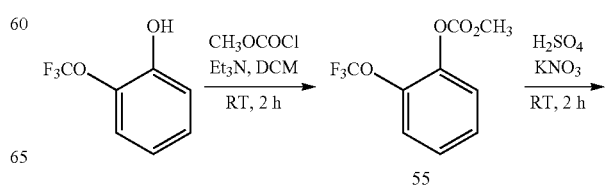

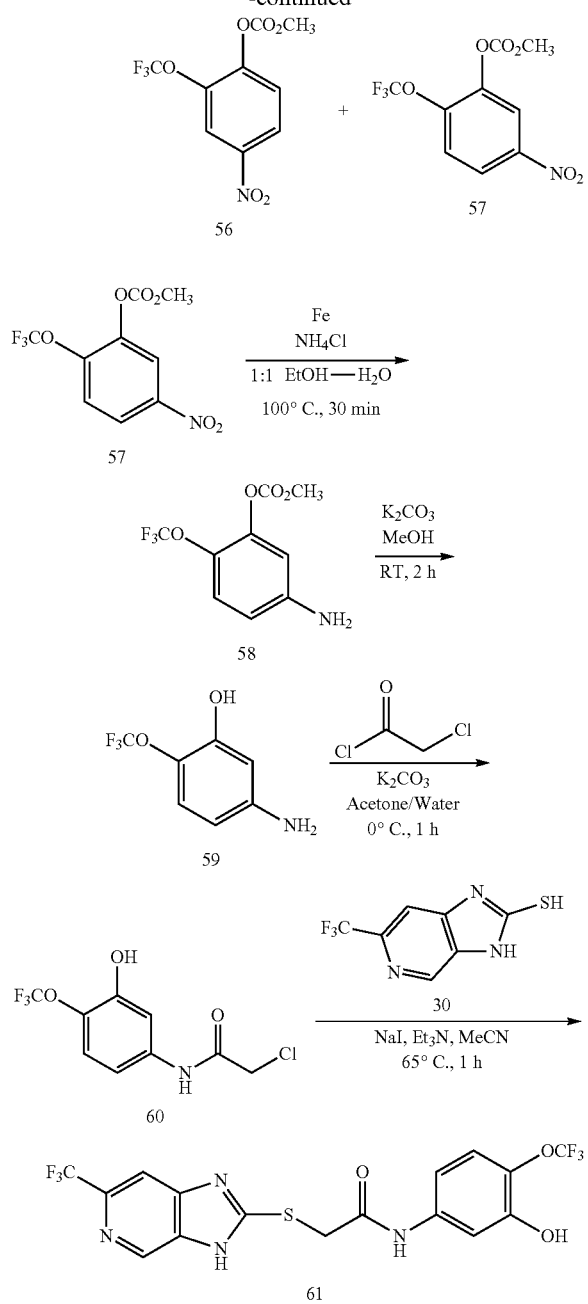

Methyl (2-(trifluoromethoxy)phenyl)carbonate (Compound 55)

To a cooled solution of 2-(trifluoromethoxy)phenol (0.51 ml, 3.93 mmol) and triethylamine (1.1 ml, 7.86 mmol) in DCM was slowly added methyl chloroformate (0.36 ml, 4.72 mmol) and the reaction was stirred at 25° C. for 2 h. Reaction diluted with DCM and washed with water, brine, dried over anhydrous $Na_2SO_4$ and evaporated. The crude cloudy oil (750 mg, 81%) was used in next step without further purification. $^1$H-NMR (400 MHz, $CDCl_3$) δ ppm 7.30 (m, 4H), 3.93 (s, 3H); $^{19}$F-NMR (376.5 MHz, $CDCl_3$) δ ppm −58.10 (s, 3F).

Methyl (5-nitro-2-(trifluoromethoxy)phenyl)carbonate (Compound 57)

A suspension of methyl (2-(trifluoromethoxy)phenyl)carbonate (750 mg, 3.18 mmol) in sulfuric acid (2.0 ml, 37.5 mmol) was cooled and solid potassium nitrate (250 mg, 2.473 mmol) was added portion wise. The mixture was stirred at room temperature for 2 h. Reaction mixture was poured into ice water and extracted with DCM. The combined extracts were washed with water, brine and dried over $Na_2SO_4$. Solvent was removed and the crude was purified by combiflash $SiO_2$ chromatography (0-5% EtOAc-hexanes) to afford methyl (4-nitro-2-(trifluoromethoxy)phenyl)carbonate (250 mg, 28%) and methyl (5-nitro-2-(trifluoromethoxy)phenyl)carbonate (553 mg, 62%) as tan solid.

Methyl (5-nitro-2-(trifluoromethoxy)phenyl)carbonate (Less Polar)

$^1$H-NMR (400 MHz, $CDCl_3$) δ ppm 8.23 (m, 1H), 8.21 (dd, 1H, J=2.4, 8.8 Hz), 7.52 (dd, 1H, J=1.2, 9.2 Hz), 3.98 (s, 3H); $^{19}$F-NMR (376.5 MHz, $CDCl_3$) δ ppm −57.77 (s, 3F)

Methyl (4-nitro-2-(trifluoromethoxy)phenyl)carbonate (Compound 56) (Polar)

$^1$H-NMR (400 MHz, $CDCl_3$) δ ppm 8.25 (m, 2H), 7.52 (dd, 1H, J=4.4, 5.2 Hz), 3.97 (s, 3H); $^{19}$F-NMR (376.5 MHz, $CDCl_3$) δ ppm −58.23 (s, 3F).

5-Amino-2-(trifluoromethoxy)phenyl Methyl Carbonate (Compound 58)

A solution of methyl (5-nitro-2-(trifluoromethoxy)phenyl)carbonate (190 mg, 0.676 mmol) and ammonium chloride (108 mg, 2.027 mmol) in EtOH-water (1:1) was added iron (113 mg, 2.027 mmol) and the mixture was stirred at 100° C. for 30 min in a microwave reactor. Solvents removed and the crude was purified by combiflash $SiO_2$ chromatography (0-30% EtOAc-hexanes) to give 5-amino-2-(trifluoromethoxy)phenyl methyl carbonate (66 mg, 39%) as a brown solid. $^1$H-NMR (400 MHz, $CDCl_3$) δ ppm 7.09 (dd, 1H, J=0.8, 8.4 Hz), 6.54 (d, 1H, J=2.8 Hz), 6.51 (dd, 1H, J=2.8, 8.8 Hz), 3.91 (s, 3H); $^{19}$F-NMR (376.5 MHz, $CDCl_3$) δ ppm −58.82 (s, 3F).

5-Amino-2-(trifluoromethoxy)phenol (Compound 59)

A solution of 5-amino-2-(trifluoromethoxy)phenyl methyl carbonate (66 mg, 0.263 mmol) and potassium carbonate (73 mg, 0.526 mmol) in MeOH-water (2:1) was stirred at room temperature for 1 h. MeOH was removed and the reaction was neutralized with 0.5 M HCl and extracted with EtOAc. The combined organic layers were washed with brine, dried over $Na_2SO_4$ and evaporated. The crude brown solid, 5-amino-2-(trifluoromethoxy)phenol (40 mg, 79%), was used in next step without purification. 1H-NMR (400 MHz, $CD_3OD$) δ ppm 6.88 (dd, 1H, J=0.8, 8.8 Hz), 6.29 (d, 1H, J=2.8 Hz), 6.17 (dd, 1H, J=2.4, 8.8 Hz); $^{19}$F-NMR (376.5 MHz, $CDCl_3$) δ ppm −59.92 (s, 3F); ESI-MS: m/z 193.85 $(M+H)^+$.

2-Chloro-N-(3-hydroxy-4-(trifluoromethoxy)phenyl) acetamide (Compound 60)

To a cooled solution of 5-amino-2-(trifluoromethoxy) phenol (90 mg, 0.466 mmol) and potassium carbonate (77 mg, 0.559 mmol) in acetone-water (3:1) was slowly added 2-chloroacetyl chloride (0.044 ml, 0.559 mmol) and stirred at 0° C. for 2 h. Solvents removed and the crude was purified by combiflash $SiO_2$ chromatography (0-50% EtOAc-hexanes) to give 2-chloro-N-(3-hydroxy-4-(trifluoromethoxy)phenyl)acetamide (98 mg, 78%) as a brown solid. $^1$H-NMR (400 MHz, $CD_3OD$) δ ppm 7.40 (d, 1H, J=2.4 Hz), 7.10 (d, 1H, J=8.8 Hz), 6.95 (dd, 1H, J=2.0, 8.8 Hz, 4.12 (s, 2H); $^{19}$F-NMR (376.5 MHz, $CDCl_3$) δ ppm −59.92 (s, 3F); ESI-MS: m/z 269.92 (M+H)$^+$.

N-(3-Hydroxy-4-(trifluoromethoxy)phenyl)-2-((6-(trifluoromethyl)-3H-imidazo[4,5-c]pyridin-2-yl) thio)acetamide (Compound 61)

A mixture of 2-chloro-N-(3-hydroxy-4-(trifluoromethoxy)phenyl)acetamide (12 mg, 0.045 mmol), 6-(trifluoromethyl)-3H-imidazo[4,5-c]pyridine-2-thiol (11.71 mg, 0.053 mmol), triethylamine (9.31 μl, 0.067 mmol) and sodium iodide (3.34 mg, 0.022 mmol) in MeCN was stirred at 65° C. for 1 h. The crude purified by combiflash $SiO_2$ chromatography (0-5% MeOH-DCM) to give N-(3-hydroxy-4-(trifluoromethoxy)phenyl)-2-((6-(trifluoromethyl)-3H-imidazo[4,5-c]pyridin-2-yl)thio)acetamide (11 mg, 55%) as off white solid. $^1$H-NMR (400 MHz, $CD_3OD$) δ ppm 8.79 (s, 1H), 7.87 (s, 1H), 7.39 (d, 1H, J=2.4 Hz), 7.12 (dd, 1H, J=1.2, 8.8 Hz), 6.97 (dd, 1H, J=2.8, 8.8 Hz), 4.23 (s, 2H); $^{19}$F-NMR (376.5 MHz, $CDCl_3$) δ ppm −60.12 (s, 3F), −67.41 (s, 3F); ESI-MS: m/z 453.01 (M+H)$^+$.

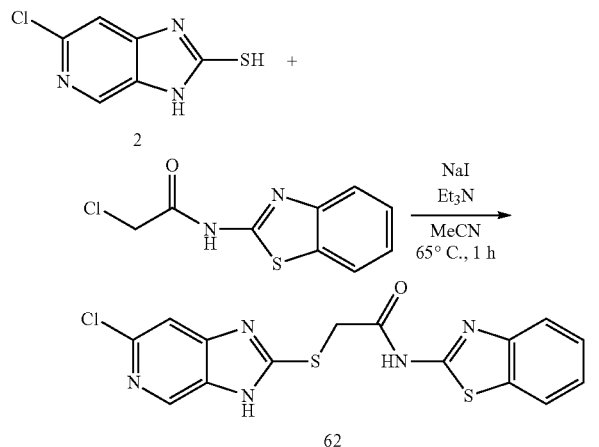

N-(Benzo[d]thiazol-2-yl)-2-((6-chloro-3H-imidazo [4,5-c]pyridin-2-yl)thio)acetamide (Compound 62)

To a mixture of 6-chloro-3H-imidazo[4,5-c]pyridine-2-thiol (10 mg, 0.054 mmol), N-(benzo[d]thiazol-2-yl)-2-chloroacetamide (14.7 mg, 0.065 mmol) and sodium iodide (4.0 mg, 0.027 mmol) in MeCN was added triethylamine (11 μL, 0.081 mmol) and the reaction was stirred at 65° C. for 1 h. Solvents removed and the crude was purified by combiflash $SiO_2$ chromatography (0-5% MeOH-DCM) to give N-(benzo[d]thiazol-2-yl)-2-((6-chloro-3H-imidazo[4,5-c]pyridin-2-yl)thio)acetamide (16 mg, 79%) as a white solid. $^1$H-NMR (400 MHz, DMSO-$d_6$) δ ppm 8.50 (s, 1H), 7.95 (d, 1H, J=8 Hz), 7.75 (d, 1H, J=8 Hz), 7.51 (s, 1H), 7.43 (t, 1H, J=7.2 Hz), 7.29 (t, 1H, J=7.2 Hz), 4.46 (s, 2H); ESI-MS: m/z 375.98 (M)$^+$, 377.99 (M+2H)$^+$.

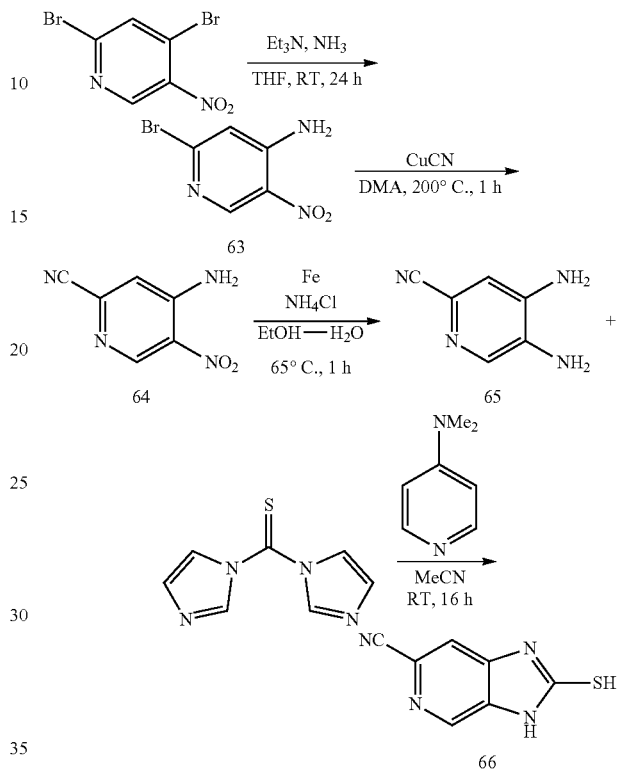

2-Bromo-5-nitropyridin-4-amine (Compound 63)

To a solution of 2,4-dibromo-5-nitropyridine (200 mg, 0.709 mmol) and triethylamine (0.2 ml, 1.419 mmol) in THF 7 M ammonia (0.2 ml, 1.419 mmol) was added and stirred at room temperature for 24 h. Solvents were removed and the crude was purified by combiflash $SiO_2$ chromatography (0-50% EtOAc-hexanes) to give 2-bromo-5-nitropyridin-4-amine (135 mg, 87%) as a tan solid. 1H-NMR (400 MHz, $CD_3OD$) δ ppm 8.82 (s, 1H), 7.11 (s, 1H); m/z 219.69 (M+H)$^+$.

4-Amino-5-nitropicolinonitrile (Compound 64)

A solution of 2-bromo-5-nitropyridin-4-amine (135 mg, 0.619 mmol) and copper cyanide (67 mg, 0.743 mmol) in DMA was heated to 200° C. for 1 h using a microwave reactor. The reaction mixture was partitioned between water and EtOAc and tilted over celite. The aqueous layer was extracted with EtOAc. The combined organic layers were washed with water, brine, dried over $Na_2SO_4$ and concentrated under reduced pressure. The crude was purified by combiflash $SiO_2$ chromatography using (0-50% EtOAc-hexanes) to give 4-amino-5-nitropicolinonitrile (70 mg, 69%) as a pale brown solid. $^1$H-NMR (400 MHz, $CD_3OD$) δ ppm 9.07 (s, 1H), 7.37 (s, 1H); ESI-MS: m/z 164.77 (M+H)$^+$.

4,5-Diaminopicolinonitrile (Compound 65)

A slurry of 4-amino-5-nitropicolinonitrile (70 mg, 0.427 mmol) and iron (72 mg, 1.280 mmol) in EtOH was added ammonium chloride (68 mg, 1.280 mmol) in water and the mixture was heated to 65° C. for 1 h. The reaction mixture was filtered through celite and the solvents were removed. The crude was purified by combiflash SiO$_2$ chromatography (0-5% MeOH-DCM) to give 4,5-diaminopicolinonitrile (32 mg, 56%) as a pale brown solid. $^1$H-NMR (400 MHz, CD$_3$OD) δ ppm 7.72 (s, 1H), 6.92 (s, 1H); ESI-MS: m/z 134.85 (M+H)$^+$.

2-Mercapto-3H-imidazo[4,5-c]pyridine-6-carbonitrile (Compound 66)

A solution of 4,5-diaminopicolinonitrile (32 mg, 0.239 mmol), di(1H-imidazol-1-yl)methanethione (51 mg, 0.286 mmol) and N,N-dimethylpyridin-4-amine (29 mg, 0,239 mmol) in MeCN was stirred at room temperature for 16 h. MeCN was removed and the crude was purified by combiflash SiO$_2$ chromatography (0-5% MeOH-DCM) to give 2-mercapto-3H-imidazo[4,5-c]pyridine-6-carbonitrile (30 mg, 71%) as tan solid. $^1$H-NMR (400 MHz, CD$_3$OD) δ ppm 8.43 (s, 1H), 7.64 (s, 1H); ESI-MS: m/z 176.91 (M+H)$^+$.

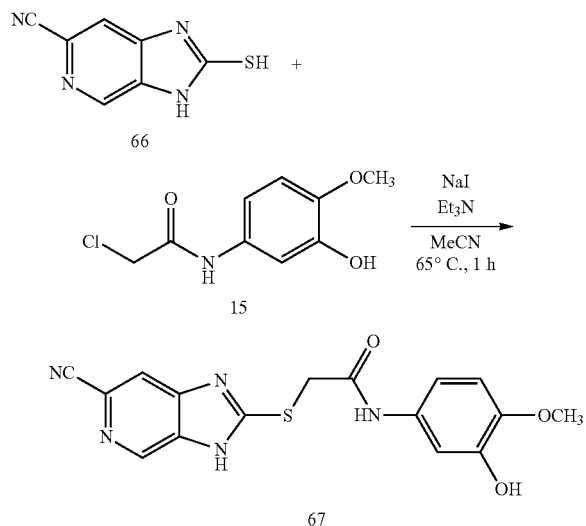

2-((6-Cyano-3H-imidazo[4,5-c]pyridin-2-yl)thio)-N-(3-hydroxy-4-methoxyphenyl)acetamide (Compound 67)

A mixture of 2-chloro-N-(3-hydroxy-4-methoxyphenyl)acetamide (3.3 mg, 0.015 mmol), 2-mercapto-3H-imidazo[4,5-c]pyridine-6-carbonitrile (3 mg, 0.017 mmol) and sodium iodide (1.2 mg, 7.74 μmol) in MeCN was added triethylamine (2.6 μL, 0.019 mmol) and the solution was stirred for 1 h at 65° C. Solvent was removed and the crude was purified by combiflash SiO$_2$ chromatography (0-5% MeOH-DCM) to give 2-((6-cyano-3H-imidazo[4,5-c]pyridin-2-yl)thio)-N-(3-hydroxy-4-methoxyphenyl)acetamide (5 mg, 91%) as an off-white solid. $^1$H-NMR (400 MHz, CD$_3$OD-CDCl$_3$) δ ppm 8.77 (s, 1H), 7.93 (s, 1H), 7.10 (d, 1H, J=2.8 Hz), 6.94 (dd, 1H, J=2.8, 8.8 Hz), 6.79 (d, 1H, J=8.8 Hz), 4.15 (s, 2H), 3.80 (s, 3H); ESI-MS: m/z 375.98 (M)$^+$, 356.04 (M+2H)$^+$.

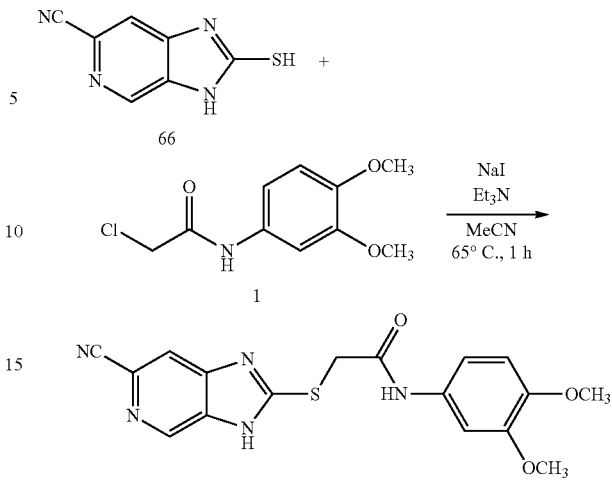

2-((6-Cyano-3H-imidazo[4,5-c]pyridin-2-yl)thio)-N-(3,4-dimethoxyphenyl)acetamide (Compound 68)

A mixture of 2-chloro-N-(3,4-dimethoxyphenyl)acetamide (14 mg, 0.062 mmol), 2-mercapto-3H-imidazo[4,5-c]pyridine-6-carbonitrile (10 mg, 0.057 mmol) and sodium iodide (4.3 mg, 0.028 mmol) in MeCN was added triethylamine (12 μL, 0.085 mmol) and stirred at 65° C. for 1 h. MeCN was removed and the crude was purified by combiflash SiO$_2$ chromatography (0-5% MeOH-DCM) to afford 2-((6-cyano-3H-imidazo[4,5-c]pyridin-2-yl)thio)-N-(3,4-dimethoxyphenyl)acetamide (15 mg, 72%) as a white solid. $^1$H-NMR (400 MHz, CD$_3$OD-CDCl$_3$) δ ppm 8.80 (s, 1H), 7.98 (s, 1H), 7.33 (d, 1H, J=2.4 Hz), 7.01 (dd, 1H, J=2.4, 8.8 Hz), 6.87 (d, 1H, J=8.8 Hz), 4.24 (s, 2H), 3.81 (s, 3H), 3.30 (s, 3H); ESI-MS: m/z 370.05 (M+H)$^+$.

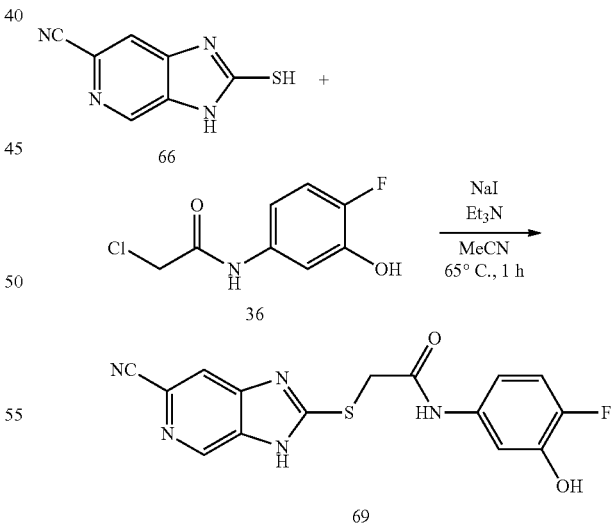

2-((6-Cyano-3H-imidazo[4,5-c]pyridin-2-yl)thio)-N-(4-fluoro-3-hydroxyphenyl)acetamide (Compound 69)

A mixture of 2-chloro-N-(4-fluoro-3-hydroxyphenyl)acetamide (13 mg, 0.062 mmol), 2-mercapto-3H-imidazo[4, 5-c]pyridine-6-carbonitrile (10 mg, 0.057 mmol) and sodium iodide (4.3 mg, 0.028 mmol) in MeCN was added triethylamine (12 μL, 0.085 mmol) and stirred at 65° C. for 1 h. MeCN was removed and the crude was purified by combiflash SiO₂ chromatography (0-5% MeOH-DCM) to afford 2-((6-cyano-3H-imidazo[4,5-c]pyridin-2-yl)thio)-N-(4-fluoro-3-hydroxyphenyl)acetamide (11 mg, 57%) as a white solid. ¹H-NMR (400 MHz, CD₃OD-CDCl₃) δ ppm 8.79 (s, 1H), 7.95 (s, 1H), 7.25 (dd, 1H, J=2.4, 7.6 Hz), 6.95 (d, 1H, J=8.8 Hz), 6.91 (m, 1H), 4.19 (s, 2H); ESI-MS: m/z 344.01 (M+H)⁺.

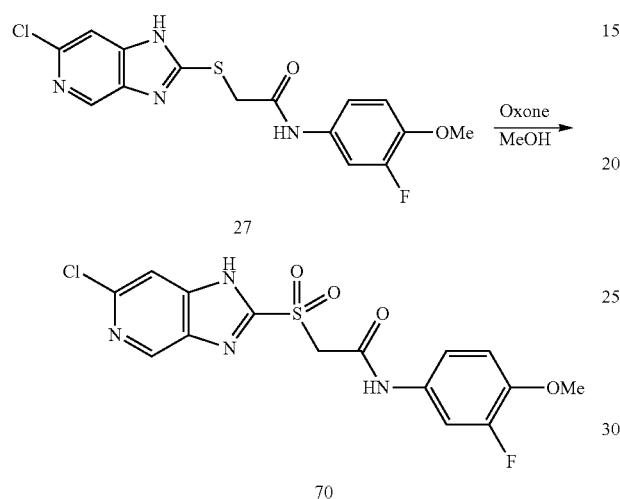

2-((6-chloro-1H-imidazo[4,5-c]pyridin-2-yl)sulfonyl)-N-(3-fluoro-4-methoxyphenyl)acetamide (Compound 27)

To the solution of 2-((6-chloro-1H-imidazo[4,5-c]pyridin-2-yl)thio)-N-(3-fluoro-4-methoxyphenyl)acetamide (5 mg, 0.014 mmol) in methanol (1 mL, 0.014 mmol) was added Oxone (20.95 mg, 0.068 mmol). Overnight, the product was purified on Prep-TLC (MeOH/DCM) gave 2-((6-chloro-1H-imidazo[4,5-c]pyridin-2-yl)sulfonyl)-N-(3-fluoro-4-methoxyphenyl)acetamide (2.1 mg, 5.27 μmol, 38.6% yield). ¹HNMR (400 MHz, CD₃OD) δ 8.72 (s, 1H), 7.62 (s, 1H), 7.40 (M, 1H), 7.13 (d, J=7.6 Hz, 1H), 7.00 (m, 1H), 3.83 (s, 3H) ESI-MS: m/z 399.0 (M+H)⁺

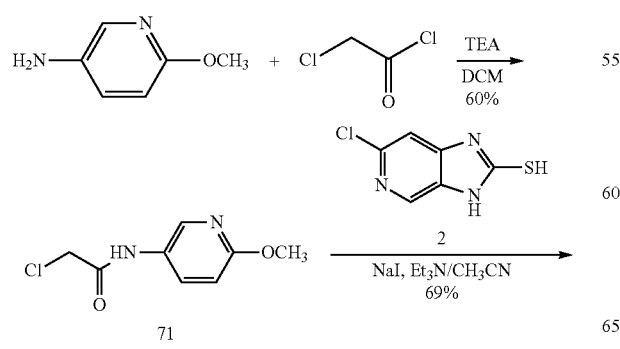

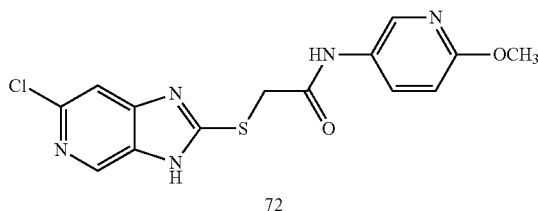

2-Chloro-N-(6-methoxypyridin-3-yl)acetamide (Compound 71)

To the solution of 6-methoxypyridin-3-amine (53 mg, 0.427 mmol), TEA (0.179 mL, 1.281 mmol) in DCM (2 mL) was added 2-chloroacetyl chloride (0.037 mL, 0.470 mmol) at room temperature. After 1 hr, Concentration and purification on combiflash (4 g, EtOAc/Hexane) gave 2-chloro-N-(6-methoxypyridin-3-yl)acetamide (51 mg, 0.254 mmol, 59.5% yield). ¹HNMR (400 MHz, CDCl₃) δ 8.30 (d, J=2.4 Hz, 1H), 7.88 (m, 1H), 6.79 (d, J=8.8 Hz, 1H), 4.18 (s, 2H). ESI-MS: m/z 200.98 (M+H)⁺

2-((6-chloro-3H-imidazo[4,5-c]pyridin-2-yl)thio)-N-(6-methoxypyridin-3-yl)acetamide (Compound 72)

The reaction mixture of 6-chloro-3H-imidazo[4,5-c]pyridine-2-thiol (9.25 mg, 0.050 mmol), 2-chloro-N-(6-methoxypyridin-3-yl)acetamide (10 mg, 0.050 mmol), sodium iodide (1 mg, 6.67 μmol), triethylamine (0.021 mL, 0.150 mmol) in CH3CN (1 mL) was heated at 65° C. for 2 hr. Filtration gave 2-((6-chloro-3H-imidazo[4,5-c]pyridin-2-yl)thio)-N-(6-methoxypyridin-3-yl)acetamide (12 mg, 0.034 mmol, 68.8% yield) ¹HNMR (400 MHz, CD₃OD) δ 8.63 (s, 1H), 8.43 (d, J=2.4 Hz, 1H), 8.01 (m 1H), 7.62 (s, 1H), 6.90 (d, J=8.8 Hz, 1H), 4.38 (s, 2H), 4.00 (s, 3H)

ESI-MS: m/z 349.95 (M+H)⁺

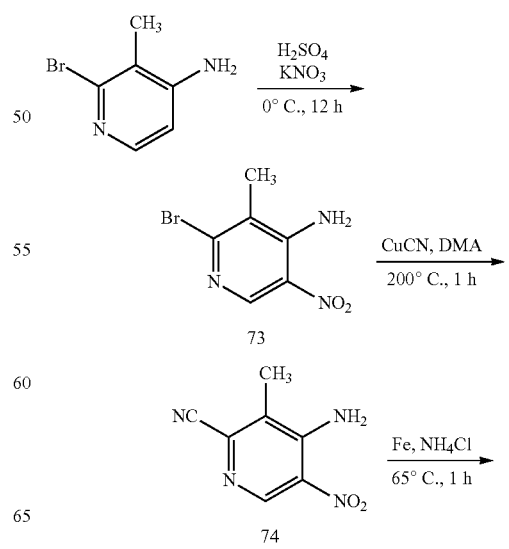

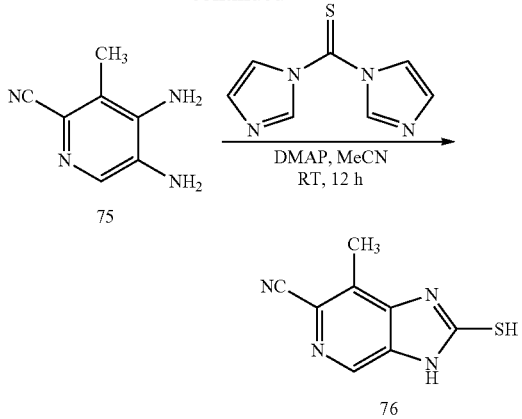

2-Bromo-3-methyl-5-nitropyridin-4-amine (Compound 73)

A mixture of 2-bromo-3-methylpyridin-4-amine (100 mg, 0.535 mmol) in sulfuric acid (849 µl, 16.04 mmol) was cooled to 0° C., and added potassium nitrate (162 mg, 1.604 mmol). The mixture was stirred at 0° C. for additional 1 h and at room temperature for 16 h. The reaction mixture was poured into ice water, basified with sat. NaHCO$_3$ and extracted with EtOAc. The combined EtOAc layers were washed with water, brine, dried over Na$_2$SO$_4$ and evaporated. The crude was purified by combiflash SiO$_2$ chromatography (0-20% EtOAc-hexanes) to give 2-bromo-3-methyl-5-nitropyridin-4-amine (54 mg, 44%) as a yellow solid. $^1$H-NMR (400 MHz, CDCl$_3$—CD$_3$OD) δ ppm 8.69 (s, 1H), 2.22 (s, 3H); ESI-MS: m/z 231.86 (M$^+$) 233.85 (M+2H)$^+$.

4-Amino-3-methyl-5-nitropicolinonitrile (Compound 74)

A solution of 2-bromo-3-methyl-5-nitropyridin-4-amine (52 mg, 0.224 mmol) and cyanocopper (24.09 mg, 0.269 mmol) in DMA was heated to 200° C. in a microwave reactor for 1 h. The reaction mixture was poured into water and extracted with EtOAc. The combined organic layers were washed with water, brine, dried over Na$_2$SO$_4$ and evaporated. The crude was purified by combiflash SiO$_2$ chromatography (0-30% EtOAc-hexanes) to give 4-amino-3-methyl-5-nitropicolinonitrile (30 mg, 75%) as a pale yellow solid. $^1$H-NMR (400 MHz, CD$_3$OD) δ ppm 8.99 (s, 1H), 2.44 (s, 3H); ESI-MS: m/z 178.93 (M+H)$^+$.

4,5-Diamino-3-methylpicolinonitrile (Compound 75)

A solution of 4-amino-3-methyl-5-nitropicolinonitrile (30 mg, 0.168 mmol) in EtOH was added iron (9.40 mg, 0.168 mmol) followed by a solution of ammonium chloride (9.01 mg, 0.168 mmol) in water and stirred at 65° C. for 1 h. The reaction mixture was filtered through celite and evaporated. The crude was purified by combiflash SiO$_2$ chromatography (0-5% MeOH-DCM) to give 4,5-diamino-3-methylpicolinonitrile (15 mg, 60%) as a brown solid. $^1$H-NMR (400 MHz, CD$_3$OD) δ ppm 7.77 (s, 1H), 2.29 (s, 3H). ESI-MS: m/z 148.97 (M+H)$^+$

2-Mercapto-7-methyl-3H-imidazo[4,5-c]pyridine-6-carbonitrile (Compound 76)

A mixture of 4,5-diamino-3-methylpicolinonitrile (15 mg, 0.101 mmol), di(1H-imidazol-1-yl)methanethione (27.1 mg, 0.152 mmol) and N,N-dimethylpyridin-4-amine (14.84 mg, 0.121 mmol) in MeCN was stirred at room temperature for 16 h. Solvent was removed and the crude was purified by combiflash SiO$_2$ chromatography (0-5% MeOH-DCM) to give 2-mercapto-7-methyl-3H-imidazo[4,5-c]pyridine-6-carbonitrile (17 mg, 88%) as a pale brown solid. $^1$H-NMR (400 MHz, CD$_3$OD) δ ppm 8.31 (s, 1H), 2.59 (s, 3H); ESI-MS: m/z 190.93 (M+H)$^+$.

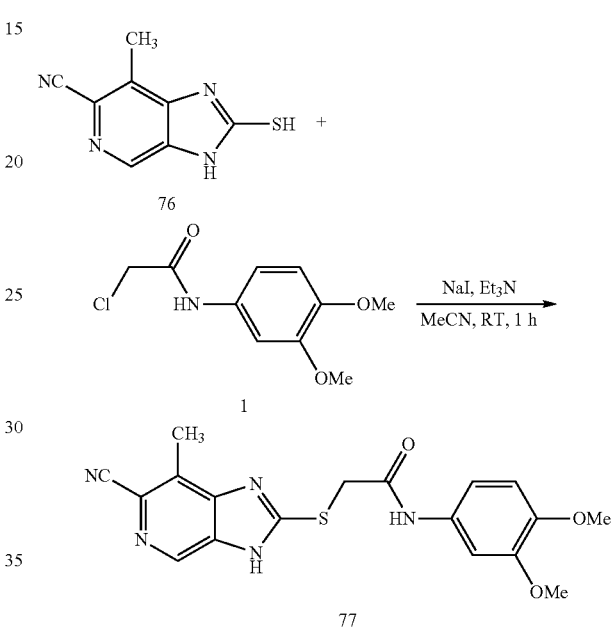

2-((6-Cyano-7-methyl-3H-imidazo[4,5-c]pyridin-2-yl)thio)-N-(3,4-dimethoxyphenyl)acetamide (Compound 77)

A mixture of 2-mercapto-7-methyl-3H-imidazo[4,5-c] pyridine-6-carbonitrile (3 mg, 0.016 mmol), 2-chloro-N-(3,4-dimethoxyphenyl)acetamide (4.35 mg, 0.019 mmol) and sodium iodide (1.182 mg, 7.89 µmol) in MeCN was added triethylamine (3.30 µl, 0.024 mmol) and heated to 65° C. for 1 h. Solvent was removed and the crude was purified by combiflash SiO$_2$ chromatography (0-10% MeOH-DCM) to give 2-((6-cyano-7-methyl-3H-imidazo[4,5-c]pyridin-2-yl) thio)-N-(3,4-dimethoxyphenyl)acetamide (4 mg, 66%) as a white solid. $^1$H-NMR (400 MHz, CDCl$_3$—CD$_3$OD) δ ppm 8.64 (s, 1H), 7.32 (s, 1H), 6.98 (d, 1H, J=7.6 Hz), 6.84 (dd, 1H, J=3.2, 8.8 Hz), 4.20 (s, 2H), 3.82 (s, 3H), 3.81 (s, 3H), 2.71 (s, 3H); ESI-MS: m/z 384.06 (M+H)$^+$.

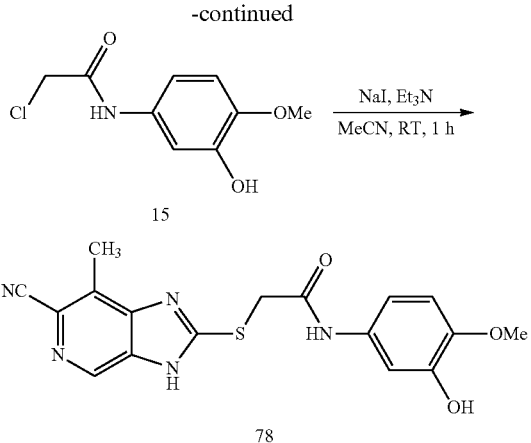

2-((6-Cyano-7-methyl-3H-imidazo[4,5-c]pyridin-2-yl)thio)-N-(3-hydroxy-4-methoxyphenyl)acetamide (Compound 78)

A mixture of 2-mercapto-7-methyl-3H-imidazo[4,5-c]pyridine-6-carbonitrile (7 mg, 0.037 mmol), 2-chloro-N-(3-hydroxy-4-methoxyphenyl)acetamide (8.73 mg, 0.040 mmol), sodium iodide (2.76 mg, 0.018 mmol) in MeCN was added triethylamine (7.69 µl, 0.055 mmol) and heated to 65° C. for 1 h. Solvent was removed and the crude was purified by combiflash SiO$_2$ chromatography (0-10% MeOH-DCM) to give 2-((6-cyano-7-methyl-3H-imidazo[4,5-c]pyridin-2-yl)thio)-N-(3-hydroxy-4-methoxyphenyl)acetamide (7 mg, 52%) as a white solid. $^1$H-NMR (400 MHz, CDCl$_3$-CD$_3$OD) δ ppm 8.64 (s, 1H), 7.10 (d, 1H, J=2.4 Hz), 6.94 (dd, 1H, J=2.4, 8.8 Hz), 6.84 (d, 1H, J=8.8 Hz), 4.18 (s, 2H), 3.82 (s, 3H), 3.81 (s, 3H), 2.71 (s, 3H); ESI-MS: m/z 370.05 (M+H)$^+$.

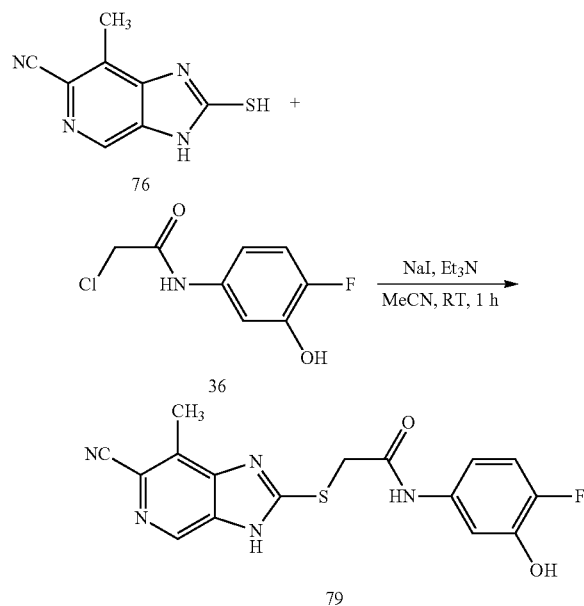

2-((6-Cyano-7-methyl-3H-imidazo[4,5-c]pyridin-2-yl)thio)-N-(4-fluoro-3-hydroxyphenyl)acetamide (Compound 79)

A mixture of 2-mercapto-7-methyl-3H-imidazo[4,5-c]pyridine-6-carbonitrile (11.21 mg, 0.059 mmol), 2-chloro-N-(4-fluoro-3-hydroxyphenyl)acetamide (10 mg, 0.049 mmol) and sodium iodide (3.68 mg, 0.025 mmol) in MeCN was added triethylamine (10.27 µl, 0.074 mmol) and stirred at 65° C. for 1 h. MeCN was removed and the crude was purified by combiflash SiO$_2$ chromatography (0-5% MeOH-DCM) to afford 2-((6-cyano-7-methyl-3H-imidazo[4,5-c]pyridin-2-yl)thio)-N-(4-fluoro-3-hydroxyphenyl)acetamide (10 mg, 57%) as a white solid. $^1$H-NMR (400 MHz, CDCl$_3$-CD$_3$OD) δ ppm 8.22 (s, 1H), 6.82 (dd, 1H, J=2.4, 8.0 Hz), 6.49 (m, 2H), 3.76 (s, 2H), 2.29 (s, 3H); ESI-MS: m/z 358.03 (M+H)$^+$.

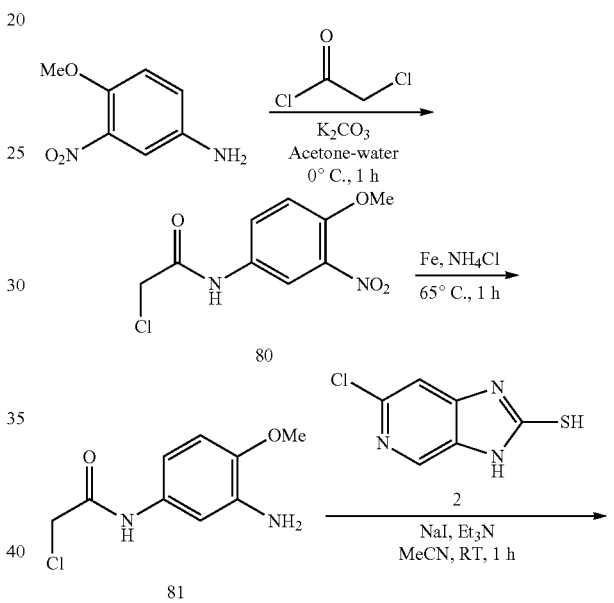

2-Chloro-N-(4-methoxy-3-nitrophenyl)acetamide (Compound 80)

A solution of 4-methoxy-3-nitroaniline (100 mg, 0.595 mmol) in acetone was mixed with a solution of potassium carbonate (123 mg, 0.892 mmol) in water and cooled before the addition of 2-chloroacetyl chloride (0.061 ml, 0.773 mmol). The reaction mixture was stirred at 0° C. for 1 h. The reaction mixture was diluted with EtOAc, washed with 1 M HCl, sat. NaHCO$_3$, water, brine and dried over Na$_2$SO$_4$. The solvent was removed and the crude, 2-chloro-N-(4-methoxy-3-nitrophenyl)acetamide (120 mg, 82%) as a yellow solid, was used in the next step without further purification. $^1$H-NMR (400 MHz, CDCl$_3$) δ ppm 8.25 (brs, 1H), 8.06 (d, 1H, J=2.4 Hz), 7.80 (dd, 1H, J=2.4, 8.8 Hz), 7.09 (d, 1H, J=8.8 Hz), 4.21 (s, 2H), 3.96 (s, 3H), 3.81 (s, 3H); ESI-MS: m/z 244.98 (M+H)⁺, 266.94 (M+Na)⁺.

N-(3-Amino-4-methoxyphenyl)-2-chloroacetamide (Compound 81)

A mixture of 2-chloro-N-(4-methoxy-3-nitrophenyl)acetamide (50 mg, 0.204 mmol) and iron (34.2 mg, 0.613 mmol) in EtOH as added a solution of ammonium chloride (32.8 mg, 0.613 mmol) and the mixture was stirred at 65° C. for 1 h. The reaction was filtered through celite and the solvents were removed. The crude brown solid, N-(3-amino-4-methoxyphenyl)-2-chloroacetamide (30 mg, 68%), was used in the next step without further purification. ¹H-NMR (400 MHz, CDCl₃—CD₃OD) δ ppm 7.08 (s, 1H), 6.89 (d, 1H, J=8 Hz), 6.79 (d, 1H, J=8.8 Hz), 4.15 (s, 2H), 3.82 (s, 3H), 3.81 (s, 3H); ESI-MS: m/z 214.99 (M+H)⁺.

N-(3-Amino-4-methoxyphenyl)-2-((6-chloro-3H-imidazo[4,5-c]pyridin-2-yl)thio)acetamide (Compound 82)

A mixture of N-(3-amino-4-methoxyphenyl)-2-chloroacetamide (15 mg, 0.070 mmol), 6-chloro-3H-imidazo[4,5-c]pyridine-2-thiol (10.81 mg, 0.058 mmol) and sodium iodide (4.36 mg, 0.029 mmol) in MeCN was added triethylamine (12.18 μl, 0.087 mmol) and stirred at 65° C. for 1 h. MeCN was removed and the crude was purified by combiflash SiO₂ chromatography (0-5% MeOH-DCM) to afford N-(3-amino-4-methoxyphenyl)-2-((6-chloro-3H-imidazo[4,5-c]pyridin-2-yl)thio)acetamide (5.5 mg, 26%) as a white solid. ¹H-NMR (400 MHz, CDCl₃—CD₃OD) δ ppm 8.51 (s, 1H), 7.50 (s, 1H), 7.01 (d, 1H, J=2.4 Hz), 6.83 (dd, 1H, J=2.4, 8.8 Hz), 6.76 (d, 1H, J=8.8 Hz), 4.19 (s, 2H), 3.82 (s, 3H), 3.81 (s, 3H); ESI-MS: m/z 363.97 (M+H)⁺.

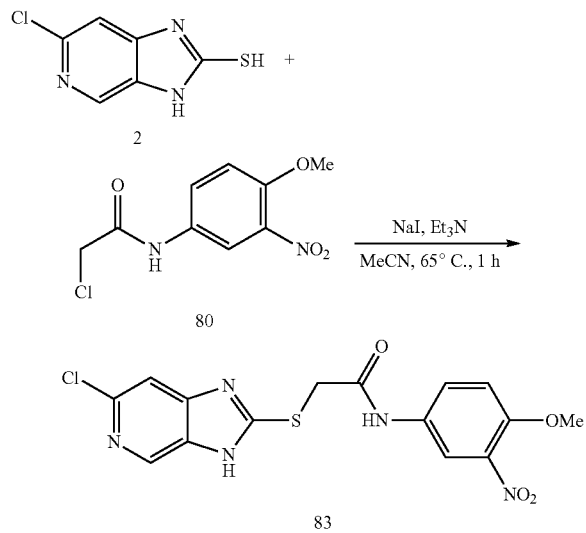

2-((6-Chloro-3H-imidazo[4,5-c]pyridin-2-yl)thio)-N-(4-methoxy-3-nitrophenyl)acetamide (Compound 83)

A mixture of 2-chloro-N-(4-methoxy-3-nitrophenyl)acetamide (15.8 mg, 0.065 mmol), 6-chloro-3H-imidazo[4,5-c]pyridine-2-thiol (10 mg, 0.054 mmol) and sodium iodide (8.07 mg, 0.054 mmol) in MeCN was added triethylamine (11 μl, 0.081 mmol) and stirred at 65° C. for 1 hr. MeCN was removed and the crude was purified by combiflash SiO2 chromatography (0-5% MeOH-DCM) to afford 2-((6-chloro-3H-imidazo[4,5-c]pyridin-2-yl)thio)-N-(4-methoxy-3-nitro-phenyl)acetamide (17 mg, 80%) as a white solid. ¹H-NMR (400 MHz, DMSO-d6) δ ppm 10.72 (s, 1H), 8.51 (s, 1H), 8.22 (d, 1H, J=2.4 Hz), 7.72 (dd, 1H, J=2.4, 8.8 Hz), 7.52 (s, 1H), 7.35 (d, 1H, J=8.8 Hz), 4.32 (s, 2H), 3.87 (s, 3H); ESI-MS: m/z 393.98 (M⁺).

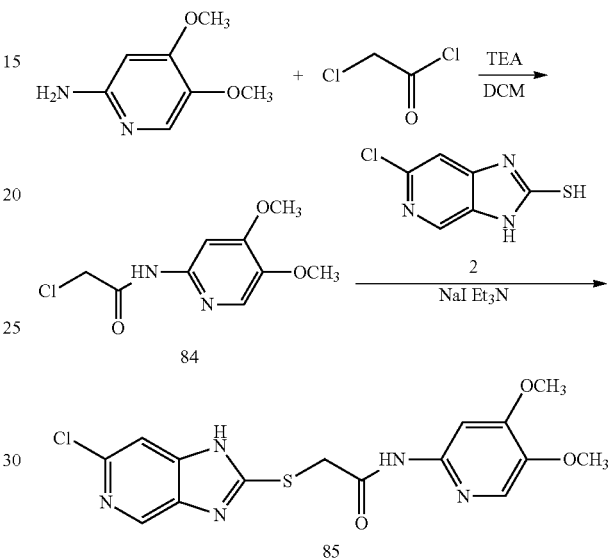

2-Chloro-N-(4,5-dimethoxypyridin-2-yl)acetamide (Compound 84)

To the solution of 4,5-dimethoxypyridin-2-amine (50 mg, 0.324 mmol), TEA (0.113 mL, 0.811 mmol) in DCM (2 mL) was added 2-chloroacetyl chloride (0.028 mL, 0.357 mmol) at room temperature. After 1 hr, concentration and purification on combiflash (4 g, EtOAc/Hexane) gave 2-chloro-N-(4,5-dimethoxypyridin-2-yl)acetamide (19 mg, 0.082 mmol, 25.4% yield). ¹HNMR (400 MHz, CDCl₃) δ ppm 8.72 (s, 1H), 7.87 (s, 1H), 7.8 (s, 1H), 4.18 (s, 2H), 3.97 (s, 3H), 3.92 (s, 3H) ESI-MS: m/z 230.91 (M+H)⁺

2-((6-chloro-1H-imidazo[4,5-c]pyridin-2-yl)thio)-N-(4,5-dimethoxypyridin-2-yl)acetamide (Compound 85)

The reaction mixture of 6-chloro-1H-imidazo[4,5-c]pyridine-2-thiol (7.24 mg, 0.039 mmol), 2-chloro-N-(4,5-dimethoxypyridin-2-yl)acetamide (9 mg, 0.039 mmol), sodium iodide (1 mg, 6.67 μmol), triethylamine (0.016 mL, 0.117 mmol) in CH₃CN (1 mL) was heated to 65° C. for 2 hr. Concentration and purification on combiflash (4 g, MeOH/DCM) gave 2-((6-chloro-1H-imidazo[4,5-c]pyridin-2-yl)thio)-N-(4,5-dimethoxypyridin-2-yl)acetamide (9 mg, 0.024 mmol, 60.7% yield) 1HNMR (400 MHz, CD₃OD) δ ppm 8.52 (s, 1H), 7.82 (s, 1H), 7.78 (s, 1H), 7.51 (s, 4.26 (s, 2H), 3.88 (s, 3H), 3.85 (s, 3H). ESI-MS: m/z 379.96 (M+H)⁺

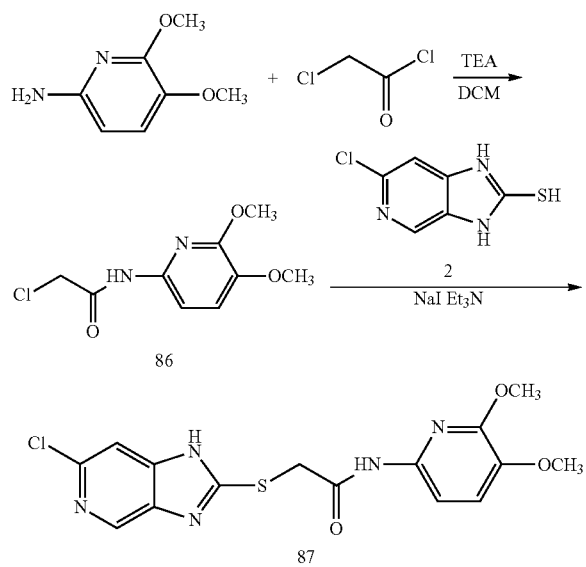

2-Chloro-N-(5,6-dimethoxypyridin-2-yl)acetamide (Compound 86)

To the solution of 5,6-dimethoxypyridin-2-amine (100 mg, 0.649 mmol), TEA (0.226 mL, 1.622 mmol) in DCM (3 mL) was added 2-chloroacetyl chloride (0.057 mL, 0.714 mmol) at room temperature. After 1 hr, concentration and purification on combiflash (4 g, EtOAc/Hexane) gave 2-chloro-N-(5,6-dimethoxypyridin-2-yl)acetamide (85 mg, 0.369 mmol, 56.8% yield). $^1$HNMR (400 MHz, CDCl$_3$) δ ppm 8.75 (s, 1H), 7.95 (d, J=8 Hz, 1H), 7.54 (s, 1H), 7.37 (d, J=8 Hz, 1H), 4.46 (s, 2H), 4.25 (s, 3H), 4.20 (s, 3H). ESI-MS: m/z 231.12 (M+H)$^+$

2-((6-chloro-1H-imidazo[4,5-c]pyridin-2-yl)thio)-N-(5,6-dimethoxypyridin-2-yl)acetamide (Compound 87)

The reaction mixture of 6-chloro-1H-imidazo[4,5-c]pyridine-2-thiol (8.05 mg, 0.043 mmol), 2-chloro-N-(5,6-dimethoxypyridin-2-yl)acetamide (10 mg, 0.043 mmol), sodium iodide (1 mg, 6.67 μmol) and triethylamine (0.018 mL, 0.130 mmol) in CH$_3$CN (1 mL) was heated to 65° C. overnight. Two new sports was purified by pre-TLC (MeOH/DCM) gave 2-((6-chloro-1H-imidazo[4,5-c]pyridin-2-yl)thio)-N-(5,6-dimethoxypyridin-2-yl)acetamide (9 mg, 0.024 mmol, 54.7% yield) $^1$HNMR (400 MHz, CD$_3$OD) δ ppm 8.51 (s, 1H), 7.58 (d, J=8.4 Hz, 1H), 7.51 (s, 1H), 7.22 (d, J=8.4 Hz, 1H), 4.23 (s, 2H), 3.89 (s, 3H), 3.80 (s, 3H). ESI-MS m/z, 380.09 (M+H)$^+$

2-Chloro-N-(4-methoxy-3-((2,2,2-trifluoroethoxy)phenyl)acetamide (Compound 88)

To the solution of 4-methoxy-3-((2,2,2-trifluoroethoxy)aniline (50 mg, 0.226 mmol), TEA (0.079 mL, 0.565 mmol) in DCM (2 mL) was added 2-chloroacetyl chloride (0.020 mL, 0.249 mmol) at room temperature. After 1 hr, concentration and purification on combiflash (4 g, EtOAc/Hexane) gave 2-chloro-N-(4-methoxy-3-((2,2,2-trifluoroethoxy)phenyl)acetamide (49 mg, 0.165 mmol, 72.8% yield). $^1$HNMR (400 MHz, CDCl$_3$) δ ppm 8.13 (s, 1H), 7.36 (s, 1H), 7.26 (s, 1H), 7.13 (d, J=8.8 Hz, 1H), 6.89 (d, J=8.8 Hz, 1H), 4.39 (m, 2H), 4.18 (s, 2H), 3.87 (s, 3H) ESI-MS: m/z 297.92 (M+H)$^+$

2-((6-Chloro-1H-imidazo[4,5-c]pyridin-2-yl)thio)-N-(4-methoxy-3-((2,2,2-trifluoroethoxy)phenyl)acetamide (Compound 89)

The reaction mixture of 6-chloro-1H-imidazo[4,5-c]pyridine-2-thiol (10 mg, 0.054 mmol), 2-chloro-N-(4-methoxy-3-((2,2,2-trifluoroethoxy)phenyl)acetamide (16.04 mg, 0.054 mmol), sodium iodide (1 mg, 6.67 μmol) and triethylamine (0.023 mL, 0.162 mmol) in CH$_3$CN (1 mL) was heated to 65° C. Two new sports was purified by pre-TLC (MeOH/DCM) gave 2-((6-chloro-1H-imidazo[4,5-c]pyridin-2-yl)thio)-N-(4-methoxy-3-((2,2,2-trifluoroethoxy)phenyl)acetamide (9 mg, 0.020 mmol, 37.4% yield) $^1$HNMR (400 MHz, CD$_3$OD) δ ppm 8.50 (s, 1H), 7.50 (s, 1H), 7.37 (s, 1H), 7.16 (d, J=8.8 Hz, 1H), 6.97 (d, J=8.8 Hz, 1H), 4.47 (m, 2H), 4.22 (s, 2H), 3.83 (s, 3H). ESI-MS m/z, 447.01 (M+H)$^+$

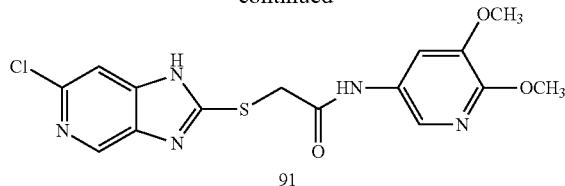

2-Chloro-N-(5,6-dimethoxypyridin-3-yl)acetamide (Compound 90)

To the solution of 5,6-dimethoxypyridin-3-amine (50 mg, 0.324 mmol), TEA (0.113 mL, 0.811 mmol) in DCM (3 mL) was added 2-chloroacetyl chloride (0.028 mL, 0.357 mmol) at room temperature. After 1 hr, concentration and purification on combiflash (4 g, EtOAc/Hexane) gave 2-chloro-N-(5,6-dimethoxypyridin-3-yl)acetamide (56 mg, 0.243 mmol, 74.9% yield). $^1$HNMR (400 MHz, CDCl$_3$) δ ppm 8.16 (s, 1H), 7.71 (s, J=2 Hz, 1H), 7.62 (d, J=2 Hz, 1H), 4.21 (s, 2H), 4.01 (s, 3H), 3.90 (s, 3H) ESI-MS: m/z 230.99 (M+H)$^+$

2-((6-Chloro-1H-imidazo[4,5-c]pyridin-2-yl)thio)-N-(5,6-dimethoxypyridin-3-yl)acetamide (Compound 91)

The reaction mixture of 6-chloro-1H-imidazo[4,5-c]pyridine-2-thiol (8.05 mg, 0.043 mmol), 2-chloro-N-(5,6-dimethoxypyridin-3-yl)acetamide (10 mg, 0.043 mmol), sodium iodide (1 mg, 6.67 µmol) and triethylamine (0.018 mL, 0.130 mmol) in CH$_3$CN (1 mL) was heated to 65° C. overnight. Two new sports was purified by pre-TLC (MeOH/DCM) gave 2-((6-chloro-1H-imidazo[4,5-c]pyridin-2-yl)thio)-N-(5,6-dimethoxypyridin-3-yl)acetamide (13 mg, 0.034 mmol, 79% yield) 1HNMR (400 MHz, CD$_3$OD) δ ppm 8.50 (s, 1H), 7.82 (d, J=2 Hz, 1H), 7.58 (d, J=2 Hz, 1H), 7.50 (s, 1H), 4.25 (s, 2H), 3.91 (s, 3H), 3.82 (s, 3H), ESI-MS m/z, 380.04 (M+H)$^+$

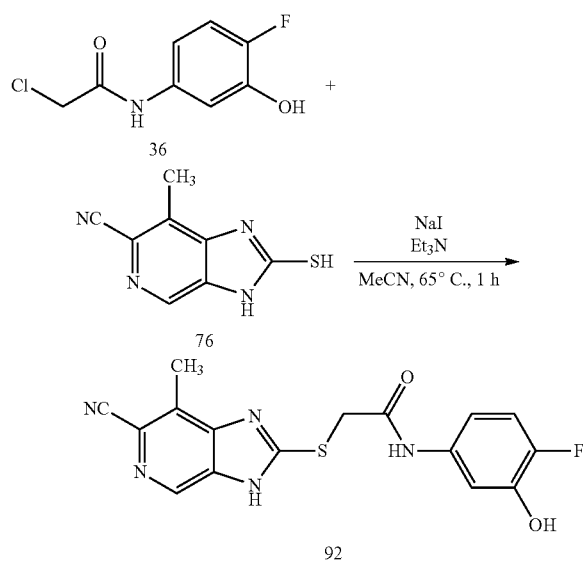

2-((6-Cyano-7-methyl-3H-imidazo[4,5-c]pyridin-2-yl)thio)-N-(4-fluoro-3-hydroxyphenyl)acetamide (Compound 92)

A mixture of 2-mercapto-7-methyl-3H-imidazo[4,5-c]pyridine-6-carbonitrile (11.21 mg, 0.059 mmol), 2-chloro-N-(4-fluoro-3-hydroxyphenyl)acetamide (10 mg, 0.049 mmol) and sodium iodide (3.68 mg, 0.025 mmol) in MeCN was added triethylamine (10.27 µl, 0.074 mmol) and stirred at 65° C. for 1 h. MeCN was removed and the crude was purified by combiflash SiO$_2$ chromatography (0-5% MeOH-DCM) to afford 2-((6-cyano-7-methyl-3H-imidazo[4,5-c]pyridin-2-yl)thio)-N-(4-fluoro-3-hydroxyphenyl)acetamide (10 mg, 57%) as a white solid. $^1$H-NMR (400 MHz, CDCl$_3$—CD$_3$OD) δ ppm 8.22 (s, 1H), 6.82 (dd, 1H, J=2.4, 8.0 Hz), 6.49 (m, 2H), 3.76 (s, 2H), 2.29 (s, 3H); ESI-MS: m/z 358.03 (M+H)$^+$.

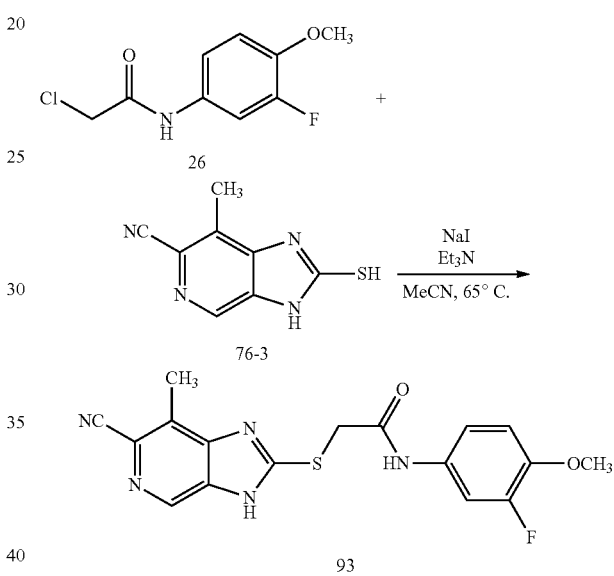

2-((6-Cyano-7-methyl-3H-imidazo[4,5-c]pyridin-2-yl)thio)-N-(3-fluoro-4-methoxyphenyl)acetamide (Compound 93)

A mixture of 2-chloro-N-(3-fluoro-4-methoxyphenyl)acetamide (13.73 mg, 0.063 mmol), 2-mercapto-7-methyl-3H-imidazo[4,5-c]pyridine-6-carbonitrile (10 mg, 0.053 mmol), sodium iodide (3.94 mg, 0.026 mmol) in MeCN was added triethylamine (10.99 µl, 0.079 mmol) and heated to 65° C. for 1 hr. MeCN was removed and the crude was purified by combiflash SiO$_2$ chromatography (0-5% MeOH-DCM) to give 2-((6-cyano-7-methyl-3H-imidazo[4,5-c]pyridin-2-yl)thio)-N-(3-fluoro-4-methoxyphenyl)acetamide (11 mg, 56%) as a white solid. $^1$H-NMR (400 MHz, CDCl$_3$—CD$_3$OD) δ ppm 8.65 (s, 1H), 7.49 (dd, 1H, J=2.8, 13.2 Hz), 7.18 (d, 1H, J=8.4 Hz), 7.01 (t, 1H, J=9.2 Hz), 4.24 (s, 2H), 3.83 (s, 3H), 2.70 (s, 3H); ESI-MS: m/z 372.02 (M+H)$^+$.

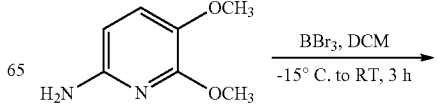

-continued

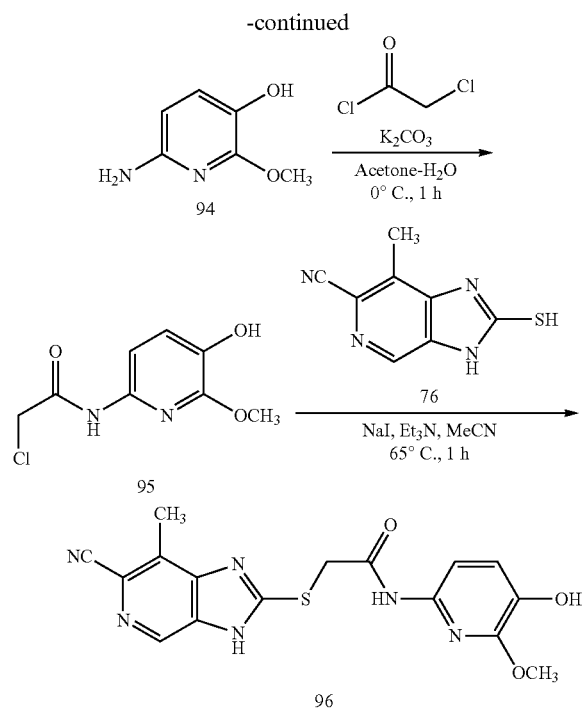

6-Amino-2-methoxypyridin-3-ol (Compound 94)

To a cooled solution of 5,6-dimethoxypyridin-2-amine (70 mg, 0.454 mmol) in DCM, tribromoborane (1.362 ml, 1.362 mmol) (1M in DCM) was slowly added and the mixture was stirred at room temperature for 3 hr. The reaction mixture was quenched with sat.Na$_2$CO$_3$ followed by the addition of water. The aqueous layer was extracted with DCM, and the combined organic layers were washed with water, brine, dried over Na$_2$SO$_4$ and concentrated under reduced pressure. The crude was purified by combiflash SiO$_2$ chromatography to give 6-amino-2-methoxypyridin-3-ol (24 mg, 38%) as a brown solid. $^1$H-NMR (400 MHz, CD$_3$OD) δ ppm 6.91 (d, 1H, J=8 Hz), 6.03 (d, 1H, J=8.4 Hz), 3.87 (s, 3H); ESI-MS m/z 141.17 (M+H)$^+$.

2-Chloro-N-(5-hydroxy-6-methoxypyridin-2-yl)acetamide (Compound 95)

To a cooled mixture of 6-amino-2-methoxypyridin-3-ol (24 mg, 0.171 mmol) and potassium carbonate (28.4 mg, 0.206 mmol) in acetone-water, 2-chloroacetyl chloride (0.015 ml, 0.188 mmol) was slowly added at 0° C. and stirred for 1 h. Reaction was diluted with EtOAc and washed with water, brine, dried over Na$_2$SO$_4$ and evaporated. The crude, 2-chloro-N-(5-hydroxy-6-methoxypyridin-2-yl)acetamide (33 mg, 89%) as a brown solid, was used in the next step without further purification. $^1$H-NMR (400 MHz, CD$_3$OD) δ ppm 7.50 (d, 1H, J=8.4 Hz), 7.07 (d, 1H, J=8.4 Hz), 4.19 (s, 2H), 3.93 (s, 3H); ESI-MS: m/z 217.00 (M+H)$^+$.

2-((6-cyano-7-methyl-3H-imidazo[4,5-c]pyridin-2-yl)thio)-N-(5-hydroxy-6-methoxypyridin-2-yl)acetamide (Compound 96)

To a mixture of 2-chloro-N-(5-hydroxy-6-methoxypyridin-2-yl)acetamide (10 mg, 0.046 mmol), 2-mercapto-7-methyl-3H-imidazo[4,5-c]pyridine-6-carbonitrile (10.54 mg, 0.055 mmol) and sodium iodide (3.46 mg, 0.023 mmol) in MeCN, triethylamine (9.65 µl, 0.069 mmol) was added and the reaction was stirred at 65° C. for 1 hr. Solvent was removed and the crude was purified by combiflash SiO$_2$ chromatography (0-5% MeOH-DCM) to give 2-((6-cyano-7-methyl-3H-imidazo[4,5-c]pyridin-2-yl)thio)-N-(5-hydroxy-6-methoxypyridin-2-yl)acetamide (13 mg, 76%) as a white solid. $^1$H-NMR (400 MHz, DMSO-d$_6$) δ ppm 13.69 (s, 1H), 10.43 (s, 1H), 9.22 (s, 1H), 8.70 (s, 1H), 7.40 (d, H-1, J=8.4 Hz), 7.05 (d, 1H, J=8.0 Hz), 4.34 (s, 2H), 3.84 (s, 3H), 2.62 (s, 3H); ESI-MS: m/z 371.07 (M+H)$^+$.

Experimental Biology:

1. ENPP1 Inhibition Assay

Materials:

Assay Buffer: 1 mM CaCl2, 0.2 mM ZnCl2, 50 mM Tris, pH 9.0

Substrate: 8 mM Thymidine 5'-monophosphate p-nitrophenol ester sodium salt (Sigma Cat # T4510)

Enzyme: 5 ng/µL Recombinant Human ENPP-1 Protein (R&D Cat #6136-EN-010) DMSO 96-well clear assay plates Methods:

An eight point serial dilution of drugs was prepared in 10× in assay buffer with the final assay concentrations starting at 10 µM, 3 µM, 1 µM, 0.3 µM . . . 0 µM. A dilution of DMSO was included as a control. The assay plate was set up as follows with each well in duplicate: 81 µL assay buffer+10 µL ENPP1 inhibitor or DMSO+5 µL Substrate+4 µL Enzyme. Both the enzyme and substrate were added to opposite sides of the well to ensure that there was no interaction until all wells had both components. The plate was then centrifuged gently for 10 seconds, followed by an incubation at 37° C. for 45 minutes. The reaction was quantified by measuring absorbance at 405 nm using the Envision.

IC$_{50}$ Calculation:

IC$_{50}$ values are determined using GraphPad Prism 5 software. The data were entered as an X-Y plot into the software as percent inhibition for each concentration of the drug. The concentration values of the drug were log transformed and the nonlinear regression was carried out using the "sigmoidal dose-response (variable slope)" option within the GraphPad software to model the data and calculate IC$_{50}$ values. The IC$_{50}$ values reported are the concentration of drug at which 50% inhibition was reached.

The results of this experiment are shown in FIG. 1. FIG. 1 demonstrates that compounds 21, 68 and 78 were effective in inhibiting the activity of ENPP1.

2. ENPP2 Inhibition Assay

Materials:

Assay Buffer: 10 mM CaCl$_2$, 5 mM MgCl$_2$, 50 mM Tris, 0.02% Brij-35, pH 8.5

Substrate: 2 mM Bis(p-Nitrophenyl) Phosphate Sodium Salt (Sigma Cat # N3002)

Enzyme: 0.2 ng/µL Recombinant Human ENPP-2/Autotaxin Protein (R&D Cat #5255-EN)

PF-3080

DMSO 96-well clear assay plates

Methods:

An eight point serial dilution of drugs was prepared in 10× in assay buffer with the final assay concentrations starting at 10 µM, 3 µM, 1 µM, 0.3 µM . . . 0 µM. A dilution of DMSO was included as a control. The assay plate was set up as follows with each well in duplicate: 15 µL assay buffer+10 µL, ENPP1 inhibitor or DMSO+50 µL Substrate+25 µL Enzyme. Both the enzyme and substrate were added to opposite sides of the well to ensure that there was no interaction until all wells had both components. The plate was then centrifuged gently for 10 seconds, followed by an incubation at 37° C. for 45 minutes. The reaction was quantified by measuring absorbance at 405 nm using the Envision.

$IC_{50}$ Calculation:

$IC_{50}$ values are determined using GraphPad Prism 5 software. The data were entered as an X-Y plot into the software as percent inhibition for each concentration of the drug. The concentration values of the drug were log transformed and the nonlinear regression was carried out using the "sigmoidal dose-response (variable slope)" option within the GraphPad software to model the data and calculate $IC_{50}$ values. The $IC_{50}$ values reported are the concentration of drug at which 50% inhibition was reached.

Figure 2A:
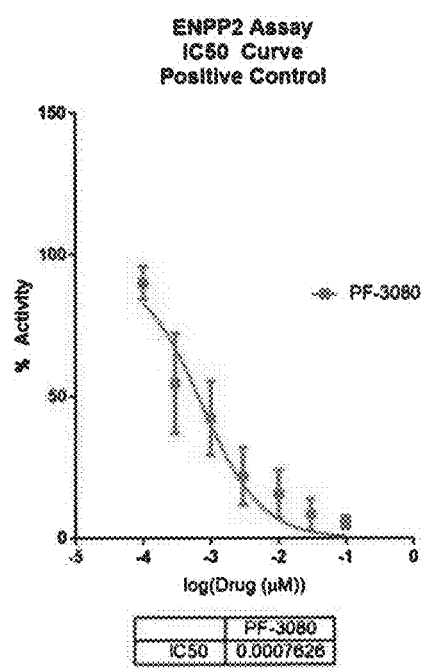
FIG. 2A is a chart of a positive control in ENPP2 Inhibition Assay.
Figure 2B:
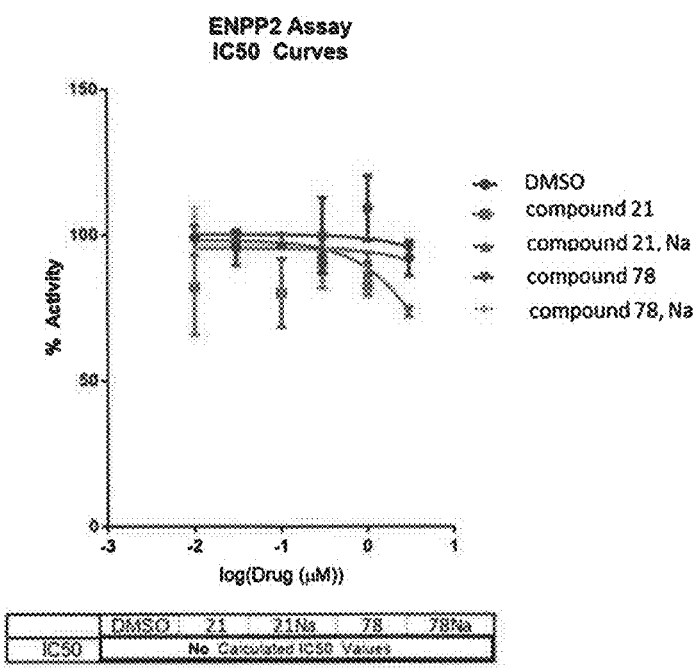
FIG. 2B is a chart of ENPP2 Inhibition Assay for some of the compounds of the invention.

The results of this experiment are shown in FIGS. 2A and 2B. FIGS. 2A and 2B demonstrate that compounds 21 and 78 and their respective sodium salts were ineffective in inhibiting the activity of ENPP2. These results indicate that compounds 21 and 78 were selective at inhibiting ENPP1 but not ENPP2.

3. ENPP1 Thermal Shift Assay
Materials:
Recombinant Human ENPP-1 Protein (R&D Cat #6136-EN-010)
Assay Buffer (1 mM CaCl2, 0.2 mM ZnCl2, 50 mM Tris, pH 9.0)
5000× SYPRO Orange (ThermoFisher cat # S6651)
384-well PCR Plates
Methods:

Each drug was prepared as a 10× solution in the assay buffer and SYPRO Orange was diluted to 10× concentration in water. Wells were set up in duplicate in a 384-well PCR plate as follows: 14 μL assay buffer, 2 μL ENPP1 Inhibitor or DMSO, 2 μL (0.5 μg) ENPP1 protein. Each well was mixed and incubated on ice for 5 minutes. Post incubation, 2 μL of SYPRO Orange was mixed into each well and followed by a gentle centrifugation. The protein melt reaction was run using ViiA7 software with temperatures beginning at 25° C. and increasing by 0.05° C./s to the maximum temperature of 99° C.

The results of this experiment are shown in FIG. 3. FIG. 3 demonstrates that compound 21 was effective in increasing the stability of recombinant ENPP1 protein. The Tm (midpoint of the protein unfolding transition) of ENPP1 was 64.2° C. and this was increased to 67.84° C. in the presence of compound 21. These results suggest that compound 21 binds directly with ENPP1 and modulates its activity.

4. ENPP1 Mineralization Assay
Materials:
Saos-2 Cells (ATCC CAT # HTB-85)
Culture Medium
24-well Tissue Culture Plate
Ascorbic Acid, 5 mg/mL (100×)
β-Glycerophosphate, 1M (100×)
Phosphate Buffered Saline
Alizarin Red, 40 mM pH 4.2
70% Ethanol
Dye Extraction Reagent, 10% Methanol+10% Acetic Acid
Methods:

Saos-2 cells were plated at a density of 1.5×106 cells/well and allowed to grow to 100% confluency over the following 1-2 days. Once completely confluent, the media was replaced with fresh media supplemented with 1× ascorbic acid, 1× β-glycerophosphate, and varying concentrations of ENPP1 inhibitor (if applicable). The addition of the mineralization components was considered Day 1, On Day 3, the media was gently aspirated with no wash followed by the addition of fresh media, mineralization components, and ENPP1 inhibitor (if applicable). On day 5, the media was gently aspirated and the cells were washed twice with PBS. The cells were then fixed with ice cold 70% ethanol for 1 hour at 4° C. Cells were washed once with PBS and stained with Alizarin Red for 30 minutes at room temperature with gentle rotation. Stained cells were washed three times with water for 10 minutes at room temperature with gentle rotation. After imaging cells, dye extraction reagent was added to each well and incubated for 30 minutes at room temperature. Alizarin red was quantified by measuring absorbance at a wavelength of 405 nm using the Envision.

Figure 4:
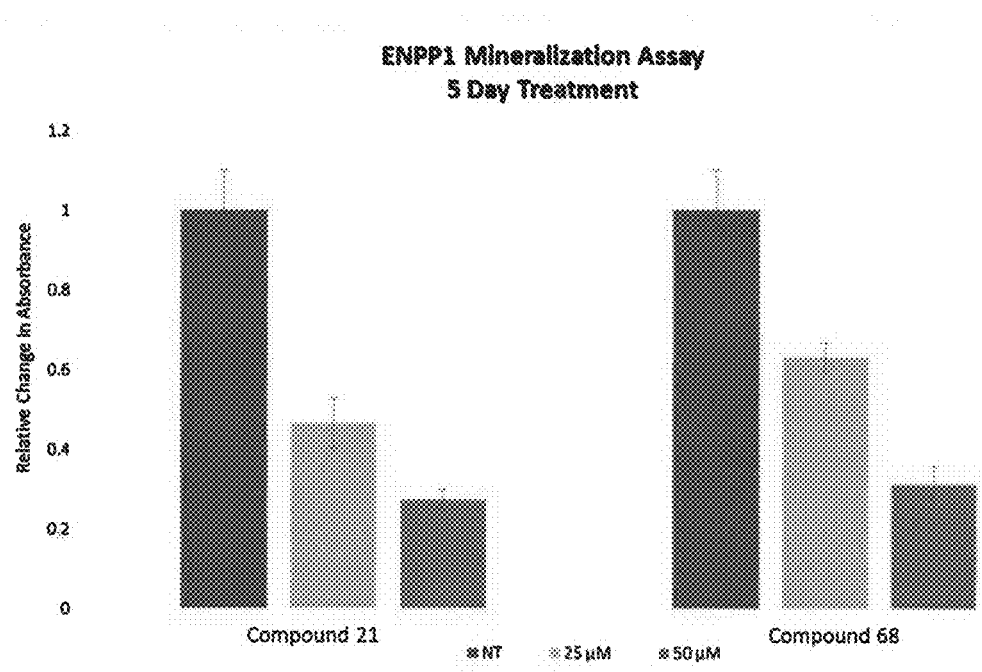
FIG. 4 is a bar chart of ENPP1 Minerazation assay for some of the compounds of the invention.

The results of this experiment are shown in FIG. 4. FIG. 4 demonstrates that compounds 21 and 68 were effective in inhibiting ENPP1 ability to produce mineralized nodules. These results suggest that inhibition of ENPP1 likely altered the pyrophosphate/phosphate ratio, which was previously reported to regulate matrix mineralization of cells.

The ability of representative disclosed compounds to modulate various biochemical and cellular activities was determined using the ENPP1 and ENPP2 inhibition assay, ENPP1 protein stability assay and ENPP1 mineral assay described above.

The $IC_{50}$ (μM) for inhibition of either ENPP1 activity are shown in Tables 1 and 2.

If an $IC_{50}$ or another assay result is indicated as "ND", it was not determined in the indicated assay.

TABLE 1

3H-Imidazo [4,5-c] Pyridine Series 1 of ENPP1 Inhibitors

| Compound Number | Structure | MW. | ENPP1 inhibition ($IC_{50}$) (μM) | ENPP1 Mineral assay (50% inhibition at 50 μM) |
|---|---|---|---|---|
| 3 | 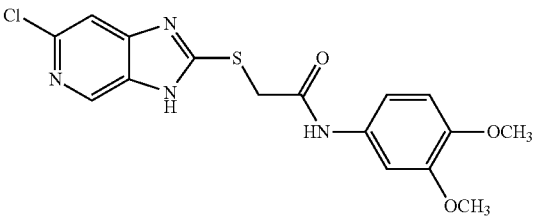 [SMILES: COc1ccc(NC(=O)CSc2nc3cc(Cl)ncc3[nH]2)cc1OC] | $C_{16}H_{15}ClN_4O_3S$ 378.83 | 0.58 | NT |

TABLE 1-continued

3H-Imidazo [4,5-c] Pyridine Series 1 of ENPP1 Inhibitors

| Compound Number | Structure | MW. | ENPP1 inhibition (IC$_{50}$) (μM) | ENPP1 Mineral assay (50% inhibition at 50 μM) |
|---|---|---|---|---|
| 7 | 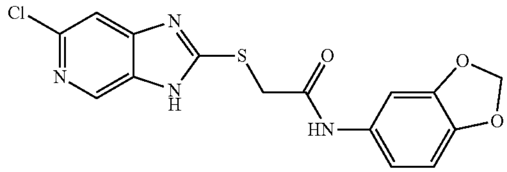 [SMILES: O=C(CSc1nc2cc(Cl)ncc2[nH]1)Nc1ccc2c(c1)OCO2] | C$_{15}$H$_{11}$ClN$_4$O$_3$S<br>362.79 | >50.0 | NT |
| 14 | 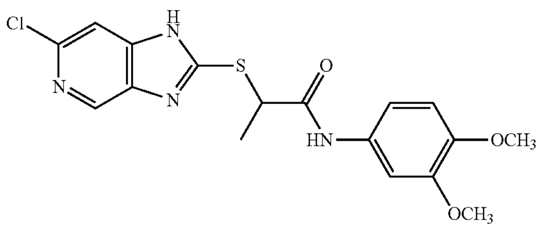 [SMILES: COc1ccc(NC(=O)C(C)Sc2nc3cnc(Cl)cc3[nH]2)cc1OC] | C$_{17}$H$_{17}$ClN$_4$O$_3$S<br>392.86 | 3.522 | NT |
| 21 | 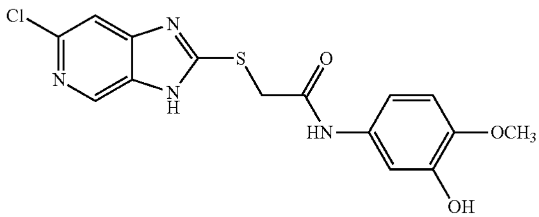 [SMILES: COc1ccc(NC(=O)CSc2nc3cc(Cl)ncc3[nH]2)cc1O] | C$_{15}$H$_{13}$ClN$_4$O$_3$S<br>364.80 | 0.086 | + |
| 22 | 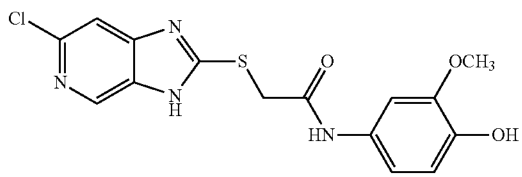 [SMILES: COc1cc(NC(=O)CSc2nc3cc(Cl)ncc3[nH]2)ccc1O] | C$_{15}$H$_{13}$ClN$_4$O$_3$S<br>364.80 | 1.161 | + |
| 25 | 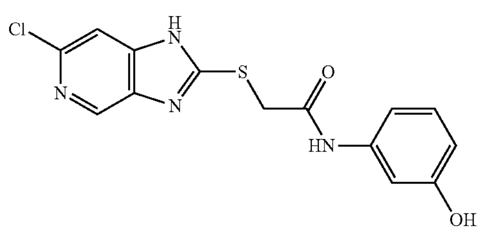 [SMILES: O=C(CSc1nc2cnc(Cl)cc2[nH]1)Nc1cccc(O)c1] | C$_{14}$H$_{11}$ClN$_4$O$_2$S<br>334.78 | 7.932 | NT |
| 40 | 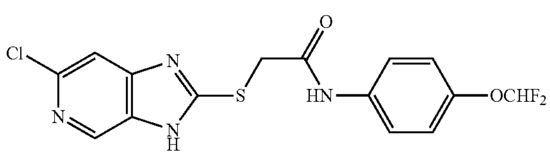 [SMILES: O=C(CSc1nc2cc(Cl)ncc2[nH]1)Nc1ccc(OC(F)F)cc1] | C$_{15}$H$_{11}$ClF$_2$N$_4$O$_2$S<br>384.79 | 33.61 | NT |
| 27 | 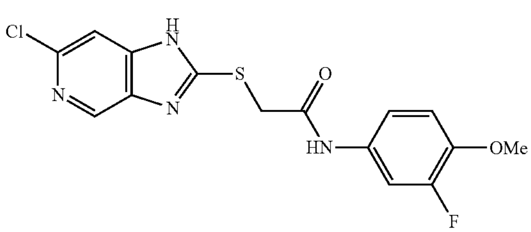 [SMILES: COc1ccc(NC(=O)CSc2nc3cnc(Cl)cc3[nH]2)cc1F] | C$_{15}$H$_{12}$ClFN$_4$O$_2$S<br>366.80 | 0.400 | NT |

TABLE 1-continued

3H-Imidazo [4,5-c] Pyridine Series 1 of ENPP1 Inhibitors

| Compound Number | Structure | MW. | ENPP1 inhibition (IC$_{50}$) (μM) | ENPP1 Mineral assay (50% inhibition at 50 μM) |
|---|---|---|---|---|
| 29 | 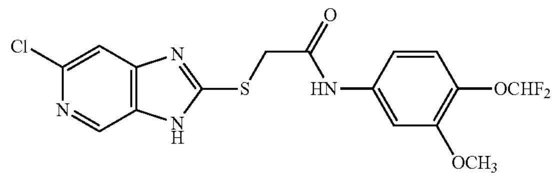 [SMILES: COc1cc(NC(=O)CSc2nc3cc(Cl)ncc3[nH]2)ccc1OC(F)F] | C$_{16}$H$_{13}$ClF$_2$N$_4$O$_3$S 414.81 | 1.162 | NT |
| 31 | 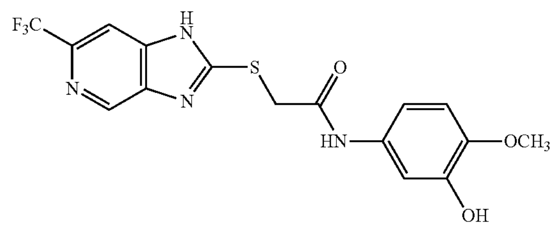 [SMILES: COc1ccc(NC(=O)CSc2nc3cnc(C(F)(F)F)cc3[nH]2)cc1O] | C$_{16}$H$_{13}$F$_3$N$_4$O$_3$S 398.36 | 0.181 | + |
| 33 | 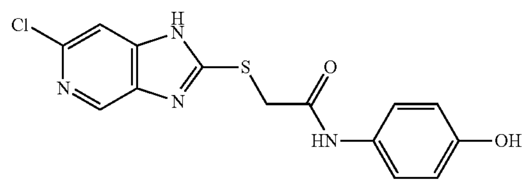 [SMILES: O=C(CSc1nc2cnc(Cl)cc2[nH]1)Nc1ccc(O)cc1] | C$_{14}$H$_{11}$ClN$_4$O$_2$S 334.78 | 7.921 | NT |
| 35 | 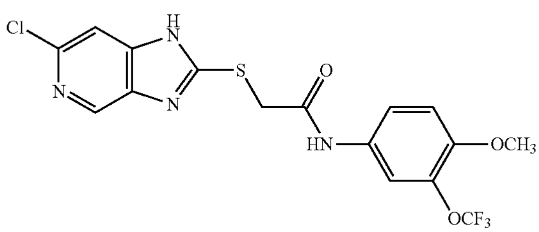 [SMILES: COc1ccc(NC(=O)CSc2nc3cnc(Cl)cc3[nH]2)cc1OC(F)(F)F] | C$_{16}$H$_{12}$ClF$_3$N$_4$O$_3$S 432.80 | 40.69 | NT |
| 37 | 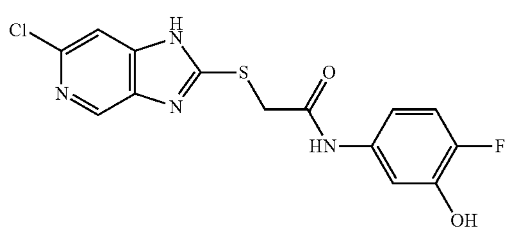 [SMILES: O=C(CSc1nc2cnc(Cl)cc2[nH]1)Nc1ccc(F)c(O)c1] | C$_{14}$H$_{10}$ClFN$_4$O$_2$S 352.77 | 0.170 | + |
| 38 | 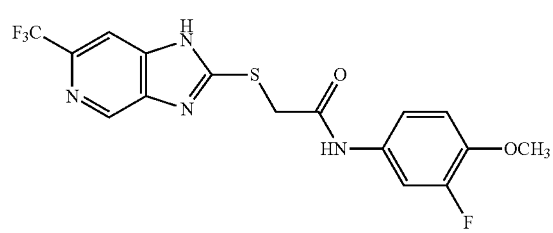 [SMILES: COc1ccc(NC(=O)CSc2nc3cnc(C(F)(F)F)cc3[nH]2)cc1F] | C$_{16}$H$_{12}$F$_4$N$_4$O$_2$S 400.35 | 0.487 | + |
| 42 | 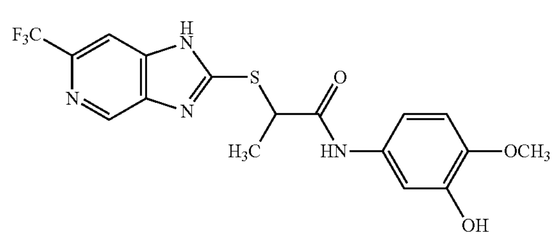 [SMILES: COc1ccc(NC(=O)C(C)Sc2nc3cnc(C(F)(F)F)cc3[nH]2)cc1O] | C$_{17}$H$_{15}$F$_3$N$_4$O$_3$S 412.39 | 11.35 | NT |

TABLE 1-continued
3H-Imidazo [4,5-c] Pyridine Series 1 of ENPP1 Inhibitors
| Compound Number | Structure | MW. | ENPP1 inhibition ($IC_{50}$) (μM) | ENPP1 Mineral assay (50% inhibition at 50 μM) |
|---|---|---|---|---|
| 44 | 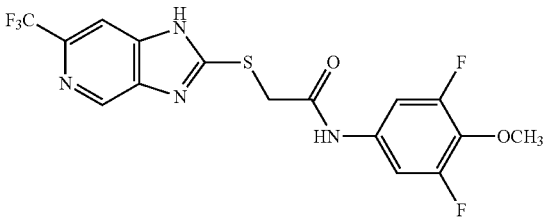 [SMILES: COc1c(F)cc(NC(=O)CSc2nc3cnc(C(F)(F)F)cc3[nH]2)cc1F] | $C_{16}H_{11}F_5N_4O_2S$ 418.34 | 10.2 | NT |
| 45 | 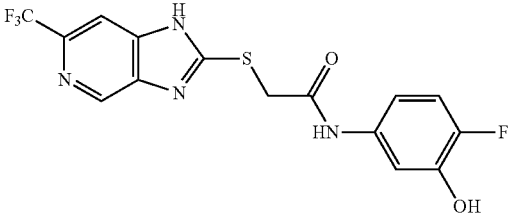 [SMILES: O=C(CSc1nc2cnc(C(F)(F)F)cc2[nH]1)Nc1ccc(F)c(O)c1] | $C_{15}H_{10}F_4N_4O_2S$ 386.32 | 0.651 | + |
| 61 | 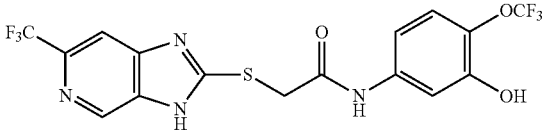 [SMILES: O=C(CSc1nc2cc(C(F)(F)F)ncc2[nH]1)Nc1ccc(OC(F)(F)F)c(O)c1] | $C_{16}H_{10}F_6N_4O_3S$ 452.33 | 22.61 | NT |
| 49 | 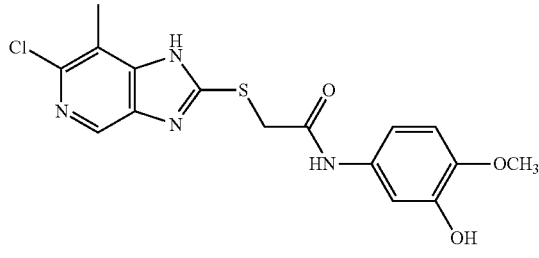 [SMILES: COc1ccc(NC(=O)CSc2nc3cnc(Cl)c(C)c3[nH]2)cc1O] | $C_{16}H_{15}ClN_4O_3S$ 378.83 | 0.667 | NT |
| 50 | 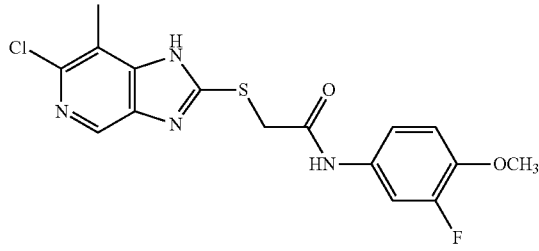 [SMILES: COc1ccc(NC(=O)CSc2nc3cnc(Cl)c(C)c3[nH]2)cc1F] | $C_{16}H_{14}ClFN_4O_2S$ 380.82 | 5.627 | NT |
| 51 | 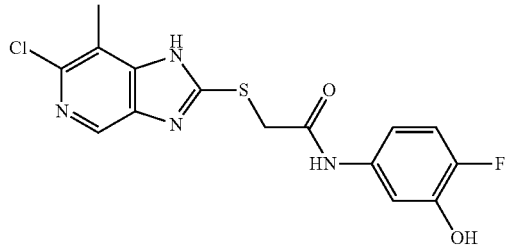 [SMILES: Cc1c(Cl)ncc2nc(SCC(=O)Nc3ccc(F)c(O)c3)[nH]c12] | $C_{15}H_{12}ClFN_4O_2S$ 366.80 | 1.269 | NT |

TABLE 1-continued

3H-Imidazo [4,5-c] Pyridine Series 1 of ENPP1 Inhibitors

| Compound Number | Structure | MW. | ENPP1 inhibition ($IC_{50}$) (μM) | ENPP1 Mineral assay (50% inhibition at 50 μM) |
|---|---|---|---|---|
| 52 | 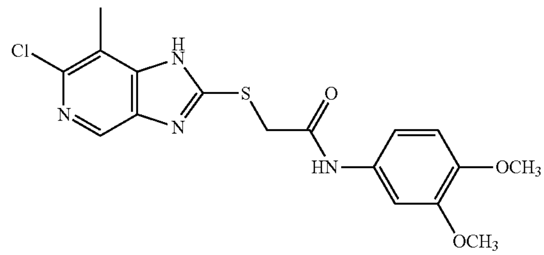 [SMILES: COc1ccc(NC(=O)CSc2nc3cnc(Cl)c(C)c3[nH]2)cc1OC] | $C_{17}H_{17}ClN_4O_3S$ 392.86 | 1.138 | NT |
| 62 | 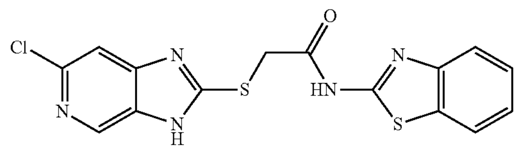 [SMILES: O=C(CSc1nc2cc(Cl)ncc2[nH]1)Nc1nc2ccccc2s1] | $C_{15}H_{10}ClN_5OS_2$ 375.85 | 10.86 | NT |
| 67 | 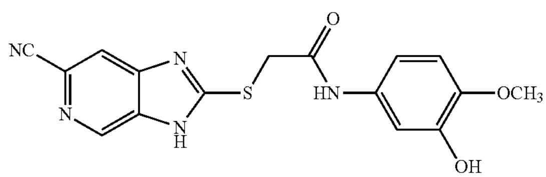 [SMILES: COc1ccc(NC(=O)CSc2nc3cc(C#N)ncc3[nH]2)cc1O] | $C_{16}H_{13}N_5O_3S$ 355.3720 | 0.179 | NT |
| 54 | 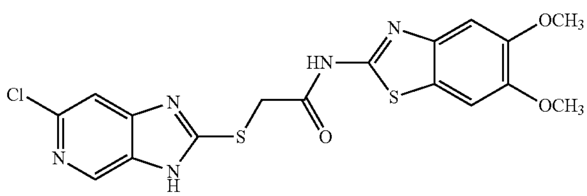 [SMILES: COc1cc2nc(NC(=O)CSc3nc4cc(Cl)ncc4[nH]3)sc2cc1OC] | $C_{17}H_{14}ClN_5O_3S_2$ 435.90 | 5.728 | NT |
| 68 | 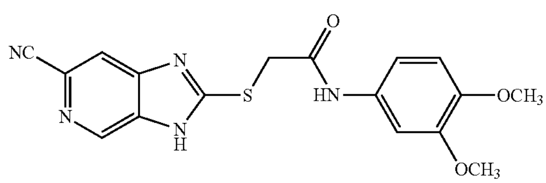 [SMILES: COc1ccc(NC(=O)CSc2nc3cc(C#N)ncc3[nH]2)cc1OC] | $C_{17}H_{15}N_5O_3S$ 369.40 | 0.114 | + |
| 69 | 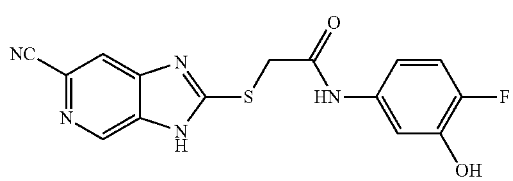 [SMILES: N#Cc1cc2nc(SCC(=O)Nc3ccc(F)c(O)c3)[nH]c2cn1] | $C_{15}H_{10}FN_5O_2S$ 343.34 | 0.216 | NT |
| 70 | 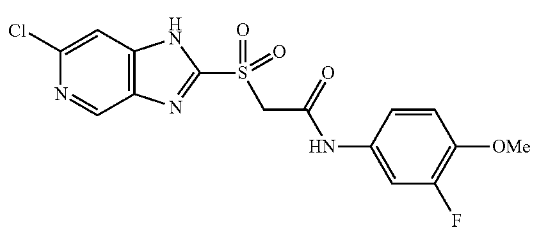 [SMILES: COc1ccc(NC(=O)CS(=O)(=O)c2nc3cnc(Cl)cc3[nH]2)cc1F] | $C_{15}H_{12}ClFN_4O_4S$ 398.79 | 30.18 | NT |

TABLE 1-continued

3H-Imidazo [4,5-c] Pyridine Series 1 of ENPP1 Inhibitors

| Compound Number | Structure | MW. | ENPP1 inhibition (IC$_{50}$) (μM) | ENPP1 Mineral assay (50% inhibition at 50 μM) |
|---|---|---|---|---|
| 77 | 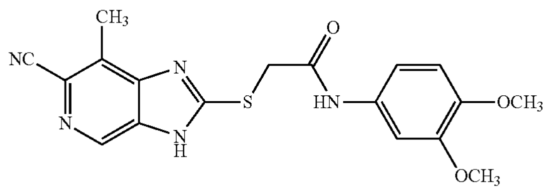 [SMILES: COc1ccc(NC(=O)CSc2nc3c(C)c(C#N)ncc3[nH]2)cc1OC] | C$_{18}$H$_{17}$N$_5$O$_3$S 383.42 | 0.265 | NT |
| 78 | 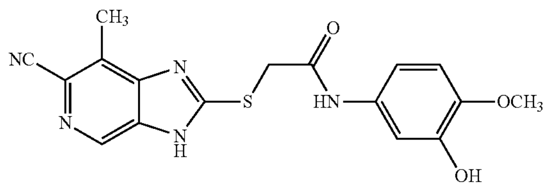 [SMILES: COc1ccc(NC(=O)CSc2nc3c(C)c(C#N)ncc3[nH]2)cc1O] | C$_{17}$H$_{15}$N$_5$O$_3$S 369.40 | 0.079 | + |
| 72 | 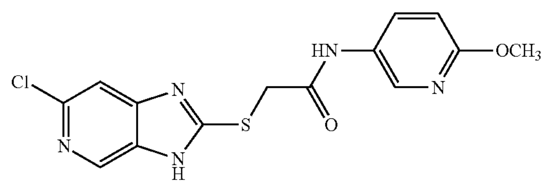 [SMILES: COc1ccc(NC(=O)CSc2nc3cc(Cl)ncc3[nH]2)cn1] | C$_{14}$H$_{12}$ClN$_5$O$_2$S 349.79 | 3.295 | NT |
| 82 | 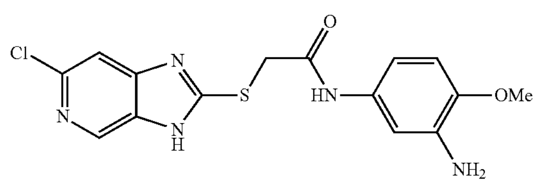 [SMILES: COc1ccc(NC(=O)CSc2nc3cc(Cl)ncc3[nH]2)cc1N] | C$_{15}$H$_{14}$ClN$_5$O$_2$S 363.82 | 6.02 | NT |
| 83 | 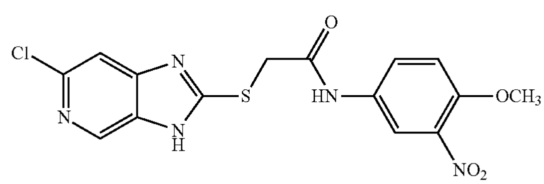 [SMILES: COc1ccc(NC(=O)CSc2nc3cc(Cl)ncc3[nH]2)cc1[N+](=O)[O-]] | C$_{15}$H$_{12}$ClN$_5$O$_4$S 393.81 | 4.55 | NT |
| 79 | 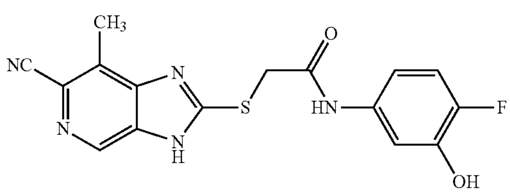 [SMILES: Cc1c(C#N)ncc2[nH]c(SCC(=O)Nc3ccc(F)c(O)c3)nc12] | C$_{16}$H$_{12}$FN$_5$O$_2$S 357.36 | 6.521 | NT |
| 85 | 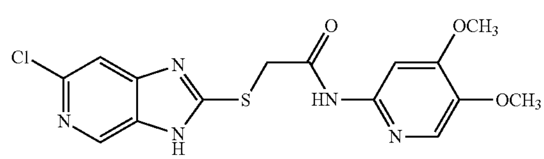 [SMILES: COc1cnc(NC(=O)CSc2nc3cc(Cl)ncc3[nH]2)cc1OC] | C$_{15}$H$_{14}$ClN$_5$O$_3$S 379.82 | 0.266 | NT |
| 93 | 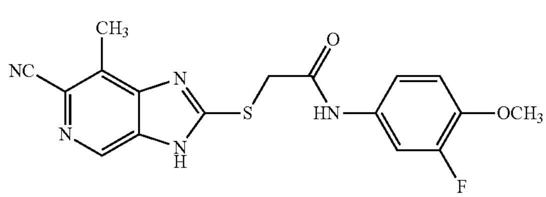 [SMILES: COc1ccc(NC(=O)CSc2nc3c(C)c(C#N)ncc3[nH]2)cc1F] | C$_{17}$H$_{14}$FN$_5$O$_2$S 371.39 | 0.224 | NT |

TABLE 1-continued

3H-Imidazo [4,5-c] Pyridine Series 1 of ENPP1 Inhibitors

| Compound Number | Structure | MW. | ENPP1 inhibition (IC$_{50}$) (μM) | ENPP1 Mineral assay (50% inhibition at 50 μM) |
|---|---|---|---|---|
| 87 | 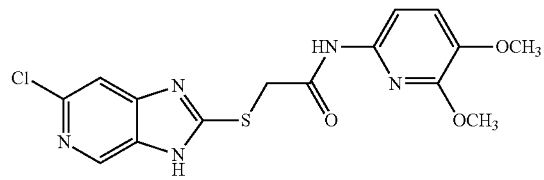 [SMILES: COc1ccc(NC(=O)CSc2nc3cc(Cl)ncc3[nH]2)nc1OC] | C$_{15}$H$_{14}$ClN$_5$O$_3$S 379.82 | 1.977 | NT |
| 89 | 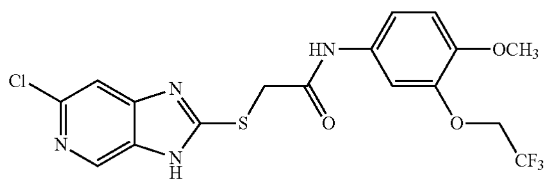 [SMILES: COc1ccc(NC(=O)CSc2nc3cc(Cl)ncc3[nH]2)cc1OCC(F)(F)F] | C$_{17}$H$_{14}$ClF$_3$N$_4$O$_3$S 446.83 | 11.32 | NT |
| 96 | 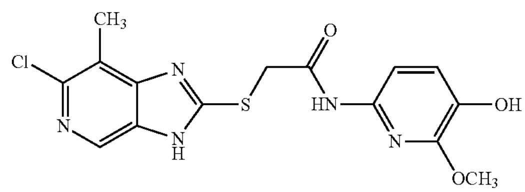 [SMILES: COc1nc(NC(=O)CSc2nc3c(C)c(Cl)ncc3[nH]2)ccc1O] | C$_{16}$H$_{14}$N$_6$O$_3$S 370.39 | 2.058 | NT |
| 91 | 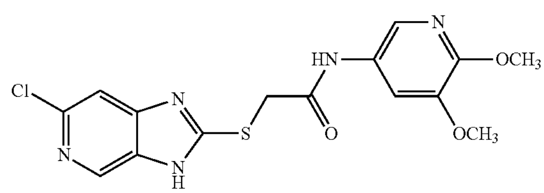 [SMILES: COc1cc(NC(=O)CSc2nc3cc(Cl)ncc3[nH]2)cnc1OC] | C$_{15}$H$_{14}$ClN$_5$O$_3$S 379.8 | NT | NT |

TABLE 2

3H-Imidazo [4,5-c] Pyridine Series 1 of ENPP1 Inhibitors

| 9 | | C$_{17}$H$_{18}$N$_4$O$_3$S 358.42 | 4.459 | NT |
|---|---|---|---|---|
| 10 | | C$_{16}$H$_{14}$N$_4$O$_3$S 342.37 | 50.0 | NT |

TABLE 2-continued

3H-Imidazo [4,5-c] Pyridine Series 1 of ENPP1 Inhibitors

| 16 | 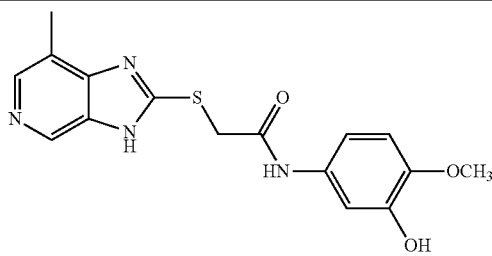 | $C_{16}H_{16}N_4O_3S$ 344.4 | 2.294 | NT |
| 18 | 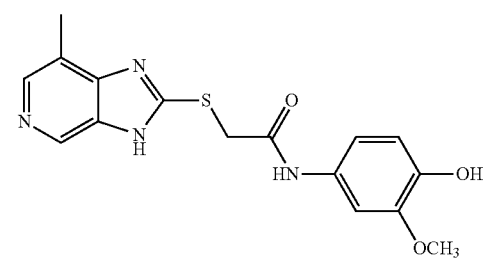 [SMILES: COc1cc(NC(=O)CSc2nc3c(C)cncc3[nH]2)ccc1O] | $C_{16}H_{16}N_4O_3S$ 344.4 | 8.371 | NT |

NA: Not Active;
NT: Not Tested;
+: active at 50 μM concentration

Prophetic Pharmaceutical Composition Examples

"Active ingredient" as used throughout these examples relates to one or more of the compounds of the invention, or a pharmaceutically acceptable salt, solvate, polymorph, hydrate and the stereochemically isomeric form thereof. The following examples of the formulation of the compounds of the present invention in tablets, suspension, injectables and ointments are prophetic.

Typical examples of recipes for the formulation of the invention are as given below. Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press). The disclosure of this reference is hereby incorporated herein by reference.

a. Pharmaceutical Composition for Oral Administration
A tablet can be prepared as follows:

| Component | Amount |
|---|---|
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
|---|---|
| Active ingredient | 10 to 500 mg |
| Sodium carbonate | 560 mg* |
| Sodium hydroxide | 80 mg* |
| Distilled, sterile water | Quantity sufficient to prepare total volumen indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of structure:

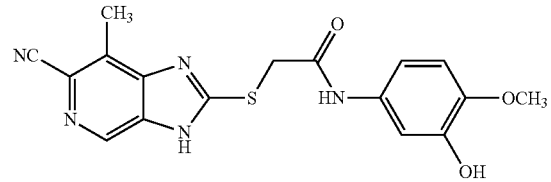 [SMILES: COc1ccc(NC(=O)CSc2nc3c(C)c(C#N)ncc3[nH]2)cc1O]

or a pharmaceutically acceptable salt thereof.

2. A pharmaceutical composition comprising a therapeutically effective amount of a compound of claim 1 and a pharmaceutically acceptable carrier.

3. A method for the treatment of a disorder of uncontrolled cellular proliferation in a mammal, the method comprising the step of administering to the mammal an effective amount of a compound of claim 1.

4. A method for treating cancer in a mammal, the method comprising the step of administering to the mammal an effective amount of a compound of claim 1.

* * * * *